United States Patent
Wallace et al.

(10) Patent No.: US 11,672,547 B2
(45) Date of Patent: *Jun. 13, 2023

(54) ORTHOPAEDIC SYSTEM AND METHOD FOR ASSEMBLING PROSTHETIC COMPONENTS

(71) Applicant: DePuy Ireland Unlimited Company, Ringaskiddy (IE)

(72) Inventors: Megan Wallace, Warsaw, IN (US); Carl F. Livorsi, Lakeville, MA (US); Jeremy Oden, Huntington, IN (US); Gregory S. Meadows, Warsaw, IN (US); Francisco A. Amaral, Acushnet, MA (US); Michael J. Brock, Warsaw, IN (US); Anthony J. Webb, Fort Wayne, IN (US); Craig S. Tsukayama, Fort Wayne, IN (US); Karen N. Moeller, Columbia City, IN (US); Richard C. Ditto, West Chester, OH (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 526 days.

This patent is subject to a terminal disclaimer.

(21) Appl. No.: 16/743,083

(22) Filed: Jan. 15, 2020

(65) Prior Publication Data
US 2020/0146695 A1 May 14, 2020

Related U.S. Application Data

(63) Continuation of application No. 15/710,311, filed on Sep. 20, 2017, now Pat. No. 10,537,341.

(51) Int. Cl.
*A61B 17/16* (2006.01)
*A61F 2/46* (2006.01)
(Continued)

(52) U.S. Cl.
CPC ........ *A61B 17/1675* (2013.01); *A61B 17/154* (2013.01); *A61B 17/164* (2013.01);
(Continued)

(58) Field of Classification Search
CPC ... A61B 17/16; A61B 17/1675; A61B 17/164; A61B 17/15; A61B 17/154; A61F 2/46; A61F 2/4684; B23P 19/04
See application file for complete search history.

(56) References Cited

U.S. PATENT DOCUMENTS

| 4,710,075 A | 12/1987 | Davison |
| 4,952,213 A | 8/1990 | Bowman et al. |

(Continued)

FOREIGN PATENT DOCUMENTS

| CN | 101742972 A | 6/2010 |
| CN | 101849864 A | 10/2010 |

(Continued)

OTHER PUBLICATIONS

India Examination Report for Application No. 201814034442, dated Mar. 14, 2022, 6 pages.

(Continued)

*Primary Examiner* — Christopher J Beccia
(74) *Attorney, Agent, or Firm* — Barnes & Thornburg LLP

(57) ABSTRACT

An orthopaedic system and method to assemble an orthopaedic prosthesis is disclosed. The system may also include prosthetic trial components, which may be used to size and select the components of the orthopaedic prosthesis. The system may include components of the orthopaedic prosthesis such as, for example, a prosthetic femoral component, a prosthetic tibial component, a prosthetic stem component, and a prosthetic sleeve component.

20 Claims, 27 Drawing Sheets

(51) Int. Cl.
  *A61B 17/15* (2006.01)
  *A61B 17/02* (2006.01)
  *A61F 2/30* (2006.01)
  *A61F 2/38* (2006.01)
(52) U.S. Cl.
  CPC .......... *A61F 2/4637* (2013.01); *A61F 2/4684* (2013.01); *A61B 17/1659* (2013.01); *A61B 2017/0268* (2013.01); *A61F 2/38* (2013.01); *A61F 2002/30738* (2013.01)

(56) References Cited

U.S. PATENT DOCUMENTS

| | | | |
|---|---|---|---|
| 5,100,409 A | 3/1992 | Coates et al. | |
| 5,176,684 A | 1/1993 | Ferrante et al. | |
| 5,356,414 A | 10/1994 | Cohen et al. | |
| 5,415,662 A | 5/1995 | Ferrante et al. | |
| 5,489,311 A | 2/1996 | Cipolletti | |
| 5,569,259 A | 10/1996 | Ferrante et al. | |
| 5,571,194 A | 11/1996 | Gabriel | |
| 5,601,563 A | 2/1997 | Burke et al. | |
| 5,613,970 A | 3/1997 | Houston et al. | |
| 5,634,927 A | 6/1997 | Houston et al. | |
| 5,681,316 A | 10/1997 | DeOrio et al. | |
| 5,702,460 A | 12/1997 | Carls et al. | |
| 5,720,752 A | 2/1998 | Elliott et al. | |
| 5,769,854 A | 6/1998 | Bastian et al. | |
| 5,931,841 A | 8/1999 | Ralph | |
| 5,976,147 A | 11/1999 | Lasalle et al. | |
| 6,203,575 B1 | 3/2001 | Farey | |
| 6,228,091 B1 | 5/2001 | Lombardo et al. | |
| 6,620,168 B1 | 9/2003 | Lombardo et al. | |
| 7,497,874 B1 | 3/2009 | Metzger et al. | |
| 7,744,600 B2 | 6/2010 | Rangaiah et al. | |
| 7,963,968 B2 | 6/2011 | Dees, Jr. | |
| 8,002,777 B2 | 8/2011 | Fox et al. | |
| 8,036,881 B2 | 10/2011 | Liljeryd et al. | |
| 8,187,280 B2 | 5/2012 | May et al. | |
| 8,273,090 B2* | 9/2012 | Alvarez | A61B 17/157 606/88 |
| 8,273,093 B2 | 9/2012 | Klotz et al. | |
| 8,377,141 B2 | 2/2013 | McMinn | |
| 8,425,524 B2 | 4/2013 | Aker et al. | |
| 8,771,280 B2 | 7/2014 | Bailey et al. | |
| 8,979,847 B2 | 3/2015 | Belcher et al. | |
| 8,986,310 B2 | 3/2015 | Bailey et al. | |
| 9,028,501 B2 | 5/2015 | Thomas et al. | |
| 9,113,915 B2 | 8/2015 | Thomas et al. | |
| 9,220,511 B2 | 12/2015 | Chaney et al. | |
| 9,579,113 B2 | 2/2017 | Thomas et al. | |
| 9,636,122 B2 | 5/2017 | Chaney et al. | |
| 9,962,173 B2 | 5/2018 | Thomas et al. | |
| 10,537,341 B2* | 1/2020 | Wallace | A61B 17/1675 |
| 2001/0001121 A1 | 5/2001 | Lombardo et al. | |
| 2003/0114859 A1 | 6/2003 | Grusin et al. | |
| 2004/0039450 A1 | 2/2004 | Griner et al. | |
| 2004/0078043 A1 | 4/2004 | Masini | |
| 2004/0087960 A1 | 5/2004 | Kinnett | |
| 2004/0122441 A1 | 6/2004 | Muratsu | |
| 2004/0153087 A1 | 8/2004 | Sanford et al. | |
| 2004/0225368 A1 | 11/2004 | Plumet et al. | |
| 2005/0192588 A1 | 9/2005 | Garcia | |
| 2005/0267485 A1 | 12/2005 | Cordes et al. | |
| 2006/0173463 A1 | 8/2006 | Dees | |
| 2006/0195113 A1 | 8/2006 | Masini | |
| 2006/0241634 A1 | 10/2006 | Tuttle et al. | |
| 2007/0010890 A1 | 1/2007 | Collazo | |
| 2007/0073305 A1 | 3/2007 | Lionberger et al. | |
| 2007/0173850 A1 | 7/2007 | Rangaiah et al. | |
| 2008/0091273 A1 | 4/2008 | Hazebrouck | |
| 2008/0183177 A1 | 7/2008 | Fox et al. | |
| 2008/0228189 A1 | 9/2008 | Fox et al. | |
| 2008/0275457 A1 | 11/2008 | Meek et al. | |
| 2008/0312659 A1 | 12/2008 | Metzger et al. | |
| 2009/0088762 A1 | 4/2009 | Koenemann | |
| 2009/0088763 A1 | 4/2009 | Aram et al. | |
| 2009/0125114 A1 | 5/2009 | May et al. | |
| 2009/0204115 A1 | 8/2009 | Dees, Jr. et al. | |
| 2009/0222008 A1 | 9/2009 | Hogg et al. | |
| 2009/0228016 A1* | 9/2009 | Alvarez | A61B 17/155 606/88 |
| 2010/0076441 A1 | 3/2010 | May et al. | |
| 2010/0121334 A1 | 5/2010 | Couture et al. | |
| 2010/0234850 A1 | 9/2010 | Dees, Jr. et al. | |
| 2011/0093081 A1 | 4/2011 | Chana et al. | |
| 2011/0218541 A1 | 9/2011 | Bailey et al. | |
| 2011/0307067 A1 | 12/2011 | Dees | |
| 2012/0310246 A1 | 12/2012 | Belcher et al. | |
| 2012/0323334 A1 | 12/2012 | Jones et al. | |
| 2013/0144296 A1 | 6/2013 | Yoko et al. | |
| 2013/0165936 A1 | 6/2013 | Myers | |
| 2013/0325014 A1 | 12/2013 | Sordelet et al. | |
| 2013/0325016 A1 | 12/2013 | Sordelet et al. | |
| 2013/0325018 A1 | 12/2013 | Thomas et al. | |
| 2013/0325019 A1 | 12/2013 | Thomas et al. | |
| 2013/0325021 A1 | 12/2013 | Sordelet et al. | |
| 2013/0325136 A1 | 12/2013 | Thomas et al. | |
| 2014/0259608 A1* | 9/2014 | Matyas | B66F 1/08 29/700 |
| 2014/0276836 A1 | 9/2014 | Chaney et al. | |
| 2014/0276858 A1 | 9/2014 | Major et al. | |
| 2014/0276859 A1 | 9/2014 | Chaney et al. | |
| 2014/0296929 A1* | 10/2014 | Stacey | A61F 2/461 606/86 R |
| 2015/0202056 A1 | 7/2015 | Matyas | |
| 2015/0230939 A1 | 8/2015 | Froidevaux et al. | |
| 2015/0313727 A1 | 11/2015 | Waite, II et al. | |
| 2016/0089161 A1 | 3/2016 | Ardito et al. | |
| 2016/0206445 A1* | 7/2016 | Gheevarughese | A61F 2/4607 |
| 2017/0105848 A1 | 4/2017 | Wogoman et al. | |
| 2017/0196709 A1 | 7/2017 | Matyas et al. | |
| 2017/0313727 A1 | 11/2017 | Aga et al. | |
| 2019/0083106 A1 | 3/2019 | Wallace et al. | |
| 2019/0083112 A1 | 3/2019 | Wallace et al. | |
| 2019/0083113 A1 | 3/2019 | Wallace et al. | |

FOREIGN PATENT DOCUMENTS

| | | |
|---|---|---|
| CN | 101879099 A | 11/2010 |
| CN | 202920415 U | 5/2013 |
| EP | 947169 A2 | 10/1999 |
| EP | 2145590 A1 | 1/2010 |
| EP | 2777550 A2 | 9/2014 |
| EP | 2777556 A2 | 9/2014 |
| FR | 2748389 A1 | 11/1997 |
| FR | 2752519 A1 | 2/1998 |
| FR | 2943528 A1 | 10/2010 |
| GB | 2323037 A | 9/1998 |
| JP | 11104155 A | 4/1999 |
| JP | 2009006066 A | 1/2009 |
| JP | 2010057527 A | 3/2010 |
| RU | 2080840 C1 | 6/1997 |
| RU | 2110233 C1 | 5/1998 |
| RU | 2607957 C2 | 1/2017 |
| RU | 2611926 C2 | 3/2017 |
| SU | 1461430 A1 | 2/1989 |
| UA | 85954 C2 | 3/2009 |
| UA | 85954 U | 12/2013 |
| WO | 9625123 A2 | 8/1996 |
| WO | 9730661 A1 | 8/1997 |
| WO | 9852499 A1 | 11/1998 |
| WO | 0013597 A1 | 3/2000 |
| WO | 2007041644 A1 | 4/2007 |
| WO | 2007114841 A1 | 10/2007 |
| WO | 2010019284 A1 | 2/2010 |
| WO | 2016115330 A1 | 7/2016 |

OTHER PUBLICATIONS

Partial European Search Report for Application No. 18194422.4, dated Feb. 27, 2019, 11 pages.
Extended European Search Report for Application No. 18194422.4, dated Jul. 4, 2019, 11 pages.

(56) References Cited

OTHER PUBLICATIONS

Extended European Search Report dated Feb. 19, 2019, 8 pages.
Zimmer NexGen LCCK, Surgical Technique for use with LCCK 4-in-1 Instrument, 2009, 52 pages.
DePuy Orthopaedics, Inc., Sigma Revision and M.B.T. Revision Tray, Surgical Technique, 2008, 82 pages.
Smith & Nephew, Legion, Revision Knee System, Surgical Technique, 2005, 40 pages.
Biomet, Vanguard SSK, Revision System, Surgical Technique, Feb. 2008, 64 pages.
GMK Revision, Surgical Technique, Ref. 99.27.12US rev. 1, 1999, 74 pages.
PFC Sigma RP-F, Specialist 2 Instruments, Surgical Technique, Performance in Flexion, 2007, 32 pages.
P.F.C. Sigma Rotating Platform Knee System with M.B.T Tray, Primary Procedure with a Curved or Posterior Stablised Implant, 2003, 43 pages.
LCS High Performance Instruments, Surgical Technique, 2008, 44 pages.
Sigma High Performance Instruments, Design Rationale, 2007, 12 pages.
Sigma High Performance Instruments, Classic Surgical Technique, 2010, 52 pages.
Attune Knee System Surgical Technique, 2013, 73 pages.
Redacted Memorandum with Appendix A, dated Jan. 26, 2010, outlining a surgical instrument evaluation that commenced in 2010, 37 pages.
"Reinstall Wave 1 Evaluation Surgical Technique," used during the surgical instrument evaluation that commenced in 2010, 36 pages.
Tray configuration cards showing the instruments used during the surgical instrument evaluation that commenced in 2010, 8 pages.
Declaration of Gary M. Lindsay dated Dec. 23, 2014, 5 pages.
International Search Report and Written Opinion, International Application No. PCT/US2017/033295, dated Dec. 18, 2017, 8 pages.
International Search Report issued in connection with International Application No. PCT/US2017/033307, dated Sep. 25, 2017, 13 pages.
International Search Report issued in connection with International Application No. PCT/US2017/033278, dated Aug. 30, 2017, 13 pages.
International Search Report issued in connection with International Application No. PCT/US2017/033278, dated Nov. 21, 2017, 8 pages.
Zimmer Biomet, Vanguard 360 Revision Knee System, copyrighted 2016, 84 pages.
English translation of Russia Search Report for Application No. 2018132860/14, dated Dec. 11, 2021, 2 pages.
English translation of Russia Search Report for Application No. 2018132737/14, dated Dec. 11, 2021, 2 pages.
Russia Office Action for Application No. 2018133173/14, dated Feb. 17, 2022, 10 pages.
Chinese Office Action for Chinese Application No. 201811103720.5, dated Nov. 3, 2022, 6 pages.

* cited by examiner

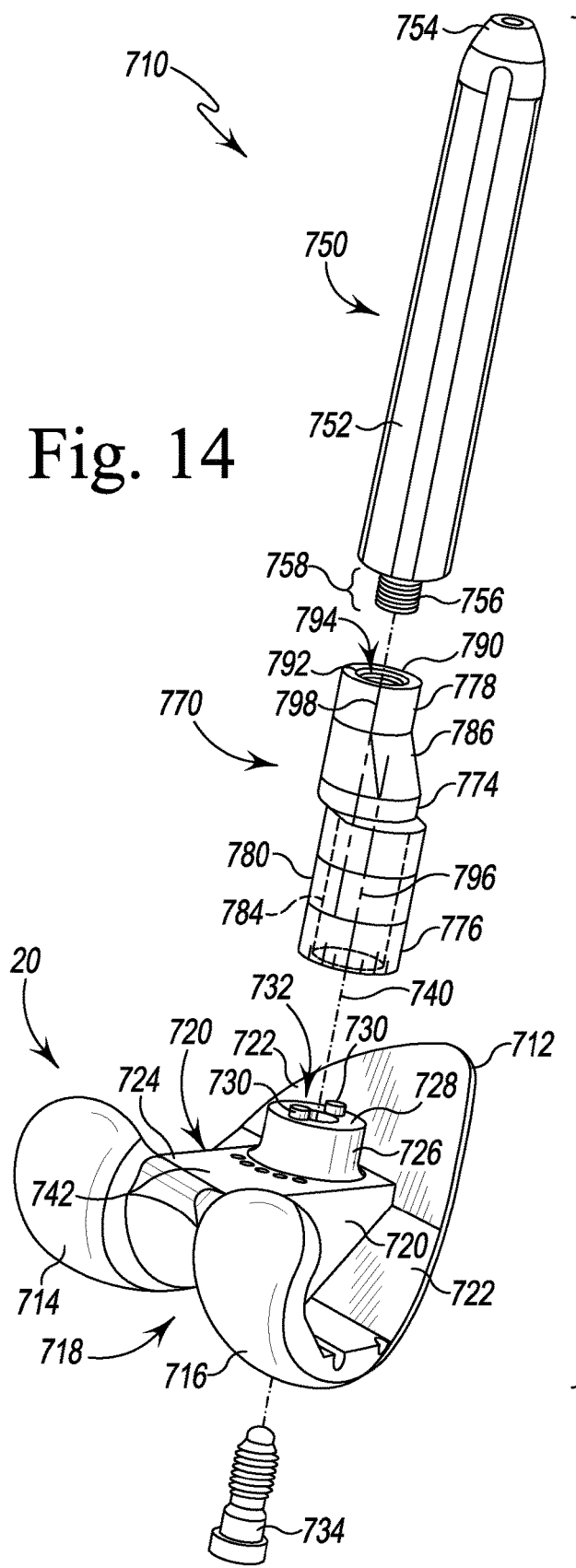
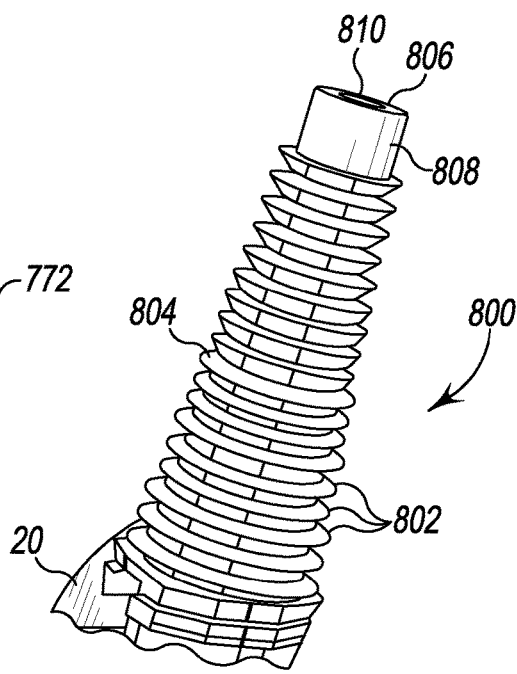
Fig. 14
Fig. 15

ORTHOPAEDIC SYSTEM AND METHOD FOR ASSEMBLING PROSTHETIC COMPONENTS

This is a continuation application claiming priority under 35 U.S.C. § 120 to U.S. patent application Ser. No. 15/710,311, now U.S. Pat. No. 10,537,341, which was filed on Sep. 20, 2017, which is expressly incorporated herein by reference.

CROSS-REFERENCE

Cross-reference is made to U.S. patent application Ser. No. 15/710,348, now U.S. Pat. No. 10,537,446, entitled "Method and Instruments for Assembling an Orthopaedic Prosthesis," and U.S. patent application Ser. No. 15/710,373, now U.S. Pat. No. 10,543,001, entitled "Method and Instruments for Assembling a Femoral Orthopaedic Prosthesis," which are filed on the same day as this application and are expressly incorporated into this application by reference.

TECHNICAL FIELD

The present disclosure relates generally to orthopaedic instruments for use in the performance of an orthopaedic joint replacement procedure, and, more particularly, to orthopaedic surgical instruments for use in the performance of a knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes multiple prosthetic components, including a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis is surgically removed and a replacement knee prosthesis is implanted. In some revision knee surgeries, all of the components of the previously-implanted knee prosthesis, including, for example, the tibial tray, the femoral component, and the polymer bearing, may be surgically removed. In other revision knee surgeries, only part of the previously-implanted knee prosthesis may be removed and replaced.

During any knee surgery, the orthopaedic surgeon typically uses a variety of different orthopaedic surgical instruments such as, for example, cutting blocks, reamers, drill guides, and other surgical instruments to prepare the patient's bones to receive the knee prosthesis. The surgeon may also utilize orthopaedic surgical instruments such as prosthetic trial components to size and select the appropriate prosthetic components. Such prosthetic trial components are shaped to match the size and shape as their corresponding prosthetic components but are not configured to be permanently implanted into the patient's bones. Instead, prosthetic trial components may be temporarily attached during surgery to the patient's bones in place of the prosthetic components to evaluate fit, range of motion, and other aspects of the patient's joint and assist the surgeon in selecting the prosthetic components of the orthopaedic prosthesis for implantation.

SUMMARY

According to one aspect of the disclosure, an orthopaedic system and method for replacing a patient's knee joint is disclosed. The system includes the surgical instruments used to assemble an orthopaedic prosthesis. In some embodiments, the system may also include prosthetic trial components, which may be used to size and select the components of the orthopaedic prosthesis. The system may include components of the orthopaedic prosthesis such as, for example, a prosthetic femoral component, a prosthetic tibial component, a prosthetic stem component, and a prosthetic sleeve component.

The surgical instruments of the orthopaedic system may include an instrument base configured to receive a prosthetic trial carrier. The trial carrier may be configured to mount a prosthetic trial component to the instrument base. It should be appreciated that the system may include a number of prosthetic trial carriers, each of which is configured to receive a different configuration of prosthetic trial component. In some embodiments, the prosthetic trial component configurations may include a femoral trial component having a size and shape corresponding to a size and shape of a prosthetic femoral component, a tibial trial component having a size and shape corresponding to a size and shape of a prosthetic tibial component, and a stem trial component having a size and shape corresponding to a size and shape of a prosthetic stem.

In some embodiments, the instrument base may be configured to receive a prosthetic component carrier, which is configured to mount a prosthetic component to the instrument base. It should be appreciated that the system may include a number of prosthetic component carriers, each of which is configured to receive a different configuration of prosthetic component. It should be appreciated that in some embodiments the same carrier may be configured to selectively mount the prosthetic trial component and the corresponding prosthetic component to the instrument base.

The surgical instruments of the orthopaedic system may include a stabilizing or support arm configured to be coupled to the instrument base. The support arm may be configured to engage a portion of a prosthetic trial component and/or a portion of a prosthetic component during assembly to retain the prosthetic trial or prosthetic component in position during assembly.

In some embodiments, the surgical instrument system may further comprise a wrench including an open slot sized to receive a femoral sleeve. The open slot may be defined by a plurality of surfaces of the wrench. The wrench may also include a plurality of lobes extending from the surfaces into the open slot. Each lobe may be shaped to engage a surface of the femoral sleeve.

According another aspect of the disclosure, a surgical instrument system for selecting and assembling an orthopaedic prosthesis for a patient's knee joint is disclosed. The surgical instrument system comprises a base including a mounting platform, a first carrier including a mounting block configured to be selectively positioned on the mounting platform, and a second carrier configured to be selectively positioned on the mounting platform in place of the first carrier. The first carrier includes a post extending at a non-orthogonal angle relative to the mounting block, and the post includes a distal end that is sized to be received in a passageway of a prosthetic femoral component. The second carrier includes a first clamp plate and a second clamp plate that are moveable to grip a prosthetic tibial component between the first clamp plate and the second clamp plate.

In some embodiments, the surgical instrument system may further comprise a third carrier configured to mount a femoral trial component to the base. The third carrier may include a mounting block configured to be selectively positioned on the mounting platform in place of the first carrier and the second carrier. The third carrier may further include a post extending at an orthogonal angle relative to the mounting block to a distal end. The distal end of the post of the third carrier may include planar end surface and a pin extending from the end surface that is sized to be received in a pocket of a femoral trial component corresponding to the prosthetic femoral component. In some embodiments, the pin may be configured to be received in a fastener of the prosthetic femoral component.

In some embodiments, the first carrier may further include a pair of walls connected to the post and extending outwardly from the mounting block. The walls may be sized to be received in the intercondylar notch of the prosthetic femoral component. Additionally, in some embodiments, the third carrier may also include a pair of walls connected to the post and extending outwardly from the mounting block. The walls may be sized to be received in the intercondylar notch of the femoral trial component.

It should be appreciated that in some embodiments the surgical instrument system may further comprise a shim having a channel extending along a first axis and a thickness defined along a second axis extending orthogonal to the first axis. The thickness of the shim may correspond to a width of the intercondylar notch of the prosthetic femoral component and/or the femoral trial component. The channel may be sized to receive each wall of the pair of walls of the first carrier and/or the third carrier to selectively mount the shim on each wall.

Additionally, in some embodiments, the shim may include an opening and a pair of side surfaces that extend inwardly from the opening to a base surface. The pair of side surfaces and the base surface may cooperate to define the channel in the shim. The shim may further include a groove that is defined in one side surface of the pair of side surfaces and extends along the first axis. In some embodiments, each wall of the pair of walls may include a rib extending outwardly from a first planar surface. The rib of each wall may be sized to be positioned in the groove of the shim to permit the shim to be mounted in only a single orientation on each wall. In some embodiments, the rib of one wall may extend in the same direction as the rib of the other wall.

In some embodiments, the shim may be one shim of a plurality of shims. Each shim may have a different thickness from the other shims of the plurality of shims, and each thickness may correspond to a width of intercondylar notch of one of a plurality of prosthetic femoral components.

As discussed above, the surgical instrument system includes a second carrier configured to receive a prosthetic tibial component. In some embodiments, the second carrier may include a screw-type mechanism to move the second clamp plate and the first clamp plate. One of the first clamp plate and the second clamp plate of the second carrier may include a concave curved wall shaped to engage a convex curved anterior wall of the prosthetic tibial component. The other of the first clamp plate and the second clamp plate may include a convex curved wall that is positioned between, and connected to, a pair of concave curved walls. The convex curved wall and the pair of concave curved walls may be shaped to engage a posterior wall of the prosthetic tibial component.

In some embodiments, the second clamp plate of the second carrier may include a rear slot sized to receive a posterior buttress of the prosthetic tibial component and a forward slot sized to receive an anterior buttress of the prosthetic tibial component.

In some embodiments, the base of the surgical instrument system may include a stationary housing, and the mounting platform may be rotatively coupled to the stationary housing to permit the mounting platform to rotate 360 degrees relative to the stationary housing about a vertical axis. In some embodiments, the base may further include a locking clutch operable to prevent the mounting platform from rotating relative to the stationary housing.

In some embodiments, the surgical instrument system may further comprise a support or stabilizer arm positioned above the base. The support arm may be attached to the stationary housing. Additionally, the support arm may be moveable in a horizontal plane relative to the mounting platform.

According to another aspect of the disclosure, a surgical instrument system for selecting and assembling an orthopaedic prosthesis for a patient's knee joint comprises a base including a stationary housing, a mounting platform that is rotatively coupled to the stationary housing to permit the mounting platform to rotate 360 degrees about a vertical axis extending through the stationary housing, and a locking clutch operable to prevent the mounting platform from rotating relative to the stationary housing. The surgical instrument system also comprises a support arm removably coupled to the stationary housing. The support arm is moveable in a horizontal plane relative to the vertical axis. The surgical instrument system further comprises a plurality of prosthetic trial carriers configured to be separately coupled to the mounting platform to rotate with the mounting platform. Each prosthetic trial carrier is configured to receive a prosthetic trial component having a shape and size corresponding to a prosthetic component of the orthopaedic prosthesis.

In some embodiments, the support arm may include an elongated body positioned in the horizontal plane, a first shaft positioned in the horizontal plane and extending outwardly from the elongated body to a proximal tip, and a second shaft extending outwardly from the elongated body parallel to the first shaft to a proximal tip. A channel may be defined between the proximal tips of the first shaft and the second shaft. The channel is sized to receive a portion of a prosthetic trial component positioned on one of the prosthetic trial carrier when the prosthetic trial carrier is coupled to the mounting platform. Additionally, in some embodiments, the surgical instrument system may further comprise a user-operated knob operable to move the first shaft toward the second shaft to decrease a width of the channel.

In some embodiments, the mounting platform of the base may include a pair of upwardly-extending pins. Each prosthetic trial carrier may include a pair of apertures sized to separately receive the upwardly-extending pins. Additionally, in some embodiments, one upwardly-extending pin has a different configuration (e.g., size and/or shape) from the other upwardly-extending pin such that the prosthetic trial carrier may be mounted in only a single orientation on the mounting platform.

In some embodiments, the surgical instrument system may further comprise a femoral trial component configured to be mounted on at least one of the prosthetic trial carriers. The femoral trial component may include a pair of convexly curved condyle surfaces. The system may also include an adaptor component configured to be secured to a proximal end of the femoral trial component, and a stem trial component configured to be secured to a proximal end of the adaptor. The channel of the support arm may be sized to receive the adaptor component.

In some embodiments, the system may comprise a shim having a channel extending along a first axis and a thickness defined along a second axis extending orthogonal to the first axis. The thickness of the shim may correspond to a width of the intercondylar notch of the femoral trial component, and the channel may be sized to receive a wall of the at least one of the prosthetic trial carriers to permit the shim to be mounted on the prosthetic trial carrier.

In some embodiments, the adaptor component may include a visual indicia positioned to face the elongated body of the support arm when the adaptor component is received in the channel of the support arm.

According to another aspect, the surgical instrument system for assembling an orthopaedic prosthesis for a patient's knee joint comprises a base including a stationary housing, and a mounting platform that is rotatively coupled to the stationary housing to permit the mounting platform to rotate 360 degrees about a vertical axis extending through the stationary housing. The surgical instrument system also comprises a support arm removably coupled to the stationary housing. The support arm is moveable in a horizontal plane relative to the vertical axis. The surgical instrument system further comprises a prosthetic component carrier configured to be coupled to the mounting platform to rotate with the mounting platform. The prosthetic component carrier is configured to receive a prosthetic component of the orthopaedic prosthesis.

In some embodiments, the base may further include a locking clutch operable to prevent the mounting platform from rotating relative to the stationary housing.

In some embodiments, the base and the mounting platform may include visual indicia to indicate the position of the mounting platform relative to the base.

In some embodiments, the prosthetic component carrier may be one of a plurality of prosthetic component carriers. Each prosthetic component carrier may be configured to receive a different configuration of prosthetic component. It should be appreciated that the configurations of prosthetic components may include a prosthetic femoral component or prosthetic tibial component.

According to another aspect of the disclosure, the orthopaedic system may include any of the surgical instrument systems described above. As described above, the orthopaedic system may also include the prosthetic components that form the orthopaedic prosthesis and the prosthetic trial components corresponding to the prosthetic components.

According to another aspect, a method of assembling an orthopaedic prosthesis is disclosed. The method comprises aligning a tibial trial construct with a surgical instrument that includes a mounting platform and a stabilizer arm. The tibial trial construct comprises a base trial that defines a first axis and an offset adaptor trial that defines a second axis that is offset from the first axis. The method also comprises positioning the tibial trial construct on the mounting platform, rotating the mounting platform to position the first axis and the second axis in a plane extending vertically through the stabilizer arm, advancing the stabilizer arm along the vertically-extending plane to engage the stabilizer arm with the tibial trial construct, and locking the mounting platform to prevent rotation relative to the stabilizer arm. The method further comprises positioning a tibial prosthetic component on the mounting platform after removing the tibial trial construct such that a third axis defined by a distal post of the tibial prosthetic component is positioned in the plane, and positioning a tibial offset adaptor on the distal post. The tibial offset adaptor includes a distal end that defines a fourth axis that is offset from the third axis. The method comprises rotating the distal end of the tibial offset adaptor to position the fourth axis in the vertically-extending plane, and securing the tibial offset adaptor to the tibial prosthetic component with the third axis and the fourth axis positioned in the plane.

In some embodiments, the method may further comprise attaching a carrier to the mounting platform. The step of positioning the tibial trial construct on the mounting platform may comprise positioning the tibial trial construct on the carrier, and advancing a first clamp plate of the carrier into engagement with the base trial of the tibial trial construct to secure the base trial between the first clamp plate and a second clamp plate of the carrier.

Additionally, in some embodiments, the step of positioning the tibial prosthetic component on the mounting platform after removing the tibial trial construct may include positioning the tibial prosthetic component on the carrier, and advancing the first clamp plate into engagement with the tibial prosthetic component to secure the tibial prosthetic component between the first clamp plate and the second clamp plate.

In some embodiments, the method may further comprise securing a stem component to the distal end of the tibial offset adaptor. The method may also comprise advancing the stabilizer arm along the vertically-extending plane to engage the stabilizer arm with the distal end of the tibial offset adaptor after rotating the distal end of the tibial offset adaptor to position the third axis in the vertically-extending plane.

Additionally, in some embodiments, the step of advancing the stabilizer arm along the vertically-extending plane to engage the stabilizer arm with the distal end of the tibial offset adaptor may include positioning the distal end of the tibial offset adaptor in a channel defined in the proximal tip of the stabilizer arm.

In some embodiments, the step of advancing the stabilizer arm along the vertically-extending plane to engage the stabilizer arm with the offset adaptor trial may include positioning the offset trial in the channel defined in the stabilizer arm.

Additionally, in some embodiments, the method may further comprise securing the offset adaptor trial in the proximal tip of the stabilizer arm before locking the mounting platform to prevent rotation relative to the stabilizer arm.

In some embodiments, the method may further comprise aligning a visual marking on the offset adaptor trial with an alignment window defined in the stabilizer arm. Additionally, in some embodiments, the step of advancing the stabilizer arm along the vertically-extending plane to engage the stabilizer arm with the offset adaptor trial further may include aligning chamfered end surfaces of the proximal tip with a sloped or tapered surface of the offset trial.

According to another aspect, a method of assembling an orthopaedic prosthesis comprises rotating a mounting platform of a surgical instrument about a vertically-extending axis, attaching a carrier to the mounting platform, and positioning a first tibial prosthetic component on the carrier. The first tibial prosthetic component includes a tibial tray and a post extending from the tibial tray. The method further comprises advancing a first clamp plate of the carrier into engagement with the tibial tray to secure the tibial tray between the first clamp plate and a second clamp plate of the carrier, and securing a second tibial prosthetic component to the post of the first tibial prosthetic component.

In some embodiments, the step of securing the second tibial prosthetic component to the post of the first tibial prosthetic component may include sliding the second tibial prosthetic component along a tapered outer surface of the post to secure the second tibial prosthetic component to the post. The second tibial prosthetic component may include a stepped outer surface.

In some embodiments, the step of securing the second tibial prosthetic component to the post of the first tibial prosthetic component further may include attaching a first end of an impactor to a distal end of the second tibial prosthetic component and applying force to a second end of the impactor.

In some embodiments, the method may further comprise selecting a tibial trial construct including a base trial and a tibial sleeve trial secured to the base trial and including a stepped outer surface corresponding to the stepped outer surface of the second tibial prosthetic component, and rotating the second tibial prosthetic component on the post of the first tibial prosthetic component to orient the second tibial prosthetic component based on the orientation of the sleeve trial relative to the base trial.

In some embodiments, the post of the first tibial prosthetic component may define a first axis, and the step of securing the second tibial prosthetic component to the post of the first tibial prosthetic component may include rotating a distal end of the second tibial prosthetic component to position a second axis defined by the distal end in a vertically-extending plane, and securing the second tibial prosthetic component to the post of the first tibial prosthetic component with the first axis and the second axis positioned in the vertically-extending plane.

In some embodiments, the method may further comprise advancing a stabilizer arm of the surgical instrument along the vertically-extending plane to position the stabilizer arm over the distal end of the second tibial prosthetic component and securing the second tibial prosthetic component to the stabilizer arm. The stabilizer arm may have an elongated body that extends along the vertically-extending plane.

Additionally, in some embodiments, the step of advancing the stabilizer arm along the vertically-extending plane to position the stabilizer arm over the distal end of the second tibial prosthetic component may include positioning the distal end of the second tibial prosthetic component in a channel defined in a proximal tip of the stabilizer arm.

In some embodiments, the method may further comprise positioning a tibial trial construct on the carrier. The tibial trial construct may comprise a base trial that defines a base axis and an offset trial that defines a stem axis that is offset from the base axis. The method may comprise advancing a stabilizer arm of the surgical instrument along the vertically-extending plane to engage the stabilizer arm with the tibial trial construct, locking the mounting platform to prevent rotation relative to the stabilizer arm, and removing the tibial trial construct from the carrier prior to positioning the first tibial prosthetic component on the carrier. The step of rotating the mounting platform of the surgical instrument may include rotating the carrier and the tibial trial construct to position the base axis and the stem axis in the vertically-extending plane.

According to another aspect, a method of assembling an orthopaedic prosthesis comprises aligning a prosthetic trial assembly with a surgical instrument that includes a mounting platform and a stabilizer arm. The prosthetic trial assembly comprises a prosthetic trial component that defines a first axis and an offset adaptor trial that defines a second axis that is offset from the first axis. The method also comprises positioning the prosthetic trial assembly on the mounting platform, rotating the mounting platform to position the first axis and the second axis in a plane extending vertically through the stabilizer arm, advancing the stabilizer arm along the vertically-extending plane to engage the stabilizer arm with the prosthetic trial assembly, locking the mounting platform to prevent rotation relative to the stabilizer arm, and positioning a prosthetic component on the mounting platform after removing the prosthetic trial assembly such that a third axis defined by a post of the prosthetic component is positioned in the plane. The prosthetic component has a size and a shape that matches a size and a shape of the prosthetic trial component. The method further comprises positioning on the post an offset adaptor including an end that defines a fourth axis that is offset from the third axis by an amount equal to the offset of the first axis and the second axis, rotating the end of the offset adaptor to position the fourth axis in the vertically-extending plane, and securing the offset adaptor to the prosthetic component with the third axis and the fourth axis positioned in the plane.

In some embodiments, the prosthetic component is a tibial prosthetic component and the prosthetic trial component is a tibial trial. In some embodiments, the prosthetic component is a femoral prosthetic component and the prosthetic trial component is a femoral trial.

According another aspect of the disclosure, a method of assembling an orthopaedic prosthesis comprises aligning a femoral trial construct with a surgical instrument that includes a mounting platform and a stabilizer arm. The femoral trial construct comprises a post that defines a first axis and an offset adaptor trial that defines a second axis that is offset from the first axis. The method also comprises positioning the femoral trial construct on the mounting platform, rotating the mounting platform to position the first axis and the second axis in a plane extending vertically through the stabilizer arm, advancing the stabilizer arm along the vertically-extending plane to engage the stabilizer arm with the femoral trial construct, and locking the mounting platform to prevent rotation relative to the stabilizer arm. The method further comprises positioning a femoral prosthetic component on the mounting platform after removing the femoral trial construct such that a third axis defined by a proximal post of the femoral prosthetic component is positioned in the plane, positioning a femoral offset adaptor on the proximal post, the femoral offset adaptor including a proximal end that defines a fourth axis that is offset from the third axis, and rotating the proximal end of the femoral offset adaptor to position the fourth axis in the vertically-extending plane. The method comprises securing the femoral offset adaptor to the femoral prosthetic component with the third axis and the fourth axis positioned in the plane.

In some embodiments, the method may comprise attaching a carrier to the mounting platform. The carrier may include a mounting plate and a post extending upwardly from the mounting plate. The step of positioning the femoral trial construct on the mounting platform may comprise advancing the femoral trial construct over the post to position the post in a passageway defined in the femoral trial construct.

Additionally, in some embodiments, the method may further comprise attaching to the carrier a shim sized to be positioned in an intercondylar notch defined in the femoral trial construct. The step of positioning the femoral trial construct on the mounting platform may further comprise advancing the femoral trial construct over the shim to position the shim in the intercondylar notch, and positioning the femoral trial construct on the mounting platform may include preventing a pair of condyles of the femoral trial construct from engaging the mounting plate of the carrier.

In some embodiments, the method may further comprise detaching the carrier from mounting platform, and attaching a second carrier to the mounting platform. The second carrier may include a second mounting plate and a second post extending upwardly from the second mounting plate. The second post may have a configuration different from the configuration of the first post. The method may also comprise attaching the shim the second carrier.

Additionally, in some embodiments, the step of positioning the femoral prosthetic component on the mounting platform after removing the femoral trial construct may include advancing the femoral prosthetic component over the second post to position the second post in a passageway defined in the femoral prosthetic component, advancing the femoral prosthetic component over the shim to position the shim in an intercondylar notch of the femoral prosthetic component, and preventing a pair of condyle surfaces of the femoral prosthetic component from engaging the second mounting platform of the second carrier.

In some embodiments, the method may comprise determining whether the femoral trial construct includes one of a first femoral trial component configured to be attached to a left femur and a second femoral trial component configured to be attached to a right femur, and selecting a femoral prosthetic component based on whether the femoral trial construct includes the first femoral trial component or the second femoral trial component. The step of attaching the second carrier to the mounting platform may include orienting the second carrier on the mounting platform based on the selected femoral prosthetic component, and attaching the shim to the second carrier may include attaching the shim to one of a first wall of the second carrier positioned on a first side of the second post and a second wall of the second carrier positioned on a second side of the second post based on the selected femoral prosthetic component.

In some embodiments, the step of positioning the femoral prosthetic component on the mounting platform may include orienting the femoral prosthetic component such that the third axis extends at an orthogonal angle relative to the mounting platform. The femoral prosthetic component may include a pair of condyles and a box structure that connects the pair of condyles. The box structure may include a planar proximal surface that extends at a non-orthogonal angle relative to the third axis.

In some embodiments, the method may further comprise securing a stem component to the proximal end of the femoral offset adaptor. In some embodiments, the method may further comprise advancing the stabilizer arm along the vertically-extending plane to engage the stabilizer arm with the proximal end of the femoral offset adaptor after rotating the proximal end of the femoral offset adaptor to position the third axis in the vertically-extending plane.

Additionally, in some embodiments, the step of advancing the stabilizer arm along the vertically-extending plane to engage the stabilizer arm with the proximal end of the femoral offset adaptor includes positioning the proximal end of the femoral offset adaptor in a channel defined between a pair of proximal tips of the stabilizer arm. In some embodiments, the step of advancing the stabilizer arm along the vertically-extending plane to engage the stabilizer arm with the offset adaptor trial includes positioning the offset trial in the channel defined in the stabilizer arm.

In some embodiments, the method may further comprise securing the offset adaptor trial in the proximal tip of the stabilizer arm before locking the mounting platform to prevent rotation relative to the stabilizer arm. Additionally, in some embodiments, the method may further comprise aligning a visual marking on the offset adaptor trial with an alignment window defined in the stabilizer arm.

In some embodiments, the step of advancing the stabilizer arm along the vertically-extending plane to engage the stabilizer arm with the offset trial may further include aligning a pair of chamfered end surfaces of proximal tip with a sloped surface of the offset trial.

According to another aspect, a method of assembling an orthopaedic prosthesis comprises rotating a mounting platform of a surgical instrument about a vertically-extending axis, attaching a carrier to the mounting platform, attaching a shim to the carrier, and positioning a first femoral prosthetic component on the carrier. The first femoral prosthetic component including a pair of spaced apart condyles, an intercondylar notch sized to receive the shim, and a proximal post. The method may also comprise securing a second femoral prosthetic component to the proximal post of the first femoral prosthetic component.

In some embodiments, the second femoral prosthetic component may include an elongated stem component. In some embodiments, the second femoral prosthetic component includes a prosthetic sleeve having a stepped outer surface.

The second femoral prosthetic component may include an offset adaptor and an elongated stem component configured to be attached to a proximal end of the offset adaptor. Additionally, in some embodiments, the proximal post of the first femoral prosthetic component defines a first axis, and the step of securing the second femoral prosthetic component to the post of the first femoral prosthetic component may include rotating a proximal end of the offset adaptor to position a second axis defined by the proximal end in a vertically-extending plane, and securing the offset adaptor to the proximal post of the first femoral prosthetic component with the first axis and the second axis positioned in the vertically-extending plane.

In some embodiments, the method may further advancing a stabilizer arm of the surgical instrument along the vertically-extending plane to position the stabilizer arm over the proximal end of the offset adaptor and securing the offset adaptor to the stabilizer arm.

According to another aspect, the surgical instrument system for assembling an orthopaedic prosthesis for a patient's knee joint comprises a prosthetic component carrier configured to receive a prosthetic component of the orthopaedic prosthesis. In some embodiments, the prosthetic component carrier may include a mounting block and a post extending at a non-orthogonal angle relative to the mounting block. The post may include a distal end that is sized to be received in a passageway of a prosthetic femoral component.

In some embodiments, the prosthetic component carrier may include a first clamp plate and a second clamp plate that are moveable to grip a prosthetic tibial component between the first clamp plate and the second clamp plate.

In some embodiments, the surgical instrument system may further comprise a wrench including an open slot sized to receive a femoral sleeve configured to be coupled to the prosthetic femoral component. The open slot may be defined by a plurality of surfaces of the wrench. The wrench may also include a plurality of lobes extending from the surfaces into the open slot. Each lobe may be shaped to engage a surface of the femoral sleeve.

According to another aspect, the surgical instrument system for assembling an orthopaedic prosthesis for a patient's knee joint comprises a trial component carrier configured to receive a trial component corresponding to a prosthetic component of the orthopaedic prosthesis. In some embodiments, the trial component carrier may include a mounting block and a post extending at a non-orthogonal angle relative to the mounting block. The post may include a distal end that is sized to be received in a passageway of a femoral trial component corresponding to a femoral prosthetic component.

In some embodiments, the trial component carrier may include a first clamp plate and a second clamp plate that are moveable to grip a tibial trial component between the first clamp plate and the second clamp plate.

BRIEF DESCRIPTION OF THE DRAWINGS

The detailed description particularly refers to the following figures, in which:

FIG. 14 is an exploded perspective view of a femoral trial construct for use in trialing the femoral prosthesis system of FIG. 12;

FIG. 15 is a perspective view of a femoral broach;

DETAILED DESCRIPTION OF THE DRAWINGS

Figure 1:
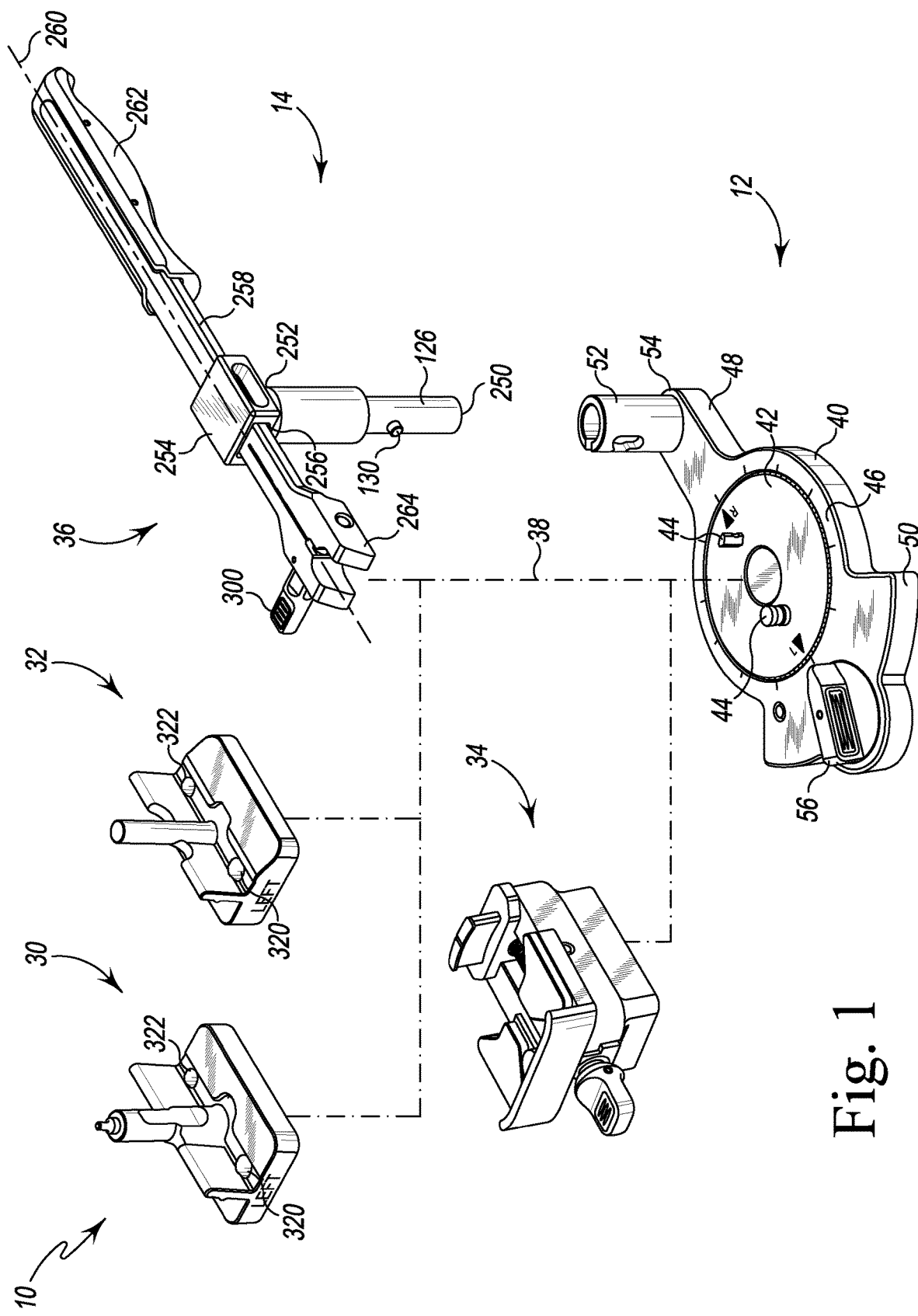
FIG. 1 is an exploded perspective view of an orthopaedic surgical instrument system for assembling an implantable orthopaedic prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an orthopaedic surgical instrument system 10 for use in selecting and assembling an orthopaedic prosthesis is shown. The surgical instrument system 10 includes an instrument base 12 and a number of modular instruments 14 that are selectively attached to the base to position a prosthetic femoral component 16 (see FIG. 12) or a prosthetic tibial component 18 (see FIG. 19) on the base 12. As described in greater detail below, some of the instruments 14 may be used to position a femoral trial component 20 (see FIG. 14) or a tibial trial component 22 (see FIG. 20) on the base 12 to assist the surgeon in assembling the prosthetic components. In the illustrative embodiment, the instrument system 10, prosthetic components 16, 18, and trial components 20, 22 form part of an orthopaedic system that may be used to replace a patient's knee joint. Although only a single size of each prosthetic component and each trial component is shown, it should be appreciated that the orthopaedic system may include multiple sizes of prosthetic components and trial components to fit the needs of various patients.

The modular instruments 14 of the system 10 include a femoral trial carrier 30 that is configured to mount the femoral trial component 20 on the instrument base 12. The instruments 14 also include a prosthetic femoral component carrier 32 that is configured to mount the prosthetic femoral component 16 on the instrument base 12, and a tibial component carrier 34 that, in the illustrative embodiment, is configured to mount either the prosthetic tibial component 18 or the tibial trial component 22 to the base 12. Each of the carriers 30, 32, 34 are sized to receive any size of prosthetic component or trial component in the orthopaedic system, as described in greater detail below. As shown in FIG. 1, the modular instruments 14 also include a stabilizing or support arm assembly 36, which can be used with the carriers 30, 32, 34 during prosthesis assembly.

The instrument base 12 includes a housing 40 configured to be positioned on a planar surface such as, for example, a table in an operating room. The instrument base 12 includes a platform 42 that is configured to rotate relative to the housing 40 about an axis 38. The platform 42 includes a pair of pins 44 that are sized to be selectively received in each of the carriers 30, 32, 34 to orient the carriers 30, 32, 34 on the instrument base 12.

As shown in FIG. 1, the platform 42 is positioned in a central section 46 of the housing 40. The housing 40 also includes an elongated plate 48 that extends outwardly from the central section 46 and an end plate 50 that is positioned opposite from the elongated plate 48. A mounting post 52 extends upwardly from an end 54 of the elongated plate 48 and is configured to receive the support arm assembly 36. The instrument base 12 also includes a locking mechanism 56 that is positioned in the end plate 50. As described in greater detail below, the locking mechanism 56 may be used to fix the platform 42 in a particular orientation about the axis 38 relative to the housing 40.

Figure 2:
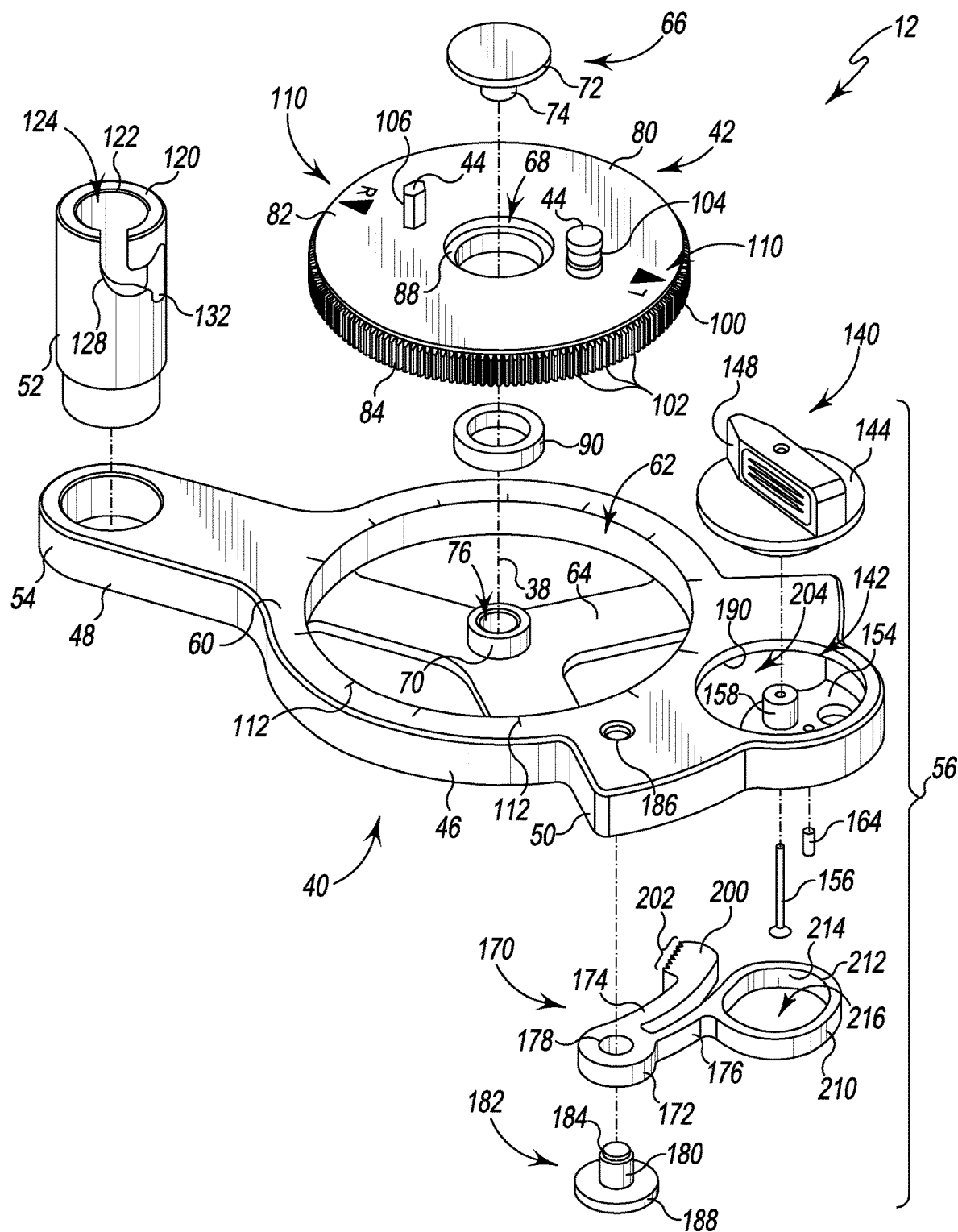
FIG. 2 is an exploded perspective view of an instrument assembly base of the orthopaedic surgical instrument system of FIG. 1.

Referring now to FIG. 2, the housing 40 includes a planar upper surface 60, and the central section 46 of the instrument base 12 includes a cavity 62 that is defined in the upper surface 60 and is sized to receive the platform 42. The instrument base 12 includes a frame 64 that is positioned at the bottom of the cavity 62 to support the platform 42. The platform 42 is attached to the housing 40 by a fastener plug 66, which extends through a central opening 68 defined in the platform 42 and is received in a mounting pin 70 that extends upwardly from the frame 64 at the center of the cavity 62.

In the illustrative embodiment, the plug 66 includes a head plate 72 and a shaft 74 that extends downwardly from the head plate 72. The shaft 74 is sized to be received in an aperture 76 defined in the mounting pin 70 to secure the plug 66 to the housing 40. As shown in FIG. 2, the platform 42 includes a disk 80 that has a planar upper surface 82, and the central opening 68 extends through the upper surface 82 to a lower surface 84 of the disk 80. A rim wall 88 extending into the central opening 68 engages the head plate 72 of the plug 66 to retain the platform 42 between the head plate 72 and the frame 64 of the housing 40. In the illustrative embodiment, the instrument base 12 also includes a spacer ring 90 that is positioned between the rim wall 88 and the mounting pin 70 to act as a bearing between the stationary pin 70 and the rotating platform 42. As shown in FIG. 2, the axis 38 about which the platform 42 is rotated extends through center of the central opening 68.

The disk 80 includes an outer annular wall 100 that extends from the upper surface 82 to the lower surface 84. The disk 80 also includes a plurality of gear teeth 102 that are defined in the outer wall 100 around the circumference of the disk 80. As described in greater detail below, the gear teeth 102 interact with the locking mechanism 56 to fix the mounting platform 42 in position relative to the housing 40. The mounting platform 42, plug 66, and spacer ring 90, like the housing 40, are formed from materials that may be autoclaved such as, for example, stainless steel.

As described above, the mounting platform 42 also includes a pair of pins 44 that are sized to be selectively received in each of the carriers 30, 32, 34 to orient the carriers 30, 32, 34 on the instrument base 12. In the illustrative embodiment, the pins 44 extend upwardly from the upper surface 82 of the disk 80. The pins 44 include a generally cylindrical pin 104 that is positioned on one side of the opening 68 and a polygonal pin 106 that is positioned on the opposite side of the opening 68. The polygonal pin 106 has a width that is smaller than the diameter of the cylindrical pin 104. It should be appreciated that in other embodiments the pins may take different geometric shapes and may be sized differently to orient the carriers.

The platform 42 includes visual indicia 110 and the housing 40 includes visual indicia 112, which may be used during surgery to confirm the proper orientation and position of the instruments. In the illustrative embodiment, the indicia 110 on the platform 42 include arrows and letters ("L" corresponding to "Left" and "R" corresponding to "Right"). The indicia 112 on the housing 40 include indicator lines, and the arrows of indicia 110 may be aligned with the indicator lines to indicate the orientation and position of the instruments. In other embodiments, the indicia 110, 112 may include numbers or other indicators.

As described above, the instrument base 12 also includes a mounting post 52 that extends upwardly from an end 54 of the elongated plate 48. The mounting post 52 is configured to receive the support arm assembly 36. In the illustrative embodiment, the post 52 includes an upper end 120 and an opening 122 that is defined in the upper end 120. A central passageway 124 sized to receive a mounting shaft 126 of the support arm assembly 36 extends inwardly from the opening 122. The post 52 also includes an alignment slot 128 that extends from the upper end 120 and opens into the passageway 124. The alignment slot 128 is sized to receive an alignment tab 130 of the support arm assembly 36 and defines a twisting path for the alignment tab 130 that causes the support arm assembly 36 to rotate from an initial, insertion position to a final, assembled relative to the platform 42. In the final assembled position, the alignment tab 130 is retained in a lower pocket 132 of the alignment slot 128.

As described above, the instrument base 12 also includes a rotation locking mechanism 56 that is positioned in the end plate 50. Each of the components of the mechanism 56 is formed from a material such as, for example, stainless steel, which may be autoclaved so that the base 12 may be cleaned between surgeries. The locking mechanism 56 includes a user-operated knob 140 that is received in a cavity 142 defined in the upper surface 60 of the base housing 40. The knob 140 is operable to rotate relative to the base housing 40 and includes a main plate 144 and an elongated grip 146 that extends upwardly from the main plate 144. In the illustrative embodiment, the elongated grip 146 includes a pointed tip 148 that indicates whether the knob 140 is in a locked position or unlocked position. The pointed tip 148 may point to indicia on the housing 40 to indicate the locked or unlocked positions. The knob 140 also includes an oblong base 152 that extends downwardly from the main plate 144 and is received in the cavity 142.

Figure 3:
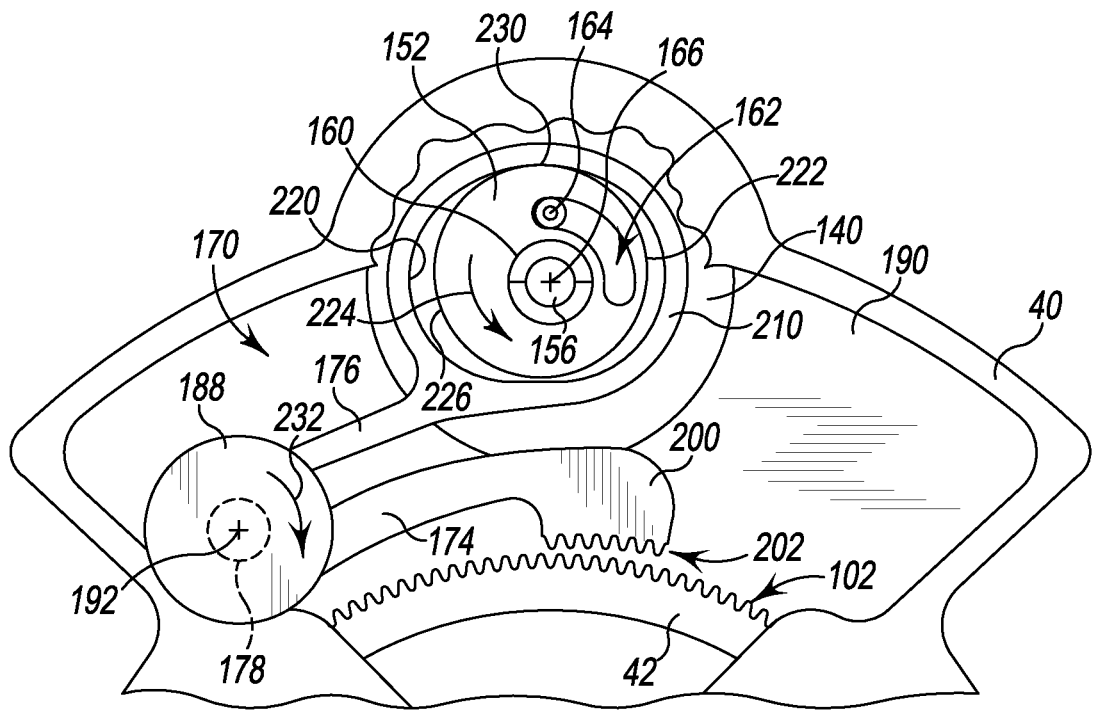
FIG. 3 is a bottom plan view showing the rotation locking mechanism of the instrument assembly base of FIG. 2 in an unlocked position.

In the illustrative embodiment, the base housing 40 includes a frame 154 that is positioned at the bottom of the cavity 142 to support the base 152 of the knob 140. The knob 140 is attached to the base housing 40 via a fastener 156, which extends through the frame 154. The fastener 156 extends through a cylindrical mounting pin 158 and is received in the oblong base 152 of the knob 140. As shown in FIG. 3, the fastener 156 is positioned in a bore 160 that is offset from the center of the oblong base 152. The bore 160 defines the axis of rotation 166 of the knob 140. The oblong base 152 also includes an arced channel or groove 162 that receives a guide pin 164 secured to the frame 154.

The pin 164 interacts with the groove 162 to limit the rotational movement of the knob 140, as described in greater detail below.

Returning to FIG. 2, the locking mechanism 56 also includes a clutch 170 that selectively engages the gear teeth 102 of the platform 42. The clutch 170 includes a mounting body 172 and a pair of arms 174, 176 that extend outwardly from the mounting body 172. In the illustrative embodiment, a central bore 178 extends through the mounting body 172 and is sized to receive a shaft 180 of a mounting peg 182. The shaft 180 includes a threaded distal end 184 that is threaded into an opening 186 defined in the base housing 40 to secure the mounting peg 182 to the housing 40. The mounting body 172 is retained between the head plate 188 of the mounting peg 182 and an inner surface 190 of the housing 40. The central bore 178 defines an axis of rotation 192 of the clutch 170.

The arm 174 of the clutch 170 extends from the mounting body 172 to a tip 200. The tip 200 includes a plurality of teeth 202 that are sized and shaped to interlock with the gear teeth 102 of the platform 42. As shown in FIG. 2, an elongated opening 204 is defined between the frame 154 and the inner surface 190 of the housing 40. The tip 200 extends through the opening 204 to engage the gear teeth 102 as the clutch 170 is rotated about the axis 192.

The other arm 176 of the clutch 170 extends from the mounting body 172 to a follower housing 210 sized to be positioned between the frame 154 and the main plate 144 of the knob 140. The follower housing 210 includes an upper opening 212 and an inner wall 214 that extends inwardly from the opening 212 to define an oblong slot 216 sized to receive the oblong base 152 of the knob 140. As shown in FIG. 3, the oblong slot 216 is larger than the oblong base 152. The inner wall 214 of the follower housing 210 includes a follower surface 220, and the oblong base 152 includes a cam surface 222 configured to selectively engage the follower surface 220 to rotate the clutch 170 about the axis 192.

Figure 4:
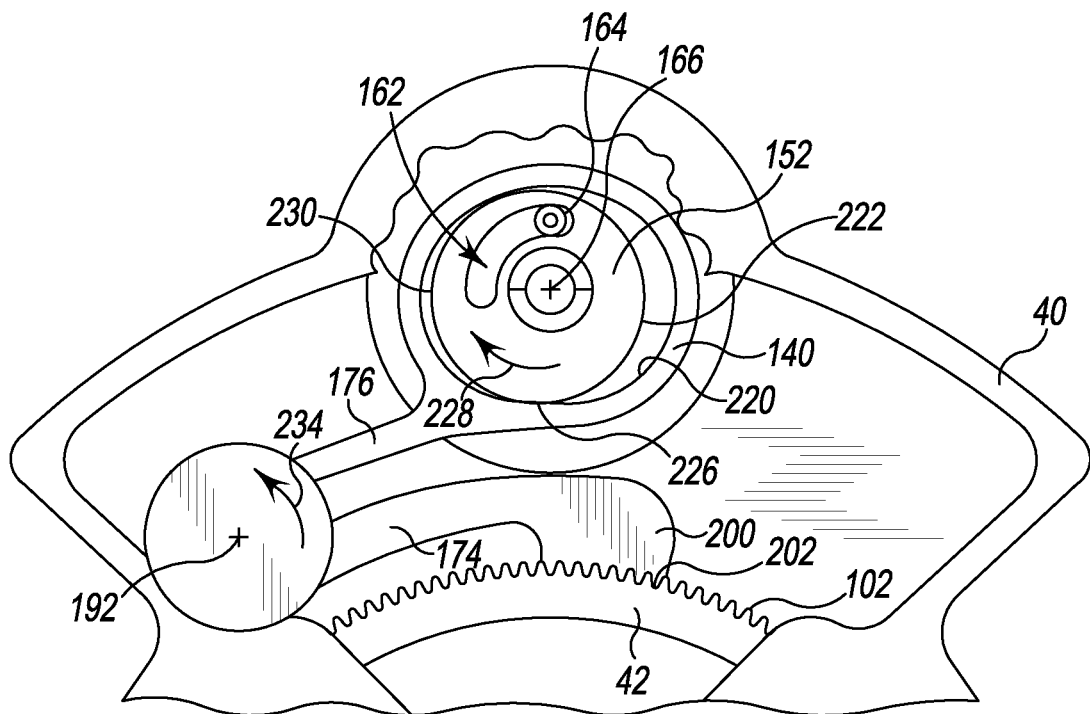
FIG. 4 is a view similar to FIG. 3 showing the rotation locking mechanism in a locked position.

To lock the platform 42 in an orientation relative to the base housing 40, a surgeon or other user may grasp the grip 146 of the knob 140 and rotate the knob 140 in the direction indicated by arrow 224 in FIG. 3. As the knob 140 is rotated, a section 226 of the cam surface 222 of the oblong base 152 that is initially out of contact with the follower surface 220 is advanced into engagement with the follower surface 220. As the section 226 of the cam surface 222 engages the follower surface 220, the clutch 170 is rotated about the axis 192 as indicated by arrow 232 to advance the teeth 202 into engagement with the teeth 102 of the platform 42, thereby locking the platform 42 in position relative to the housing 40. As shown in FIG. 4, the guide pin 164 moves from one end of the groove 162 to the opposite end of the groove 162 and prevents excessive rotation of the knob 140 (and hence the clutch 170).

To unlock the platform 42, the surgeon or other user may grasp the grip 146 of the knob 140 and rotate the knob 140 in the direction indicated by arrow 228 in FIG. 4. As the knob 140 is rotated, a section 230 of the cam surface 222 of the oblong base 152 that is out of contact with the follower surface 220 is advanced into engagement with the follower surface 220. As the section 230 of the cam surface 222 engages the follower surface 220, the clutch 170 is rotated about the axis 192 as indicated by arrow 234 to disengage the teeth 202 from the teeth 102 of the platform 42.

Returning to FIG. 1, the system 10 also includes the support arm assembly 36, which is configured to attached to the instrument base 12. The support arm assembly 36 includes the mounting shaft 126 that extends from a lower end 250, which is sized to be positioned in mounting post 52 to an upper end 252. A bracket 254 is secured to the upper end 252, and the bracket 254 includes a central passageway 256 sized to receive an elongated arm 258 of the support arm assembly 36. The elongated arm 258 extends along a longitudinal axis 260 from a handle end 262 to a tip 264. As described in greater detail below, the elongated arm 258 is configured to slide within the passageway 256 along the axis 260 to advance the tip 264 toward and away from the axis 38 of the instrument base 12. Additionally, the longitudinal axis 260 and the axis 38 are positioned in (and define) a vertically-extending orientation plane 270 (see FIG. 21), which is described in greater detail below.

Figure 5:
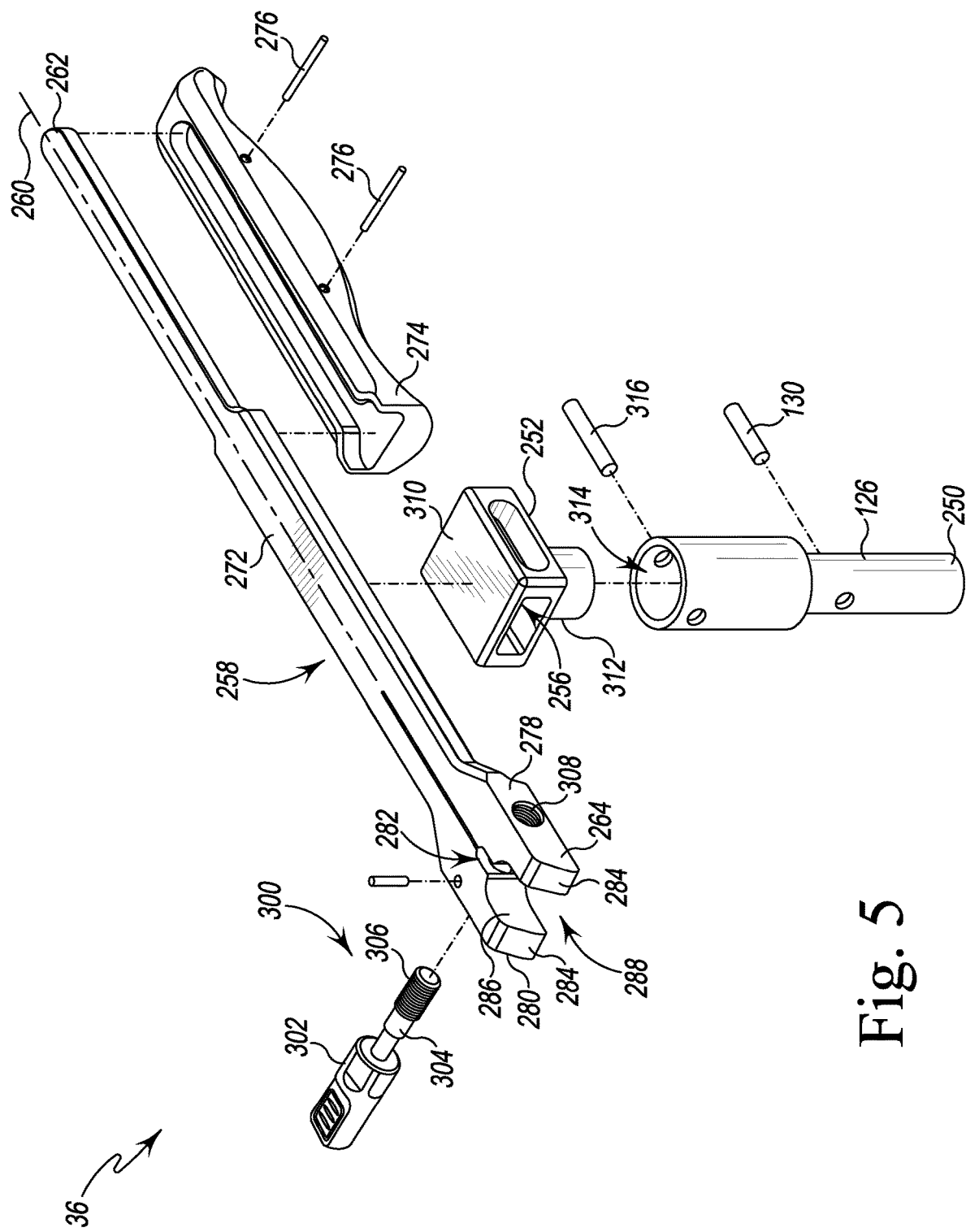
FIG. 5 is an exploded perspective view of a stabilizer arm of the orthopaedic surgical instrument system of FIG. 1.

Referring now to FIG. 5, the elongated arm 258 includes a main body 272 that extends from the handle end 262. In the illustrative embodiment, a handle grip 274 is attached to the main body 272 at the handle end 262 via a pair of pins 276. The elongated arm 258 also includes a pair of shafts 278, 280 that extend from an end of the main body 272 to the tip 264 of the elongated arm 258. The shafts 278, 280 are spaced apart from one another such that a channel 282 is defined between them. The channel 282 is wider at its proximal end 288 at the tip 264 and narrower near the elongated arm 258. As described in greater detail below, the channel 282 is sized to receive the offset adaptors of the trial component assemblies and prosthetic component assemblies.

Each shaft 278, 280 includes a chamfered end wall 284, which define the tip 264 of the elongated arm 258, and an inner wall 286 that faces the other shaft. The inner walls 286 of the shafts 278, 280 cooperate to define the proximal end 288 of the channel 282.

In the illustrative embodiment, the support arm assembly 36 includes a tightening mechanism 300 that may be operated to narrow the proximal end 288 of the channel 282 by pulling the shafts 278, 280 closer together. The tightening mechanism 300 includes a user-operated knob 302 and an elongated shaft 304 extending from the knob 302. The elongated shaft 304 extends through a bore (not shown) defined in the shaft 280 to a threaded end 306, which is received in a threaded bore 308 defined in the shaft 278.

As shown in FIG. 5, the bracket 252 of the support arm assembly 36 includes an upper housing 310 and a stem 312 that extends from the upper housing 310. The stem 312 is sized to be received in a passageway 314 defined in the mounting shaft 126. In the illustrative embodiment, the stem 312 is secured to the shaft 126 via a pin 316. The upper housing 310 includes the central passageway 256 through which the elongated arm 258 extends. It should be appreciated that each of the components of the support arm assembly 36 is formed from a material such as, for example, stainless steel, which may be autoclaved so that the support arm assembly 36 may be cleaned between surgeries.

Returning to FIG. 1, the system 10 also includes a femoral trial carrier 30, a prosthetic femoral component carrier 32, and a tibial component carrier 34 that are configured to be selectively mounted on the platform 42 of the instrument base 12. In other words, each of the carriers 30, 32, 34 is configured to be mounted on the platform 42 in place of any of the other carriers 30, 32, 34. Each of the carriers 30, 32, 34 includes a pair of orientation holes 320, 322 that are sized to receive the pins 104, 106, respectively, of the platform 42 to orient and attach the carriers 30, 32, 34 to the platform 42. In the illustrative embodiment, each of the orientation holes 320, 322 is cylindrical but the orientation hole 320 has a larger diameter than the orientation hole 322 such that the carriers 30, 32, 34 are configured to mounted on the platform 42 in only a single orientation. It should be appreciated that each of the carriers 30, 32, 34 is formed from a material such as, for example, stainless steel, which may be autoclaved so that the carriers 30, 32, 34 may be cleaned between surgeries.

Figure 6:
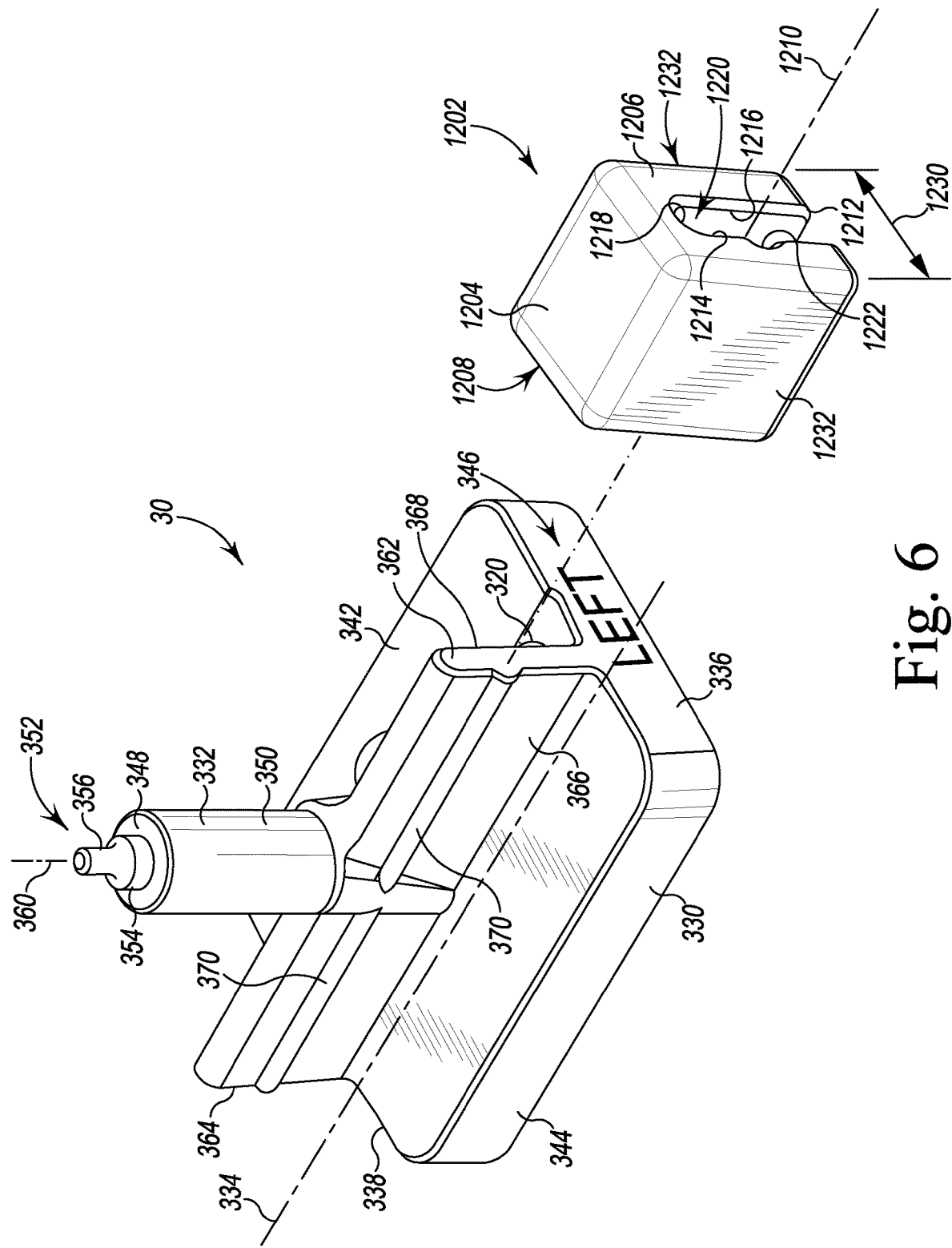
FIG. 6 is a perspective view of a femoral trial carrier and a shim of the orthopaedic surgical instrument system of FIG. 1.

Referring now to FIG. 6, the femoral trial carrier 30 includes a mounting block 330 and a post 332 that extends upwardly from the mounting block 330. The mounting block 330 is elongated and extends along a longitudinal axis 334 from a longitudinal end 336 to its opposite longitudinal end 338. The block 330 includes a planar bottom surface 340 and a top surface 342 that is positioned opposite the bottom surface 340. An outer wall 344 connects the top surface 342 to the bottom surface 340. In the illustrative embodiment, the outer wall 344 has visual indicia 346 at each end 336, 338 to indicate the orientation of the mounting block 330. The visual indicia 346 includes letters in the illustrative embodiment ("Left" on the end 336 and "Right" on the end 338).

Figure 7:
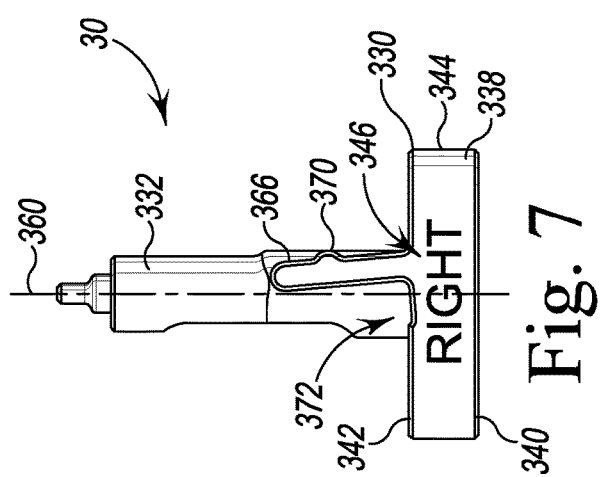
FIG. 7 is a side elevation view of the femoral trial carrier of FIG. 6.

The post 332 extends from the top surface 342 of the block 330 to an upper end 348. In the illustrative embodiment, the post 332 includes a cylindrical outer surface 350, and an alignment pin 352 extends outwardly from the upper end 348. The alignment pin 352 is shaped to be received in a bore 732 (see FIG. 23) of the femoral trial component 20. As shown in FIGS. 6-7, the alignment pin 352 includes a rounded base 354 and extends to a narrow tip 356. The post 332 extends along a longitudinal axis 360 extending through the tip 356. The axis 360 (and hence the post 332) extends at an orthogonal angle relative to the top surface 342 of the block 330.

The femoral trial carrier 30 also includes a pair of walls 362, 364 extending upward from the top surface 342 of the block 330 on opposite sides of the post 332. In the illustrative embodiment, the walls 362, 364 extend at a non-orthogonal angle relative to the top surface 342. Each wall 362, 364 is connected to the post 332 and includes planar outer surfaces 366, 368 that extend to the ends 336, 338 of the carrier 30. A rib 370 is formed on the outer surface 366 of each of the walls 362, 364. As shown in FIG. 6, the ribs 370 extend parallel to the longitudinal axis 334.

As described above, the carrier 30 includes a pair of orientation holes 320, 322 that are sized to receive the pins 104, 106, respectively, of the platform 42 to orient and attach the carrier 30 to the platform 42. In the illustrative embodiment, the holes 320, 322 extend through the block 330 and have upper openings positioned in a channel 372 defined in the top surface 342 next to the walls 362, 364.

Figure 8:
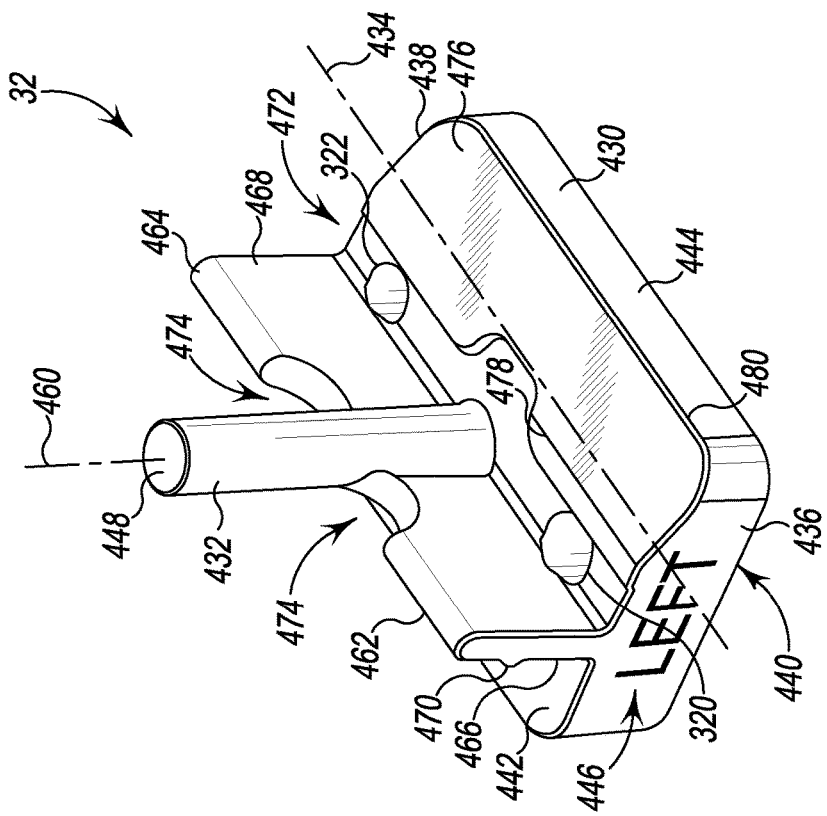
FIG. 8 is a perspective view of a femoral component carrier of the orthopaedic surgical instrument system of FIG. 1.

Referring now to FIG. 8, the prosthetic femoral component carrier 32 includes a mounting block 430 and a post 432 that extends upwardly from the mounting block 430. The mounting block 430 is elongated and extends along a longitudinal axis 434 from a longitudinal end 436 to its opposite longitudinal end 438. The block 430 includes a planar bottom surface 440 and a top surface 442 that is positioned opposite the bottom surface 440. An outer wall 444 connects the top surface 442 to the bottom surface 440. In the illustrative embodiment, the outer wall 444 has visual indicia 446 at each end 436, 438 to indicate the orientation of the mounting block 430. The visual indicia 446 includes letters in the illustrative embodiment ("Left" on the end 436 and "Right" on the end 438).

Figure 9:
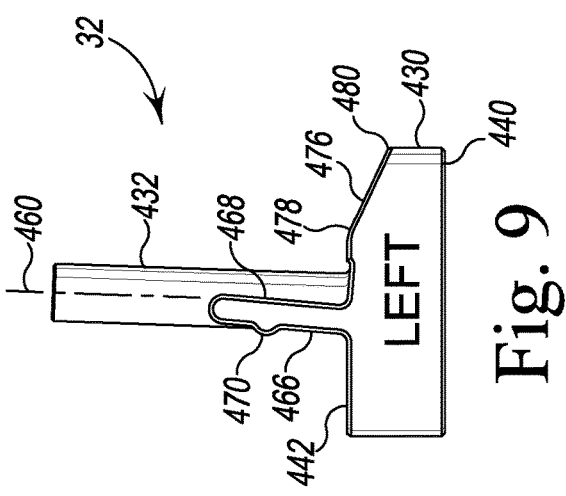
FIG. 9 is a side elevation view of the femoral prosthetic component carrier of FIG. 8.

The post 432 extends from the top surface 442 of the block 430 to an upper end 448. In the illustrative embodiment, the post 432 includes a cylindrical outer surface 450. The post 432 extends along a longitudinal axis 460, and the upper end 448 is sized to be received in a bore 622 (see FIG. 31) of the prosthetic femoral component 16. In the illustrative embodiment, the post 432 extends at a non-orthogonal angle relative to the top surface 442 of the block 430, as shown in FIG. 9.

The femoral component carrier 32 also includes a pair of walls 462, 464 extending upward from the top surface 442 of the block 430 on opposite sides of the post 432. In the illustrative embodiment, the walls 462, 464 extend parallel to the post 432. Each wall 462, 464 is connected to the post 432 and includes planar outer surfaces 466, 468 that extend to the ends 436, 438 of the carrier 32. A rib 470 is formed on the outer surface 466 of each of the walls 462, 464. As shown in FIG. 8, the ribs 470 extend parallel to the longitudinal axis 434.

As described above, the carrier 32 includes a pair of orientation holes 320, 322 that are sized to receive the pins 104, 106, respectively, of the platform 42 to orient and attach the carrier 32 to the platform 42. In the illustrative embodiment, the holes 320, 322 extend through the block 430 and have upper openings positioned in a channel 472 defined in the top surface 442 next to the walls 462, 464.

As shown in FIG. 8, the walls 462, 464 include relief slots 474 extending through the surfaces 466, 468 adjacent the post 432. Additionally, as shown in FIG. 9, the top surface 442 of the block 430 includes a section 476 positioned opposite the rib 470 that extends from an inner edge 478 to an outer edge 480. The section 476 extends at a non-orthogonal angle relative to the bottom surface 440 such that the outer edge 480 is closer to the bottom surface 440 than the inner edge 478.

Figure 10:
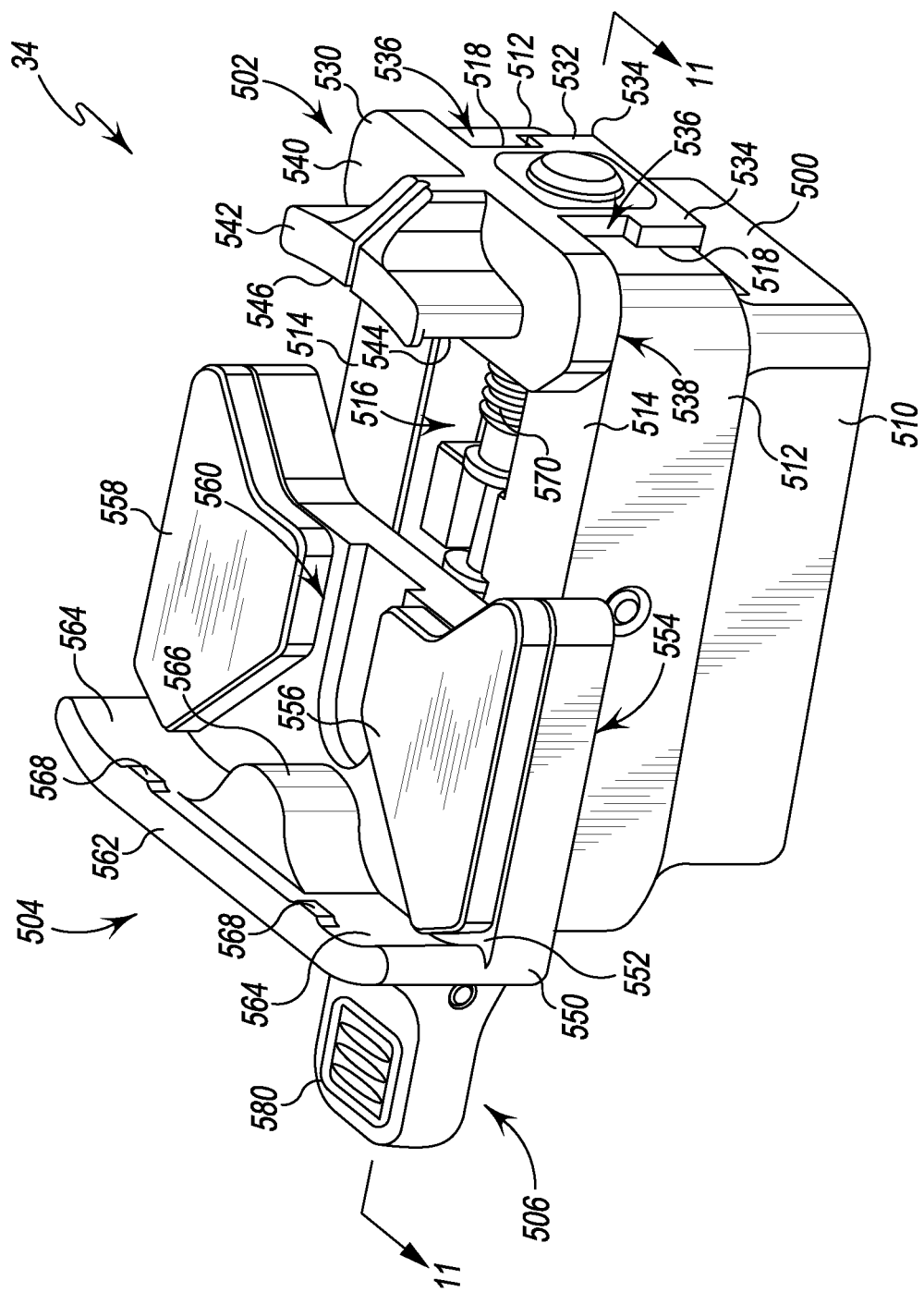
FIG. 10 is a perspective view of a tibial component carrier of the orthopaedic surgical instrument system of FIG. 1.

Referring now to FIG. 10, the system 10 also includes the tibial component carrier 34. As described above, the carrier 34 is configured to mount either the prosthetic tibial component 18 or the tibial trial component 22 to the base 12. The carrier 34 includes a mounting block 500 and a pair of clamp plates 502, 504 that are movably coupled to the mounting block 500. As described in greater detail below, the carrier 34 also includes a screw-type drive mechanism 506 operable to move the clamp plates 502, 504 to grip a prosthetic tibial component 18 or a tibial trial component 22 positioned on the plates 502, 504.

The mounting block 500 includes a base plate 510 and a pair of side walls 512 that extend upwardly from the base plate 510. Each side wall 512 includes a planar upper surface 514. A channel 516 extending through the mounting block 500 is defined between the base plate 510 and the side walls 512. As shown in FIG. 10, a flange 518 extends inwardly from each side wall 512 into the channel 516 to support the clamp plates 502, 504.

The clamp plate 502 of the carrier 34 includes an upper body 530 positioned above the side walls 512 and a lower body 532 extending downwardly from the upper body 530. The lower body 532 is received in the channel 516, and a pair of legs 534 extend outwardly from the lower body 532 to engage the lower surfaces of the flanges 518 of the mounting block 500. As shown in FIG. 10, the flanges 518 are positioned in channels 536 defined between the legs 534 and a planar lower surface 538 of the upper body 530. The upper body 530 also includes a top surface 540 that is positioned opposite the lower surface 538.

The clamp plate 502 includes a jaw 542 extending upwardly from the top surface 540. The jaw 542 has a curved inner wall 544 that is shaped to match the curvature of an anterior wall section 934 of the prosthetic tibial component 18 and the tibial trial component 22. The jaw 542 also includes an engagement tab 546 that extends outwardly from the curved inner wall 544.

As described above, the carrier 34 also includes a clamp plate 504 that is positioned opposite the clamp plate 502. The clamp plate 504 includes an upper body 550 positioned above the side walls 512 and a lower body 532 extending downwardly from the upper body 550. The lower body 532 has a configuration that is identical in relevant aspects to the lower body 532 of the clamp plate 502. The lower body 532 of the clamp plate 504 is received in the channel 516, and a pair of legs 534 extend outwardly from the lower body 532 to engage the lower surfaces of the flanges 518 of the mounting block 500.

The upper body 550 of the clamp plate 504 includes a top surface 552 that is positioned opposite a lower surface 554. The clamp plate 504 includes a pair of pads 556, 558 extending upwardly from the top surface 552. As shown in FIG. 10, a Y-shaped channel 560 is defined between pads 556, 558. The clamp plate 504 also includes a jaw 562 extending upwardly from the top surface 552. The jaw 562 has a pair of curved concave inner walls 564 and a curved convex inner wall 566 that is positioned between the walls 564. The walls 564, 566 that are shaped to match the curvature of posterior wall sections 936, 938 of the prosthetic tibial component 18 and the tibial trial component 22. The jaw 562 also includes engagement tabs 568 that extend outwardly from the curved inner walls 564.

Figure 11:
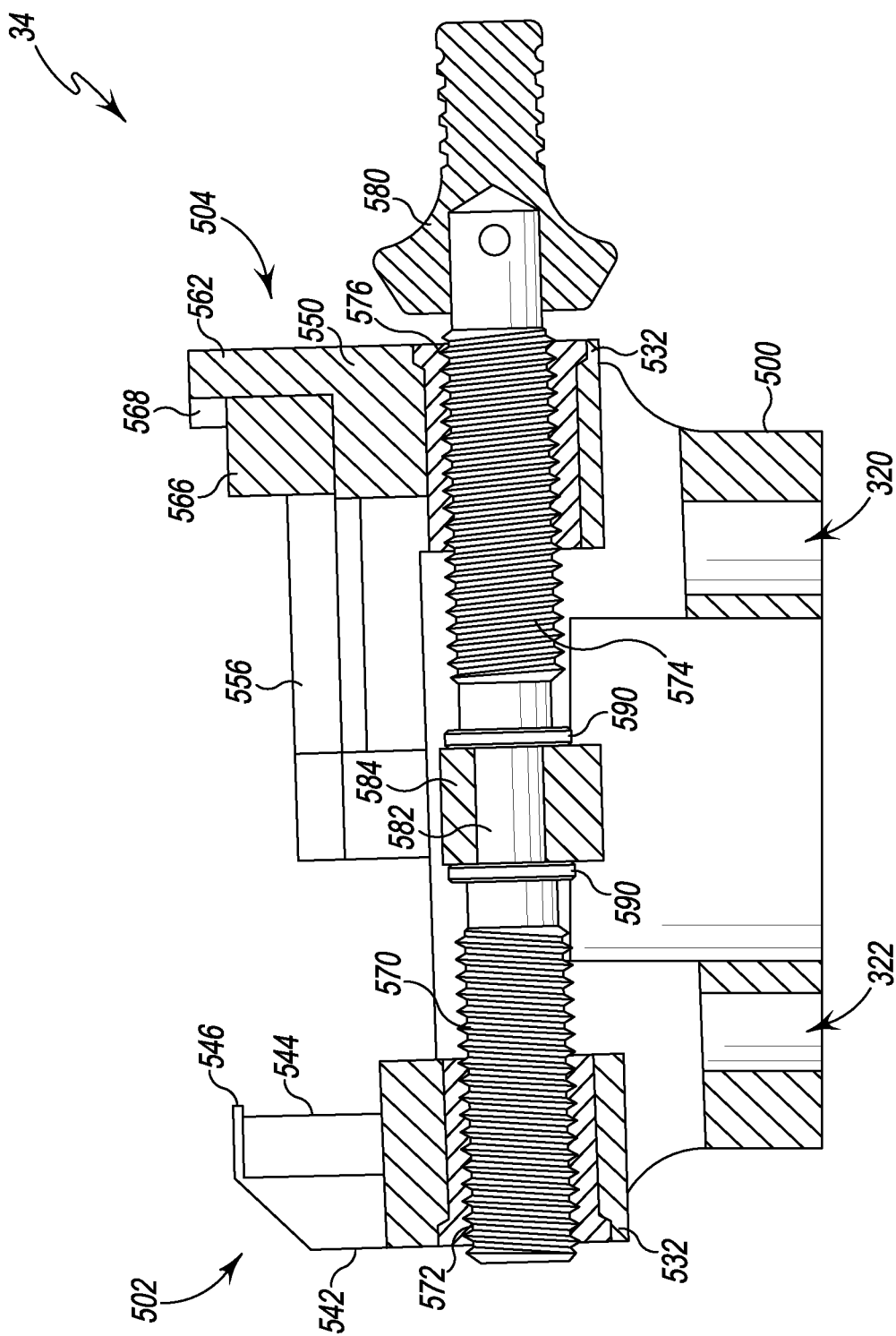
FIG. 11 is a cross-sectional elevation view of the tibial component carrier taken along the line 11-11 in FIG. 10.

As shown in FIG. 11, the carrier 34 includes a screw-type drive mechanism 506 that is operable to move the clamp plates 502, 504. In the illustrative embodiment, the mechanism 506 includes a threaded shaft 570 that is received in a threaded bore 572 defined in the lower body 532 of the clamp plate 502. The mechanism 506 includes a threaded shaft 574 that is received in a threaded bore 576 defined in the lower body 532 of the clamp plate 504. The mechanism 506 also includes a user-operated knob 580 connected to an end of the threaded shaft 574.

The shafts 570, 574 are connected via a rod 582 that extends through a brace 584 of the mounting block 500. As shown in FIGS. 10-11, the brace 584 extends from the side walls 512 of the mounting block 500 and is positioned in the channel 516. A pair of spacer rings 590 extend from the rod 582 on each side of the brace 584 to attach the mechanism 506 to the mounting block 500.

In use, a surgeon or other user may grasp the knob 580 and rotate the shafts 570, 574. The engagement between the shafts 570, 574 and the bores 572, 576 cause the clamp plates 502, 504 to advance along the shafts 570, 574. When the shafts 570, 574 are rotated clockwise, the clamp plates 502, 504 move toward one another; when the shafts 570, 574 are rotated counter-clockwise, the clamp plates 502, 504 move apart.

As described above, the instrument system 10 is configured for use in selecting and assembling an orthopaedic prosthesis. In the illustrative embodiment, the orthopaedic prosthesis includes the prosthetic femoral component 16 shown in FIGS. 12-13 and the prosthetic tibial component 18 shown in FIG. 16. Each of those components forms part of larger prosthesis systems that may include, for example, additional prosthetic femoral and tibial components of various sizes to fit the needs of patients with larger or smaller bones. The other prosthetic components may also be sized and shaped to be fitted on either the patient's left leg or the patient's right leg. Additionally, the systems may include other prosthetic components that attach to, or used in conjunction with, the prosthetic femoral component 16 and/or the prosthetic tibial component 18, as described in greater detail below.

Figures 12, 13:
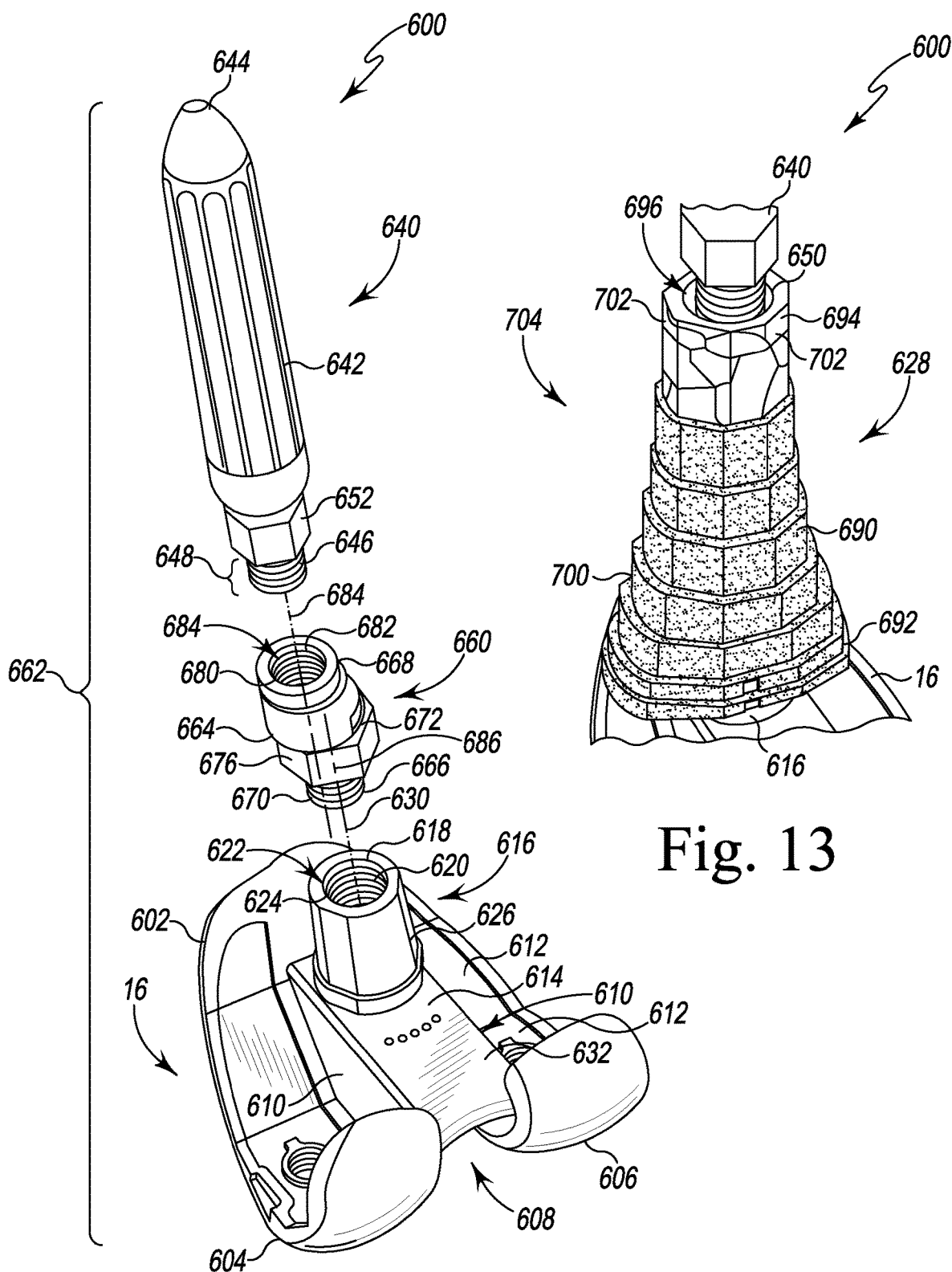
FIG. 12 is an exploded perspective view of a femoral prosthesis system.
FIG. 13 is a perspective view of a femoral sleeve component on a prosthetic femoral component.

Referring now to FIGS. 12-13, a femoral orthopaedic prosthesis system 600 includes the prosthetic femoral component 16 that is configured to be attached to a surgically-prepared distal end of a patient's femur. The femoral component 16 includes an anterior flange 602 and a pair of condyles 604, 606 extending posteriorly from the anterior flange 602. An intercondylar notch 608 is defined between the pair of condyles 604, 606. In the illustrative embodiment, the notch 608 is defined between a pair of side walls 610 that extend from proximal surfaces 612 of the anterior flange 602 and condyles 604, 606. A proximal wall 614 extends between the side walls 610 to enclose the proximal end of the notch 608.

The femoral component 16 also includes a post 616 that extends from the proximal wall 614. As shown in FIG. 12, the post 616 includes a proximal opening 618, and an inner wall 620 extends inwardly from the proximal opening 618 to define a bore 622 extending through the post 616 and the proximal wall 614 of the femoral component 16. In the illustrative embodiment, the inner wall 620 includes a threaded proximal section 624. The post 616 also includes a tapered outer surface 626 sized to receive a metaphyseal member such as, for example, a sleeve component 628 (see FIG. 13).

In the illustrative embodiment, the post 616 extends along a longitudinal axis 630, and the proximal wall 614 of the femoral component 16 includes a substantially planar surface 632. When the femoral component 16 is viewed in a coronal plane, a non-orthogonal angle is defined between the axis 630 and the substantially planar surface 632. It should be appreciated that the magnitude of the angle may vary in various embodiments and based on the size and configuration of the prosthesis assembly.

As shown in FIG. 12, the prosthesis system 600 also includes a stem component 640. The stem component 640 includes an elongated body 642 that extends from a distal end 644 to a proximal tip 646. A plurality of threads 648 are defined on the distal end 644, which, in some configurations of the prosthesis assembly, may engage the threaded proximal section 624 of the post 616 or the threaded proximal section 650 of the sleeve component 628 (see FIG. 13).

The prosthesis system 600 also includes an offset adaptor 660 that is configured to be secured to the femoral component 16 and the stem component 640 to form an offset femoral prosthesis assembly 662. The offset adaptor 660 includes a body 664 that extends from a distal end 666 to a proximal end 668 that is offset from the distal end 666, as shown in FIG. 12. The body 664 includes a threaded shaft 670 that extends proximally from the distal end 666 to a rim wall 672. The body 664 also includes a curved tapered surface 674 extends proximally from the rim wall 672. The threaded shaft 670 is configured to engage the threaded proximal section 624 of the post 616 to attach the adaptor 660 to the femoral component 16. The offset adaptor 660 also includes a locking nut 676 that is threaded onto the shaft 670, which may be operated to secure the offset adaptor 660 to the femoral component 16, as described in greater detail below.

The body 664 also includes an opening 680 that is defined in the proximal end 668. A threaded inner wall 682 extends inwardly from the opening 680 to define a threaded bore 684 sized to receive the threaded distal end 644 of the stem component 640. As shown in FIG. 12, the offset adaptor 660 defines a proximal axis 686 that extends through the threaded bore 684 and along the longitudinal axis of the stem component 640. The offset adaptor 660 also defines a distal axis 688 that extends through the threaded shaft 670 and is aligned with the longitudinal axis 630 of the post 616 of the femoral component 16. The axes 686, 688 extend parallel to, but are offset from, one another. In the illustrative embodiment, the body 664 is a single monolithic component such that the distal end 666 and the proximal end 668 are fixed relative to one another.

As shown in FIG. 13, the sleeve component 628 includes a stepped outer wall 690 that extends from a distal end 692 to a proximal end 694. The component 628 has an opening 696 defined in the proximal end 694 and an inner wall including the threaded proximal section 650 that extends inwardly from the opening 696. The component 628 also has a distal opening (not shown) sized to receive the post 616. It should be appreciated that the distal opening is defined by a tapered inner surface that corresponds to the tapered outer surface 626 of the post 616 such that the sleeve component 628 may be secured to the post 616 via a taper lock.

As shown in FIG. 13, the stepped outer wall 690 of the sleeve component 628 includes a porous section 700 configured to promote bone growth and support fixation of the sleeve component 628 in the patient's bone. The outer wall 690 also includes a number of planar surfaces 702 at the proximal end 694 that are shaped to receive a wrench head 1264 (see FIG. 37) to assist with assembly, as described in greater detail below. The stem component 640, femoral component 16, and sleeve component 628 form part of a femoral sleeve prosthesis assembly 704 that may be implanted in a patient's femur.

Referring now to FIGS. 14-15, a femoral trial system 710 includes the femoral trial component 20 that is configured to be temporarily attached to the distal end of a patient's femur to assist with the surgical preparation of the patient's femur to receive the prosthetic femoral component 16. The femoral trial component 20 includes an anterior flange 712 and a pair of condyles 714, 716 extending posteriorly from the anterior flange 712. An intercondylar notch 718 is defined between the pair of condyles 714, 716. In the illustrative embodiment, the configurations of the flange 712, the condyles 714, 716, and the intercondylar notch 718 match the configurations of the corresponding structures in the prosthetic femoral component 16. It should be appreciated that in other embodiments the femoral trial component may include one or more cutting guides that extend through the anterior flange 712 and/or the condyles 714, 716.

In the illustrative embodiment, the notch 718 is defined between a pair of side walls 720 that extend from proximal surfaces 722 of the anterior flange 712 and condyles 714, 716. A proximal wall 724 extends between the side walls 720 to enclose the proximal end of the notch 718. The femoral trial component 20 also includes a boss 726 that extends from the proximal wall 724, which is configured to receive an offset adaptor 770.

The boss 726 includes a planar proximal surface 728, and a pair of alignment pins 730 extend outwardly from the surface 728. A bore 732 extends through the boss 726 and opens into the intercondylar notch 718. The bore 732 is sized to permit a fastener such as, for example, bolt 734 to pass through the femoral trial component 20 and engage the offset adaptor 770. In that way, the femoral trial component 20 and the offset adaptor 770 may be secured together via the bolt 734.

In the illustrative embodiment, the boss 726 extends along a longitudinal axis 740, and the proximal wall 724 of the femoral component 16 includes a substantially planar surface 742. When the femoral component 16 is viewed in a coronal plane, a non-orthogonal angle is defined between the axis 740 and the substantially planar surface 742. It should be appreciated that the magnitude of the angle may vary in various embodiments and based on the size and configuration of the prosthesis assembly.

As shown in FIG. 14, the trial system 710 also includes a stem component 750. The stem component 750 includes an elongated body 752 that extends from a proximal tip 754 to a distal end 756. A plurality of threads 758 are defined on the distal end 756.

The trial system 710 also includes an offset adaptor 770 that is configured to be secured to the femoral trial component 20 and the stem component 750 to form an offset femoral trial construct 772. The offset adaptor 770 includes a two-piece body 774 that extends from a distal end 776 to a proximal end 778 that is offset from the distal end 776, as shown in FIG. 14. In the illustrative embodiment, the body 774 includes a distal sleeve 780 that extends from the distal end 776 to a proximal sleeve 782. The proximal sleeve 782 is rotatively coupled to the distal sleeve 780 to permit the surgeon to adjust the orientation of the femoral trial component 20 relative to the stem component 750 to find the optimum position on the patient's bone for the femoral offset prosthesis 662. The distal sleeve 780 includes a passageway 784 that extends inwardly from the distal end 776 to a threaded aperture (not shown) in the proximal sleeve 782. The threaded aperture is sized to receive the threaded end of the bolt 734 to secure the adaptor 770 to the femoral trial component 20. As shown in FIG. 14, the proximal sleeve 782 also includes a curved tapered surface 786 that connects the wider base of the proximal sleeve 782 to the more narrow proximal end 778.

The body 774 also includes an opening 790 that is defined in the proximal end 778. A threaded inner wall 792 extends inwardly from the opening 790 to define a threaded bore 794 sized to receive the threaded distal end 756 of the stem component 750. As shown in FIG. 14, the offset adaptor 770 defines a proximal axis 796 that extends through the threaded bore 794 and along the longitudinal axis of the stem component 750. The offset adaptor 770 also defines a distal axis 798 that is aligned with the longitudinal axis 740 of the boss 726 of the femoral trial component 20. The axes 796, 798 extend parallel to, but are offset from, one another by the same amount as the axes 686, 688 in the prosthesis assembly 662.

Referring now to FIG. 15, the femoral trial system 710 also includes a femoral broach 800 that has a plurality of cutting teeth 802 configured to remove portions of the patient's bone to prepare the bone to receive the femoral sleeve component 628. The cutting teeth 802 are formed in a stepped outer wall 804 having a configuration that corresponds to the stepped outer wall 690 of the femoral sleeve component 628. The broach 800 has an opening 806 defined in its proximal end 808 and a threaded inner wall 810 shaped to receive the threaded distal end 756 of the stem component 750. In the illustrative embodiment, the broach 800 includes a distal opening sized to receive the pins 730 of the femoral trial component 20. The broach 800 also includes threads (not shown) configured to engage the threaded end of the bolt 734 to secure the broach 800 to the femoral trial component 20.

Figure 16:
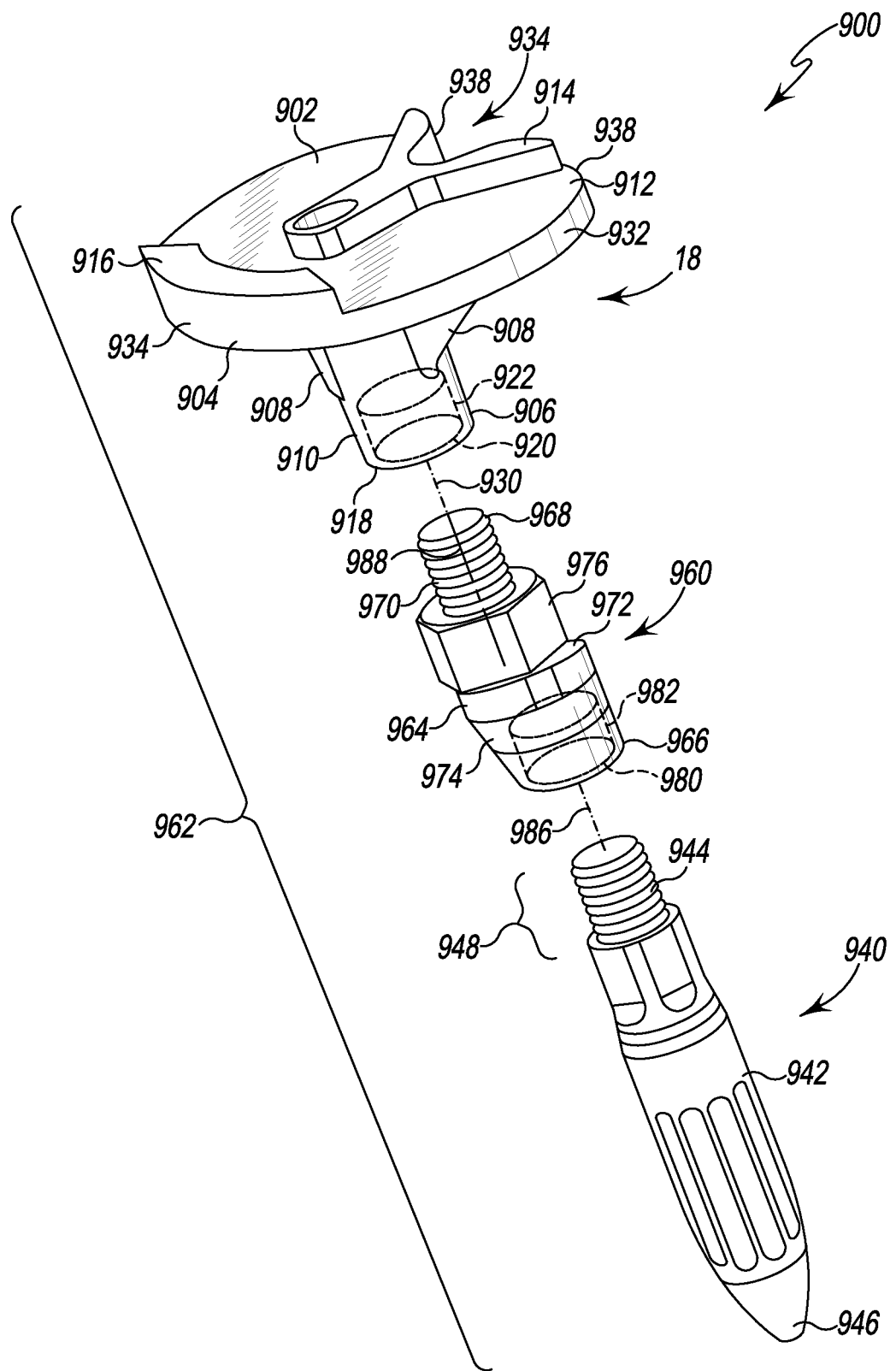
FIG. 16 is an exploded perspective view of a tibial prosthesis system.

Referring now to FIG. 16, a tibial orthopaedic prosthesis system 900 includes the prosthetic tibial component 18 that is configured to be attached to a surgically-prepared proximal end of a patient's tibia. The tibial component 18 includes a tibial tray 902 configured to receive a polymer insert or bearing (not shown) for articulation with the condyles 604, 606 of the prosthetic femoral component 602. The tray 902 includes a platform 904 and a distal stem post 906 extending from the platform 904. A pair of keels 908 extend between the outer surface 910 of the distal stem 906 and the platform 904. The platform 904 has a planar proximal surface 912 positioned opposite the distal stem post 906 and keels 908. The tibial tray 902 also includes a posterior buttress 914 that extends outwardly from the planar proximal surface 912. In the illustrative embodiment, the posterior buttress 914 is Y-shaped. The tibial tray 902 also includes an anterior buttress 916 that is spaced apart from the posterior buttress 914, as shown in FIG. 16.

The stem post 906 extends to a distal end 918. An opening 920 is defined in the distal end 918, and a passageway 922 extends inwardly from the opening 920. In the illustrative embodiment, threads (not shown) line the distal part of the passageway 922. The stem post 906 extends along a longitudinal axis 930. As shown in FIG. 16, the stem post 906 is sized to enter a patient's intramedullary canal, and the platform 904 is sized to be positioned over the opening of the canal and engage the proximal surface of the patient's tibia. The platform 904 includes a curved outer wall 932 that has a convex anterior section 934 and a concave posterior section 936 defined between to convex sections 938. The geometry of the curved outer wall 932 is shaped to conform to the geometry of the surgically-prepared proximal surface of the patient's tibia.

As shown in FIG. 16, the prosthesis system 900 also includes a stem component 940. The stem component 940 includes an elongated body 942 that extends from a proximal end 944 to a distal tip 946. A plurality of threads 948 are defined on the proximal end 944, which, in some configurations of the prosthesis assembly, may engage the threads in passageway 922 of the post 906 of the tibial tray 902.

The prosthesis system 900 also includes an offset adaptor 960 that is configured to be secured to the tibial component 18 and the stem component 940 to form an offset tibial prosthesis assembly 962. The offset adaptor 960 includes a body 964 that extends from a distal end 966 to a proximal end 968 that is offset from the distal end 966, as shown in FIG. 16. The body 964 includes a threaded shaft 970 that extends proximally from the proximal end 968 to a rim wall 972. The body 964 also includes a curved tapered surface 974 extends distally from the rim wall 972. The threaded shaft 970 is configured to engage the threads in passageway 922 of the post 906 to attach the adaptor 960 to the tibial component 18. The offset adaptor 960 also includes a locking nut 976 that is threaded onto the shaft 970, which may be operated to secure the offset adaptor 960 to the tibial component 18, as described in greater detail below.

The body 964 also includes an opening 980 that is defined in the distal end 966. A bore 982 extends inwardly from the opening 980 and is sized to receive the threaded proximal end 944 of the stem component 940. A plurality of threads extend into the bore 982 and are configured to engage the threads 944 of the stem component 940. As shown in FIG. 16, the offset adaptor 960 defines a distal axis 986 that extends through the threaded bore 984 and along the longitudinal axis of the stem component 940. The offset adaptor 960 also defines a proximal axis 988 that extends through the threaded shaft 970 and is aligned with the longitudinal axis 930 of the post 906 of the tibial component 18. The axes 986, 988 extend parallel to, but are offset from, one another. In the illustrative embodiment, the body 964 is a single monolithic component such that the distal end 966 and the proximal end 968 are fixed relative to one another.

Figure 17:
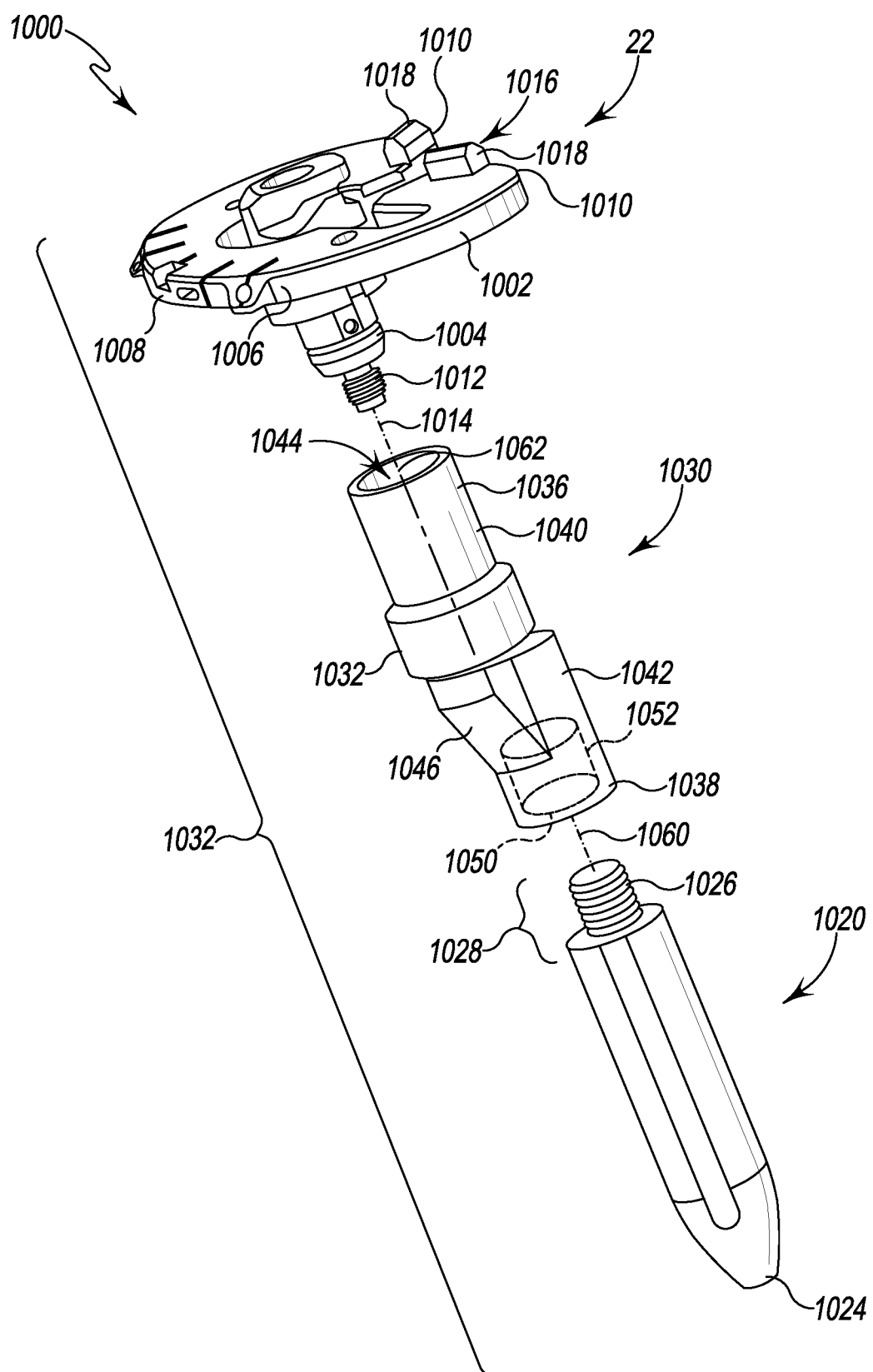
FIG. 17 is an exploded perspective view of a tibial trial construct for use in trialing the tibial prosthesis system of FIG. 16.

Referring now to FIG. 17, a tibial trial system 1000 includes the tibial trial component 22 that is configured to be temporarily attached to the proximal end of a patient's tibia to assist with the surgical preparation of the patient's tibia to receive the prosthetic tibial component 18. The tibial trial component 22 includes a base 1002 and a stem post 1004 extending distally from the base 1002. The base 1002 is configured to receive a tibial insert trial (not shown), which articulates with the condyles 714, 716 of the femoral trial 20. As shown in FIG. 17, the stem post 1004 is sized to enter a patient's intramedullary canal, and the base 1002 is sized to be positioned over the opening of the canal and engage the proximal surface of the patient's tibia. The base 1002 includes a curved outer wall 1006 that has a convex anterior section 1008 and a concave posterior section 1016 defined between to convex sections 1010. The geometry of the curved outer wall 1006 is shaped to match of the outer wall 932 of the tibial tray 902 such that the surgeon may utilize the trial 22 to confirm the tibial tray is the appropriate for the patient. The tibial trial 22 also includes a pair of alignment tabs 1018 that extend from the base 1002.

In the illustrative embodiment, the tibial trial component 22 also includes a retained bolt 1012 that is rotatively coupled to the base 1002. The bolt 1012 outwardly from the post 1004 along a longitudinal axis 1014.

As shown in FIG. 17, the trial system 1000 also includes a stem component 1020. The stem component 1020 includes an elongated body 1022 that extends from a distal tip 1024 to a proximal end 1026. A plurality of threads 1028 are defined on the proximal end 1026.

The trial system 1000 also includes an offset adaptor 1030 that is configured to be secured to the tibial trial component 22 and the stem component 1020 to form an offset tibial trial construct 1032. The offset adaptor 1030 includes a two-piece body 1034 that extends from a proximal end 1036 to a distal end 1038 that is offset from the proximal end 1036, as shown in FIG. 17. In the illustrative embodiment, the body 1034 includes a proximal sleeve 1040 that extends from the proximal end 1036 to a distal sleeve 1042. The distal sleeve 1042 that is rotatively coupled to the proximal sleeve 1040 to permit the surgeon to adjust the orientation of the tibial trial component 22 relative to the stem component 1020 to find the optimum position on the patient's bone for the tibial offset prosthesis 962. The proximal sleeve 1040 includes a passageway 1044 that extends inwardly from the proximal end 1036 to a threaded aperture (not shown) in the distal sleeve 1042. The threaded aperture is sized to receive the threaded end of the bolt 1012 to secure the adaptor 1030 to the tibial trial component 22. As shown in FIG. 17, the distal sleeve 1042 also includes a curved tapered surface 1046 that connects the wider base of the distal sleeve 1042 to the more narrow distal end 1038.

The body 1034 also includes an opening 1050 that is defined in the distal end 1038. A bore 1052 extends inwardly from the opening 1050. The bore 1052 is sized to receive the proximal end 1026 of the stem component 1020. A plurality of threads (not shown) are formed along the bore 1052 and are sized to engage the threads formed on the proximal end 1026 of the stem component 1020.

As shown in FIG. 17, the offset adaptor 1030 defines a distal axis 1060 that extends through the threaded bore 1052 and along the longitudinal axis of the stem component 1020. The offset adaptor 1030 also defines a proximal axis 1062 that is aligned with the longitudinal axis 1014 of the stem post 1004 of the trial 22. The axes 1060, 1062 extend parallel to, but are offset from, one another by the same amount as the axes 986, 988 in the prosthesis assembly 962.

Figure 18:
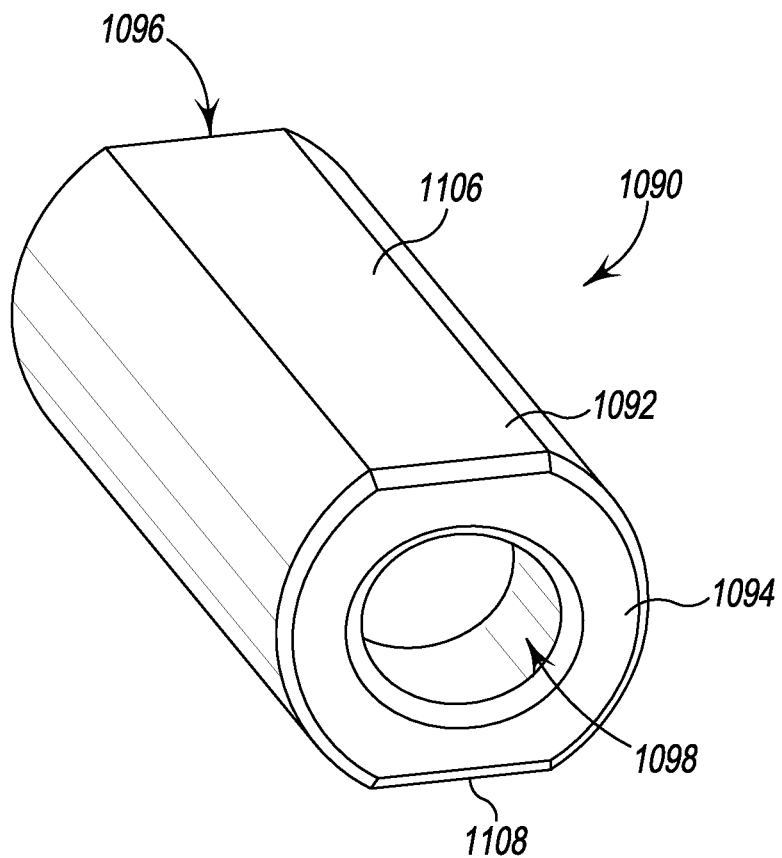
FIG. 18 is a perspective view of a sleeve impactor of the system of FIG. 1.
Figure 19:
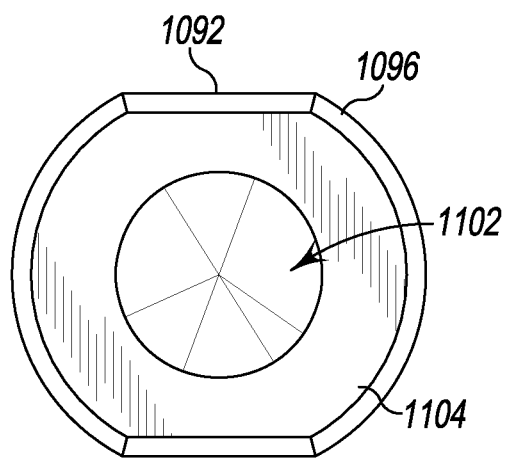
FIG. 19 is a side elevation view of the sleeve impactor of FIG. 18.
Figure 20:
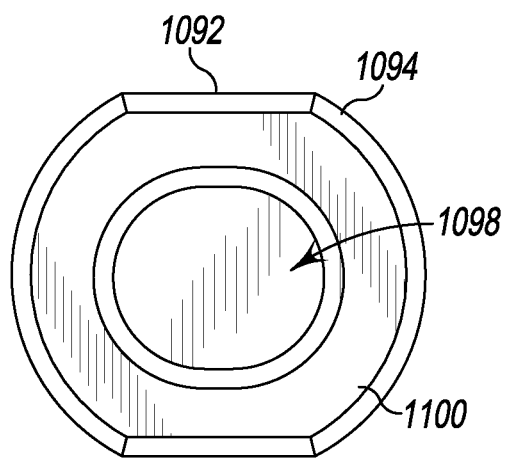
FIG. 20 is the side elevation view opposite the view of FIG. 19.

Referring now to FIGS. 18-20, the system 10 also includes a sleeve impactor 1090 for use in securing the femoral sleeve component 628 to the femoral component 16 is shown. The instrument 1090 is a single monolithic component formed from a metallic material such as, for example, stainless steel that can be autoclaved and sterilized for repeated use. The instrument 1090 includes an elongated body 1092 that extends from a femoral impaction end 1094 to a tibial impaction end 1096. In the illustrative embodiment, the femoral impaction end 1094 has an aperture 1098 defined in a surface 1100, as shown in FIGS. 18 and 20. The aperture 1098 is sized to be positioned over the proximal end 694 of the sleeve component 628. The aperture 1098 is oblong and oval in shape in the illustrative embodiment.

As shown in FIG. 19, the tibial impaction end 1096 has an aperture 1102 defined in a surface 1104. The aperture 1102 is sized to be positioned over the distal end 1292 of a tibial sleeve component 1286 (see FIG. 46), as described in greater detail below. The aperture 1102 is circular in shape in the illustrative embodiment and provides clearance with respect to the tibial base. The elongated body 1092 also has a pair of opposing planar surfaces 1106, 1108 to assist with supporting the instrument 1090 on the end of each sleeve component and prevent the instrument from rolling.

As described above, the orthopaedic surgical instrument system 10 may be used in a surgical procedure to assemble the prosthetic components described above in regard to FIGS. 12-17. FIGS. 21-47 illustrate various steps of a process for assembling an offset femoral prosthesis assembly 662 (FIGS. 21-32, a process for assembling a femoral sleeve prosthesis assembly 704 (FIGS. 34-37), and a process for assembling an offset tibial prosthesis assembly 962 (FIGS. 38-43). It should be appreciated that the processes and steps described are exemplary only and do not exclude additional steps consistent with this disclosure. Additionally, all of the steps are shown in reference to prostheses for use on only one knee of the patient; it should be appreciated that similar steps may be followed to assemble a prosthesis for the other knee.

During a surgical procedure, a surgeon may use a variety of cutting guide blocks, cutting tools, and other instruments to surgically prepare the patient's bones to receive, initially, the trial constructs 772, 1032. With the trial constructs attached to the patient's bones, the surgeon may analyze the fit of the trial constructs 772, 1032 on the patient's bones. The surgeon may also perform a trial reduction to evaluate the range of motion with an insert trial positioned between the constructs. In that way, the surgeon may determine the size of the tibial and femoral prostheses for implantation into the patient's bone, as well as determine the desired orientation and position of the tibial and femoral prosthetic components relative to their respective stem components.

During the trialing portion of the surgical procedure, the surgeon may rotate the femoral trial component 20 relative to the proximal axis 796 (and hence the stem component 750) of the offset adaptor 770. To do so, the distal sleeve 780 of the offset adaptor 770 is permitted to rotate relative to the proximal sleeve 782, which is fixed with the stem component 750 in the intramedullary canal of the patient's femur. When the surgeon determines that the femoral trial component 20 is properly positioned on the patient's femur, the surgeon may operate the bolt 734 to lock the distal sleeve 780 in position relative to the proximal sleeve 782, thereby locking the femoral trial component 20 in a desired orientation and position relative to the stem component 750.

Similarly, the surgeon may rotate the tibial trial component 22 relative to the distal axis 1060 (and hence the stem component 1020) of the offset adapter 1030 to change the position of the component 22 on the proximal end of the patient's tibia. To do so, the proximal sleeve 1040 of the offset adaptor 1030 is permitted to rotate relative to the distal sleeve 1042, which is fixed with the stem component 1020 in the intramedullary canal of the patient's tibia. When the tibial trial component 22 is properly positioned on the patient's tibia, the surgeon may operate the bolt 1012 to lock the proximal sleeve 1040 in position relative to the distal sleeve 1042, thereby locking the tibial trial component 22 in a desired orientation and position relative to the stem component 1020.

Referring now to FIGS. 21-32, the surgeon or other user may use the instrument system 10 to assemble an offset femoral prosthesis assembly 662 based on the configuration of the femoral trial construct 772 created as described above. In other words, the surgeon may utilize the instrument system 10 to secure the prosthetic femoral component 16 to the stem component 640 in a position and orientation that matches the desired orientation and position of the femoral trial component 20 determined during the surgical procedure. In that way, the assembled offset femoral prosthesis 662 replicates and matches the configuration of the femoral trial construct 772.

Figure 21:
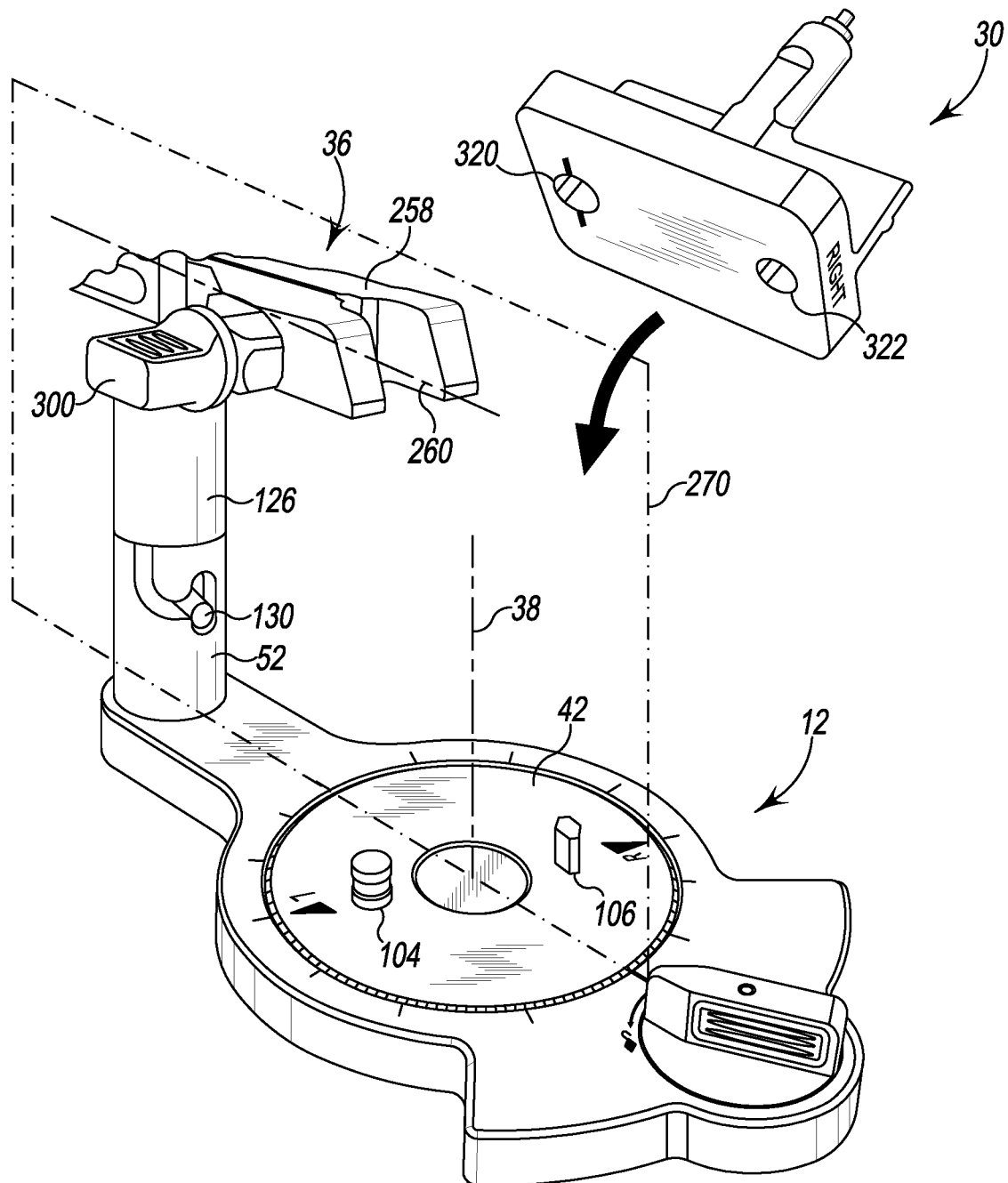
FIGS. 21-47 are illustrations of an exemplary technique for assembling various orthopaedic prostheses using the instrument system of FIG. 1.

To do so, the user may attach the appropriate modular instruments 14 to the instrument base 12, including the support arm assembly 36 and the femoral trial carrier 30. As shown in FIG. 21, the user may align the mounting shaft 126 of the support arm assembly 36 with the central passageway 124 defined in the mounting post 52 of the instrument base 12. Additionally, the alignment tab 130 of the support arm assembly 36 is aligned with the upper end of the alignment slot 128. The user may then advance the mounting shaft 126 into the central passageway 124 and the alignment tab 130 into the alignment slot 128. As the tab 130 advances downward and along the alignment slot 128, the elongated arm 258 is pivoted relative to the mounting post 52. When properly positioned on the mounting post 52, the elongated arm 258 is aligned with the vertically-extending orientation plane 270, as shown in FIG. 21.

To attach the femoral trial carrier 30 to the instrument base 12, the user may align the orientation holes 320, 322 with the cylindrical pin 104 and the polygonal pin 106, respectively, on the base platform 42. The user may then advance the carrier 30 over the pins 104, 106 to position the mounting block 330 of the carrier 30 on the platform 42. When the locking mechanism 56 is in the unlocked position, the user may rotate the platform 42 (and hence the femoral trial carrier 30) about the axis 38 to position the femoral trial carrier 30 as shown in FIG. 22.

Figure 22:
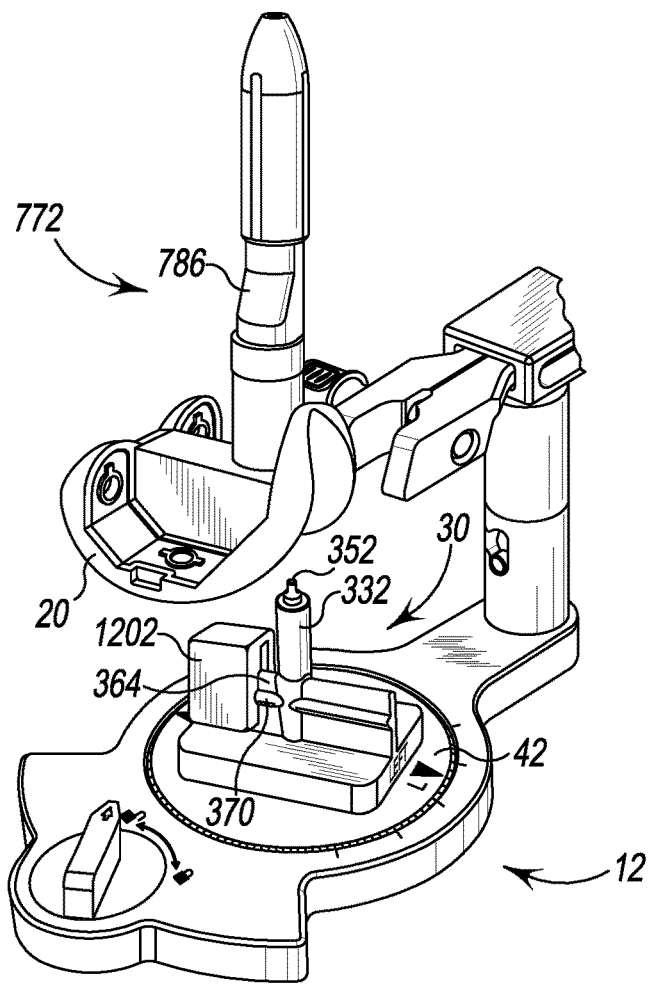
Figure 23:
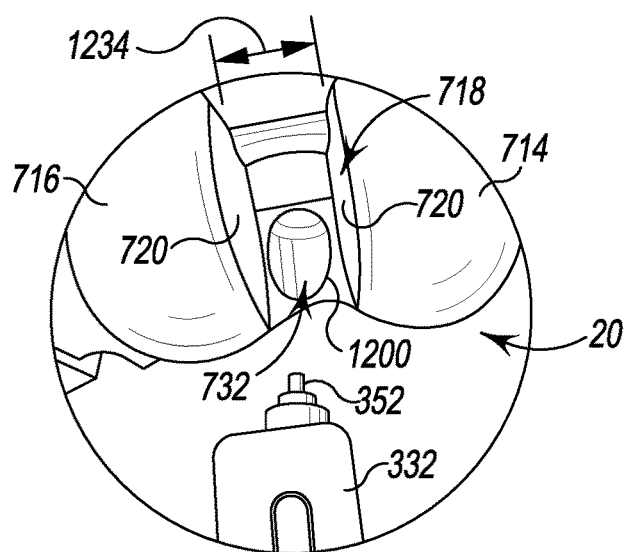

Referring now to FIGS. 22-23, the user may mount the femoral trial construct 772 on the femoral trial carrier 30. To do so, the user may position the femoral trial construct 772 over the alignment pin 352 and the post 332 of the femoral trial carrier 30. As shown in FIG. 23, the user aligns the distal opening 1200 of the bore 732 defined in the femoral trial component 20 with the alignment pin 352. The user may advance the femoral trial construct 772 downward such that the pin 352 and the upper end of the post 332 are received in the bore 732. The pin 352 is advanced into the socket (not shown) of the bolt 734 of the construct 772, and the wall 364 is positioned in the intercondylar notch 718 of the femoral trial component 20. As shown in FIG. 22, the surgical instrument system 10 also includes a support shim 1202 that is positioned on the wall 364 and is sized to be positioned the intercondylar notch 718 to support femoral trial component 20 on the carrier 30.

Returning to FIG. 6, the shim 1202 is shown in greater detail. The shim 1202 includes a body 1204 that extends from an end surface 1206 to an opposite end surface 1208 along a longitudinal axis 1210. The body 1204 has a lower opening 1212, which extends from the surface 1206 to the surface 1208 along the axis 1210. The shim 1202 includes a pair of inner side walls 1214, 1216 that extend upwardly from the opening 1212 to a curved base wall 1218. The walls 1214, 1216, 1218 define a channel 1220 in the shim 1202 that is sized to receive the walls 362, 364 of the carrier 30. In the illustrative embodiment, the shim 1202 also includes a groove 1222 defined in the side wall 1214. The groove 1222 is sized to receive the ribs 370 of the carrier 30 such that the shim 1202 may be mounted to each of the walls 362, 364 in only a single orientation.

The shim 1202 is formed from a material such as polymer in the illustrative embodiment. It has a width or thickness 1230 defined between a pair of planar side surfaces 1232. Returning to FIG. 23, the thickness 1230 of the shim 1202 is equal to about the width 1234 of the intercondylar notch 718. The width 1234 is defined between the side walls 720 of the femoral trial 20. It should be appreciated that the system 10 includes multiple shims of different thicknesses corresponding to different sizes of the femoral trial components 20 and prosthetic femoral components 16.

Figure 24:
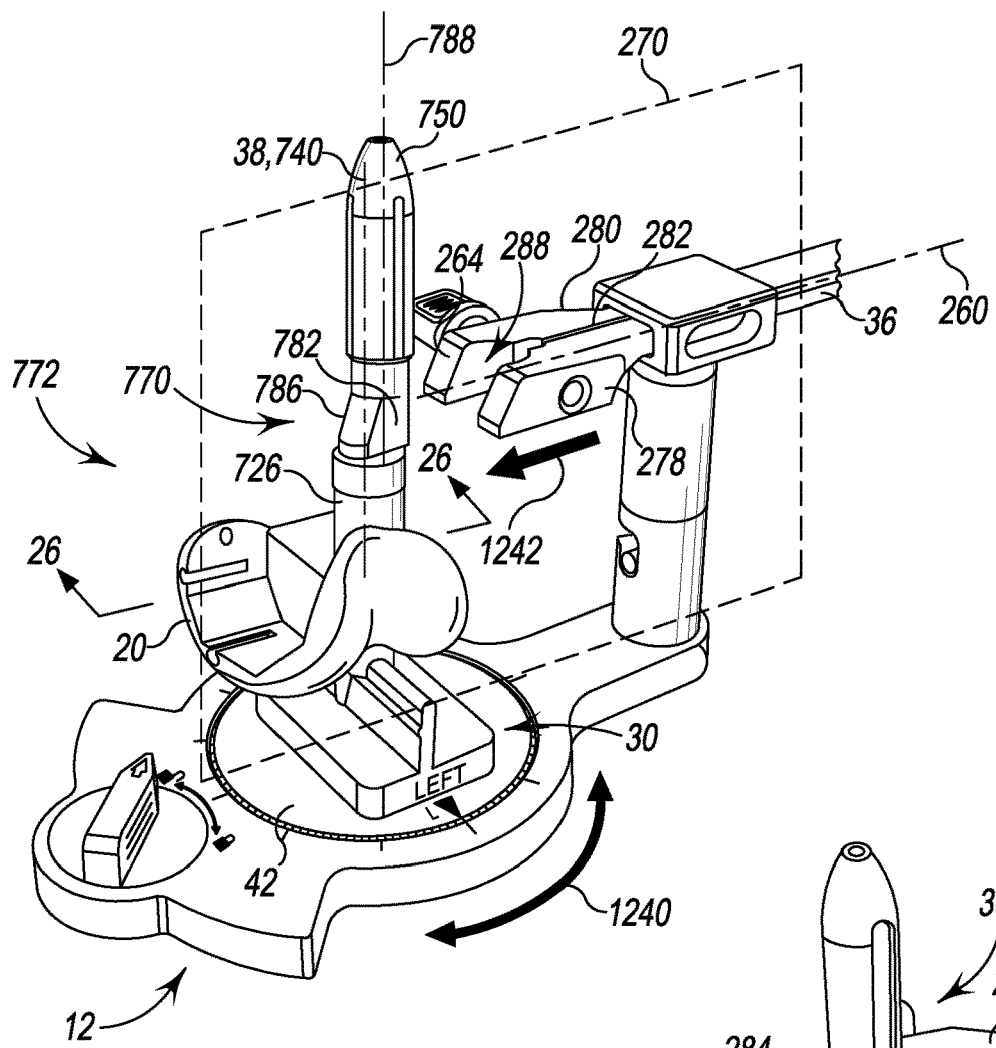
Figure 26:
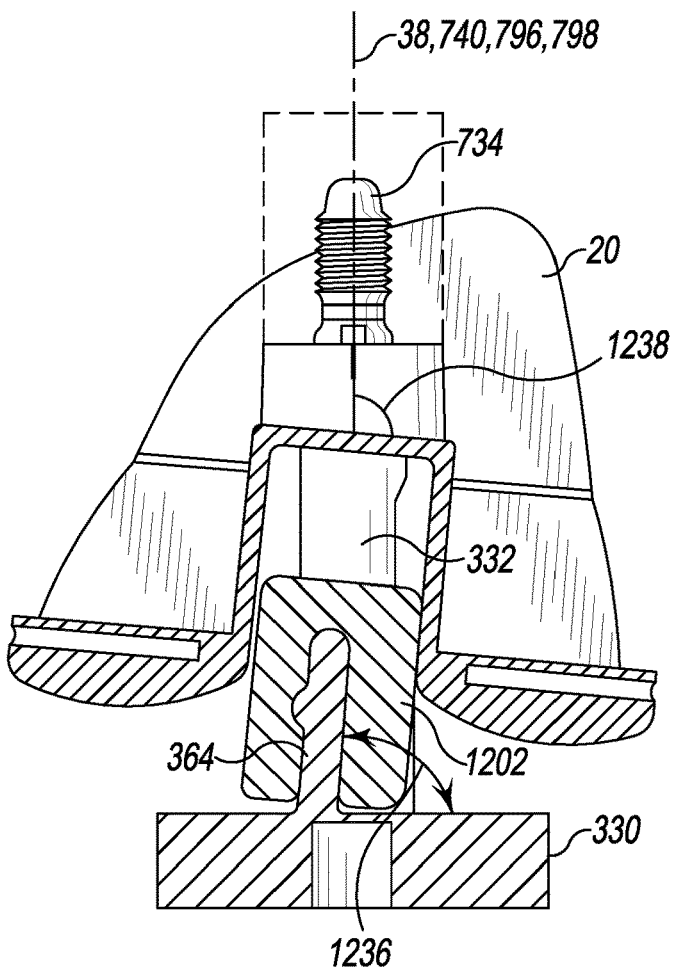
Figure 27:
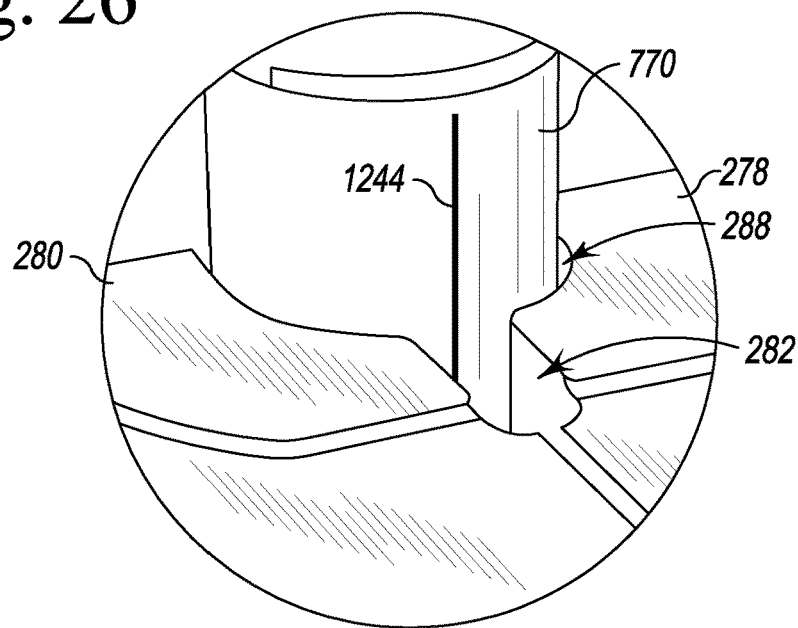

As shown in FIG. 24, the femoral trial construct 772 is positioned on the carrier 30 and the shim 1202. In that position, the axis 740 of the femoral trial component 20 and the axes 796, 798 defined by the offset adaptor 770 extend parallel to the axis 38 of the instrument base 12. As shown in FIG. 26, which is a cross-sectional view taken along the line 26-26 in FIG. 24, the post 332 and the alignment pin 352 also extend parallel to those axes. In the illustrative embodiment, the non-orthogonal angle 1236 defined between the wall 364 and the mounting block 330 of the carrier 30 is equal to non-orthogonal angle 1238 defined between the planar surface 742 and the axis 740 of the femoral trial component 20 to position the axes 740, 796, 798 parallel to the axis 38 of the base 12.

With the femoral trial construct 772 on the femoral trial carrier 30, the assembly may be rotated in either direction shown by arrow 1240 in FIG. 24 to orient the femoral trial construct 772 relative to the support arm assembly 36. In the illustrative embodiment, the femoral trial construct 772 is rotated to position the axes 740, 796, 798 in the vertically-extending orientation plane 270 defined by the axis 38 and the axis 260 of the support arm assembly 36. Additionally, the axis 798 is positioned between the axis 796 and the support arm assembly 36 in the orientation plane 270 such that the proximal sleeve 782 is positioned closer to the arm assembly 36 than the distal sleeve 780 of the offset adaptor 770. When properly positioned, the user may advance the tip 264 of the support arm assembly 36 along the axis 260 toward the femoral trial construct 772, as indicated by arrow 1242 in FIG. 24.

Figure 25:
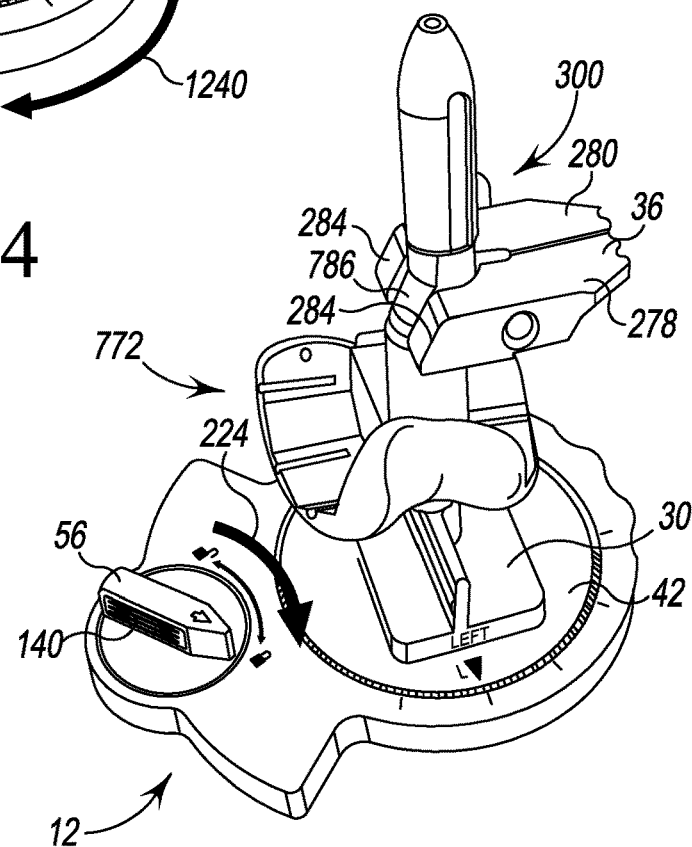

As shown in FIG. 25, the shafts 278, 280 advance over the femoral trial construct 772 to position the offset adaptor 770 in the proximal end 288 of the channel 282 of the support arm 36. The user may confirm that the femoral trial construct 772 is properly oriented by checking that the tapered surface 786 of the offset adaptor 770 faces away from the arm 36 and is aligned with the chamfered end walls 284 of the shafts 278, 280. In some embodiments, as shown in FIG. 26, the user may confirm the femoral trial construct 772 is properly oriented by checking that a visual indicia such as, for example, line 1244 defined on the offset adaptor 770 faces toward the arm 36 and is aligned with the channel 282.

Returning to FIG. 25, the user may operate the tightening mechanism 300 to secure the femoral trial construct 772 to the support arm 36. To do so, the user may rotate the knob 302 about its axis to thread the elongated shaft 304 into the threaded bore 308 and draw the shafts 278, 280 closer together. As the shafts 278, 280 move closer, the channel 282 becomes more narrow, and the shafts 278, 280 engage the offset adaptor 770.

The user may operate the locking mechanism 56 to lock the platform 42 in position relative to the arm 36 and the housing 40 of the base 12. To do so, the user may grasp the grip 146 of the knob 140 and rotate the knob 140 in the direction indicated by arrow 224 in FIG. 25. As the knob 140 is rotated, the clutch 170 of the locking mechanism 56 is rotated to advance the teeth 202 into engagement with the teeth 102 of the platform 42, thereby locking the platform 42 in position relative to the housing 40. The instrument base 12 is now able to replicate the position and orientation of the femoral trial construct 772 and is ready to begin assembly of the offset femoral prosthesis 600.

The user may operate the tightening mechanism 300 to disengage the shafts 278, 280 from the offset adaptor 770. The support arm 36 may be moved away from the femoral trial construct 772 such that the femoral trial construct 772 may be detached from the carrier 30. The user also detaches the carrier 30 from the instrument base 12. Throughout, the knob 140 (and hence the locking mechanism 56) remains in the locked position such that the platform 42 is prevented from rotating relative to the housing 40.

Figure 28:
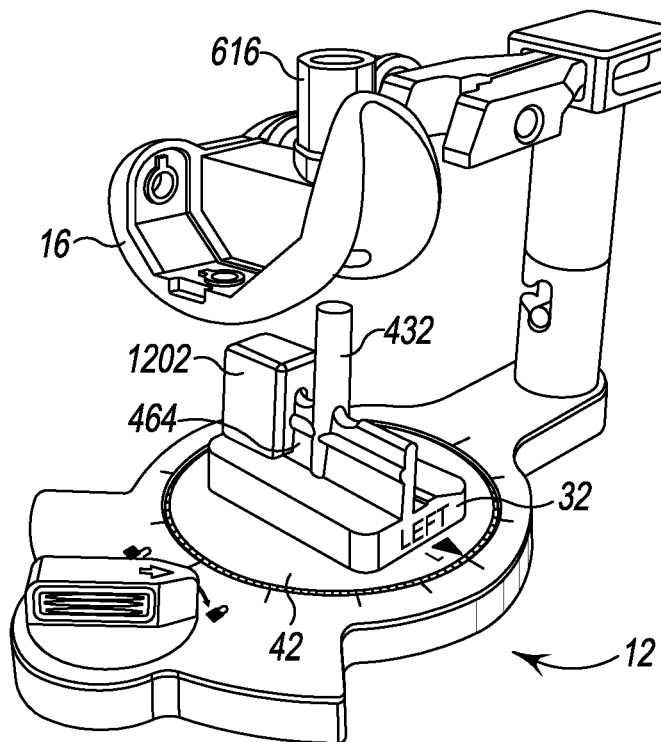

Referring now to FIG. 28, the user may attach the femoral prosthesis carrier 32 to the platform 42 by positioning the holes 320, 322 over the appropriate pins 44 of the platform 42 in a manner similar to that described above for the femoral trial carrier 30. The user may slide the same support shim 1202 onto the wall 464 of the carrier 32, as shown in FIG. 28. A prosthetic femoral component 16 corresponding to the femoral trial component 20 may be aligned with the post 432 of the carrier 32 and advanced over the post 432 to position the component 16 as shown in FIGS. 29-30.

Figure 29:
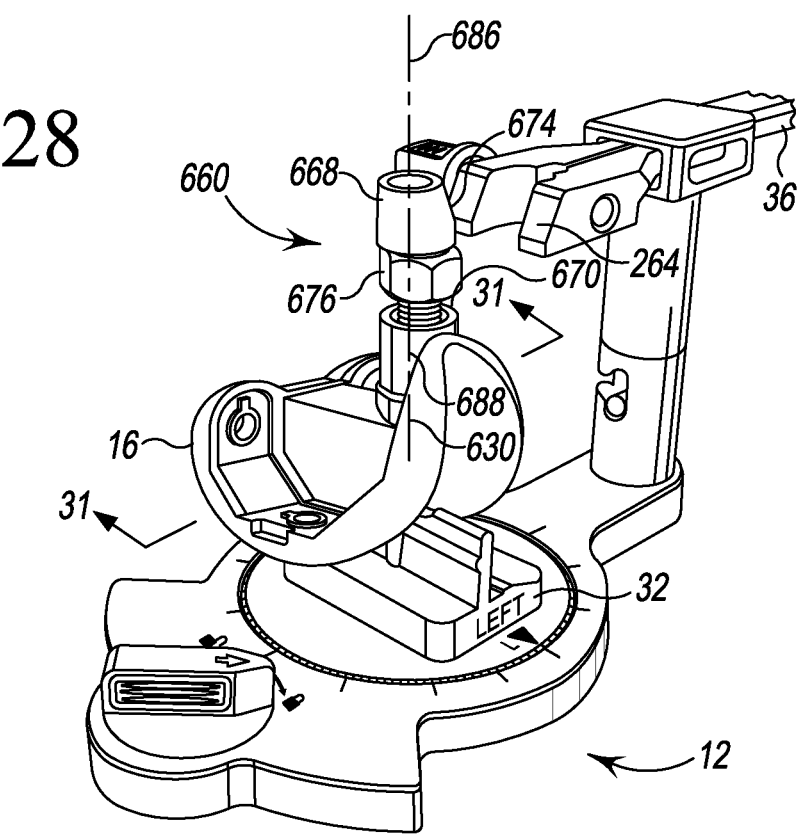
Figure 30:
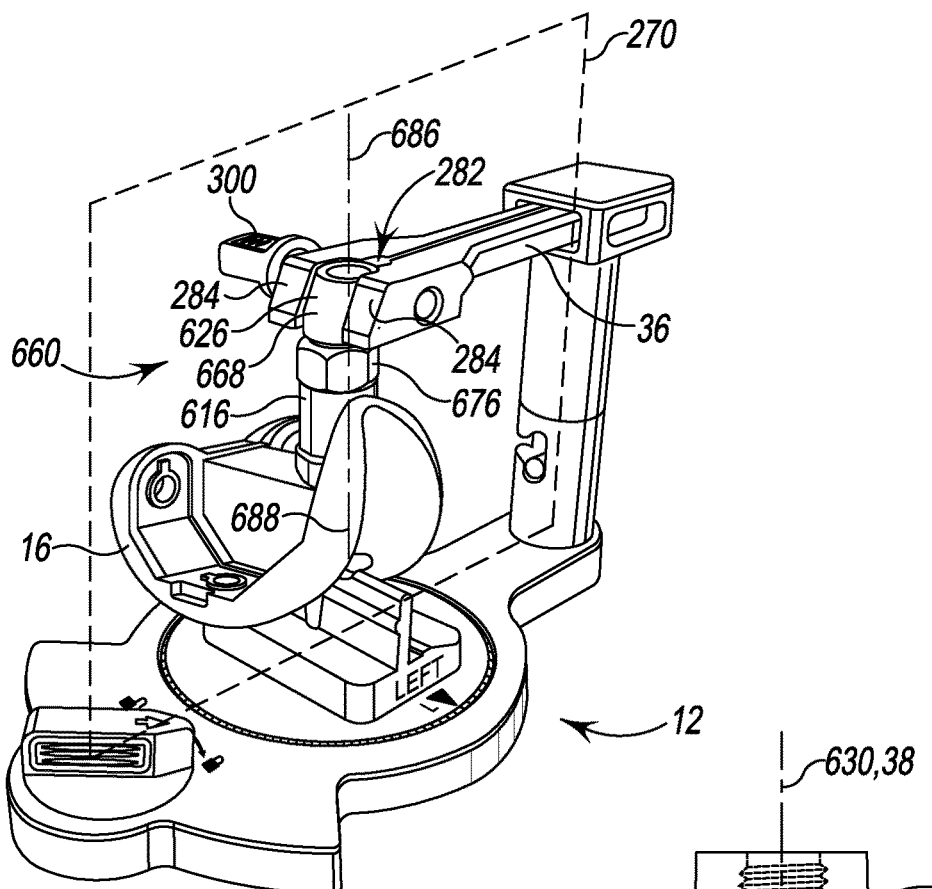
Figure 31:
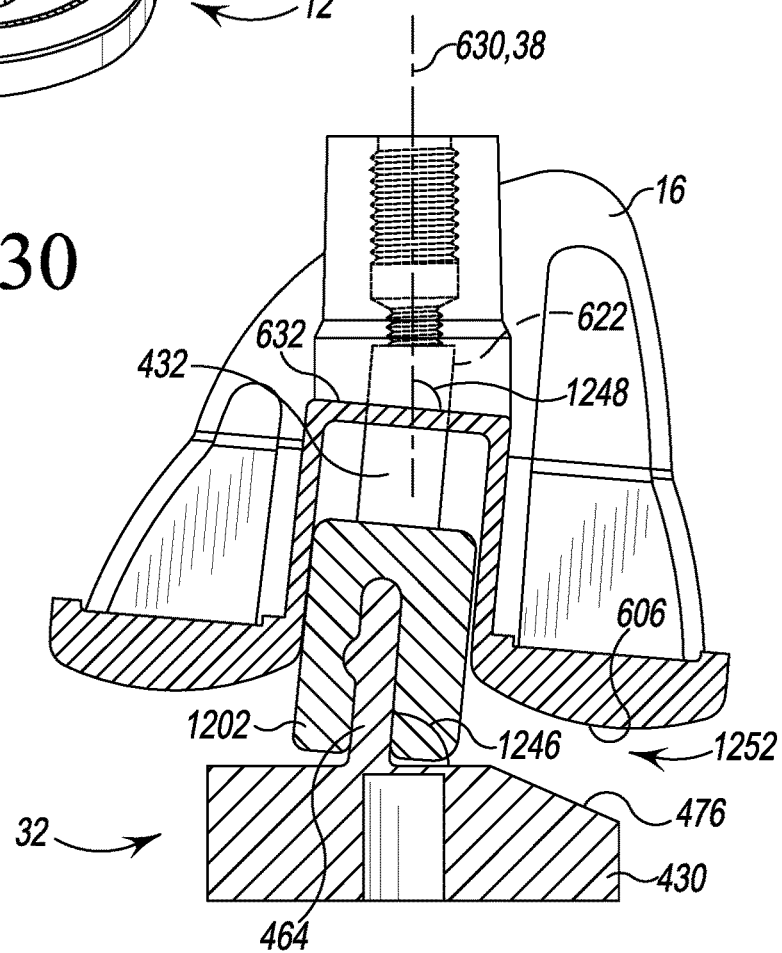

As shown in FIG. 31, which is a cross-sectional view taken along the line 31-31 in FIG. 29, the post 432 is received in the proximal opening of the bore 622 of the femoral component 16. In the illustrative embodiment, the non-orthogonal angle 1246 defined between the wall 464 and the mounting block 430 of the carrier 32 that is equal to a non-orthogonal angle 1248 defined between the planar surface 632 and the axis 630 of the femoral component 16, which position the axis 630 parallel to the axis 38 of the base 12 and in the orientation plane 270. As described above, the carrier 32 includes the section 476, which reduces the thickness of the block 430 on one side. As shown in FIG. 31, this reduced thickness maintains a gap 1252 between the block 430 and the condyle 606 of the femoral component 16.

Returning to FIG. 29, the user may attach the offset adaptor 660 to the femoral component 16. To do so, the user may align the threaded shaft 670 with the post 616 of the femoral component 16 and advance the threaded shaft 670 into the bore 622. The shaft 670 is rotated about its axis 686 to advance the locking nut 676 (which is seated against the rim wall 672 of the adaptor 660) into contact with the post 616. With the locking nut 676 seated on the post 616, the user may rotate the proximal end 668 of the adaptor 660 about the axis 686 to orient the curved tapered surface 674 away from the support arm assembly 36, as shown in FIG. 30. In that position, the axes 630, 686, 688 are positioned in the vertically-extending orientation plane 270. Additionally, the axis 686 is positioned between the axis 688 and the support arm assembly 36 in the orientation plane 270 such that the proximal end 668 of the offset adaptor 660 is positioned closer to the arm assembly 36 than the distal end 666.

The user may position the offset adaptor 660 in the channel 282 of the support arm 36 by advancing the tip 264 of the arm toward the offset adaptor 660. With the adaptor 660 positioned in the channel 282, the user may operate the tightening mechanism 300 to secure the offset adaptor 660 to the support arm 36. To do so, the user may rotate the knob 302 about its axis to thread the elongated shaft 304 into the threaded bore 308 and draw the shafts 278, 280 closer together. As the shafts 278, 280 move closer, the channel 282 becomes more narrow, and the shafts 278, 280 engage the offset adaptor 660, as shown in FIG. 30.

With the offset adaptor 660 retained in the support arm assembly 36, the user may use a torque wrench (not shown) to tighten the locking nut 676 against the post 616 to add a preload to the components 16, 660. In the illustrative embodiment, the preload places the threaded section 624 of the post 616 and the thread shaft 670 in tension, thereby securing the component 16 to the offset adaptor 660.

Figure 32:
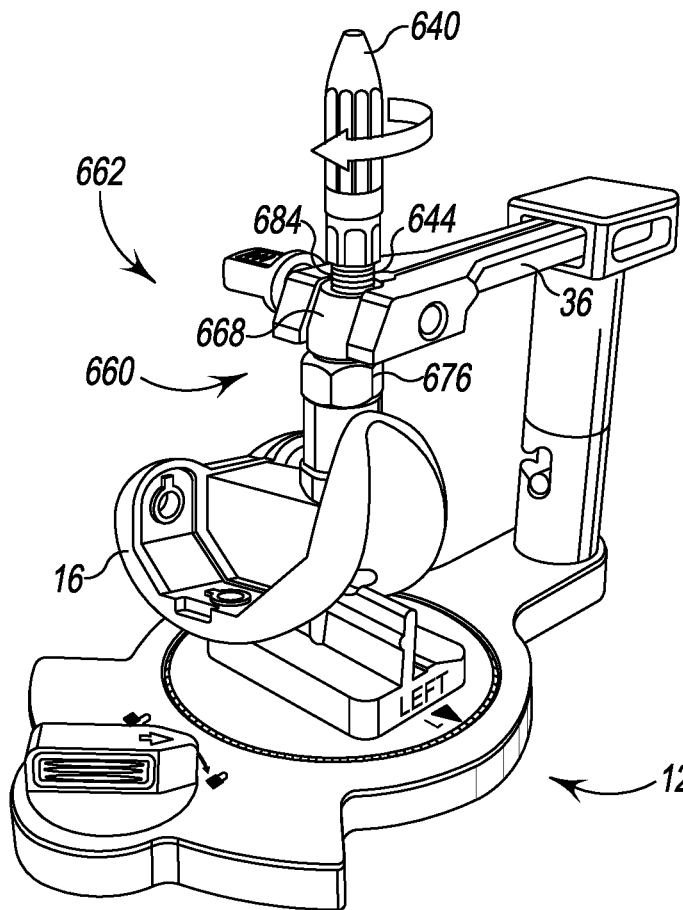

Referring now to FIG. 32, the user may select a stem component 640 for the prosthesis 662 based on the configuration (e.g., length) of the stem component 750. The user may then secure the stem component 640 to the proximal end 668 of the offset adaptor 660 by threading the distal end 644 of the stem component 640 into the threaded bore 684 of the proximal end 668. The user may use a torque wrench (not shown) to tighten the stem component 640 against the offset adaptor 660 to add a preload to the components 640, 660 and form the offset prosthesis 662. In this way, the orientation and positioning of the offset trial construct 772 is replicated in the offset prosthesis 662. The user may then detach the support arm assembly 36 from the prosthesis 662 and remove the prosthesis 662 from the carrier 32 for implantation into the patient's femur.

Figure 33:
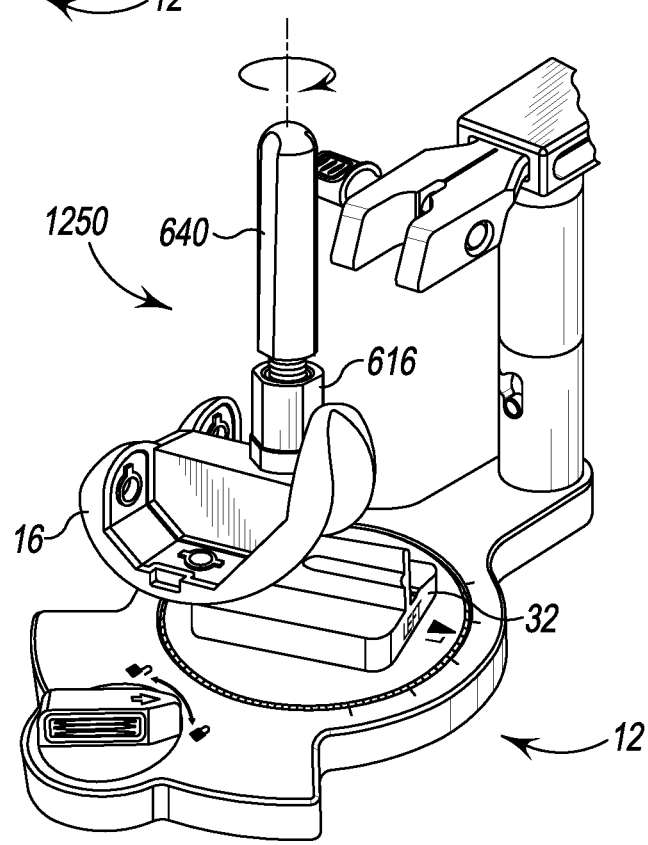

As shown in FIG. 33, the instrument base 12, the carrier 32, and other instruments of system 10 may be used to assemble a straight stem femoral prosthesis 1250. In the illustrative embodiment, the straight stem femoral prosthesis 1250 includes the femoral component 16 and a stem component 640, which is secured to the post 616 of the femoral component 16. As shown in FIG. 33, the femoral component 16 is mounted to the base 12 in a manner similar to that described above. It should be appreciated that the support arm 36 is advanced over the stem component 640 and operated to constrain the stem component 640 during torquing as described above.

Figure 34:
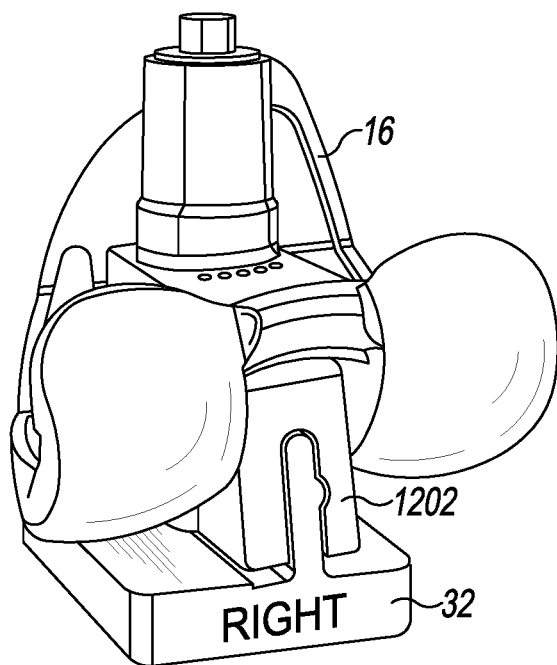
Figure 35:
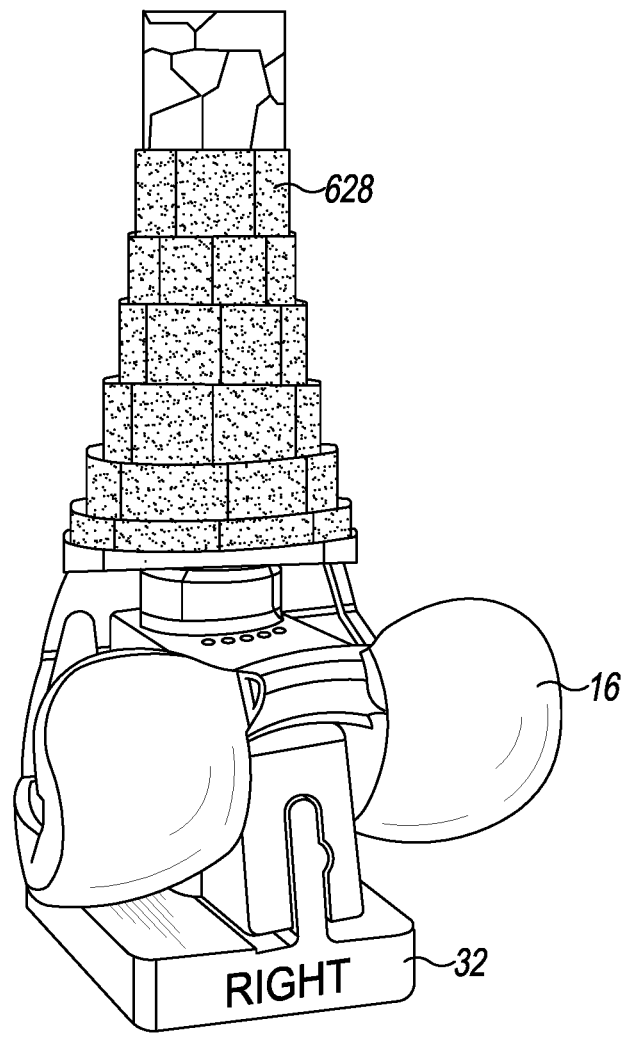

Referring now to FIGS. 34-37, the carrier 32 and the sleeve impactor 1090 may be used to assemble a femoral sleeve prosthesis assembly 704. To do so, the femoral component 16 is mounted on the carrier 32 and the shim 1202 as shown in FIG. 34 in a manner similar to that described above. The sleeve component 628 may then be advanced over the post 616 of the femoral component 16. As shown in FIG. 35, the post 616 is received in an opening defined in the distal end 692. As described above, the distal opening is defined by a tapered inner surface that corresponds to the tapered outer surface 626 of the post 616 such that the sleeve component 628 may be secured to the post 616 via a taper lock.

Figure 36:
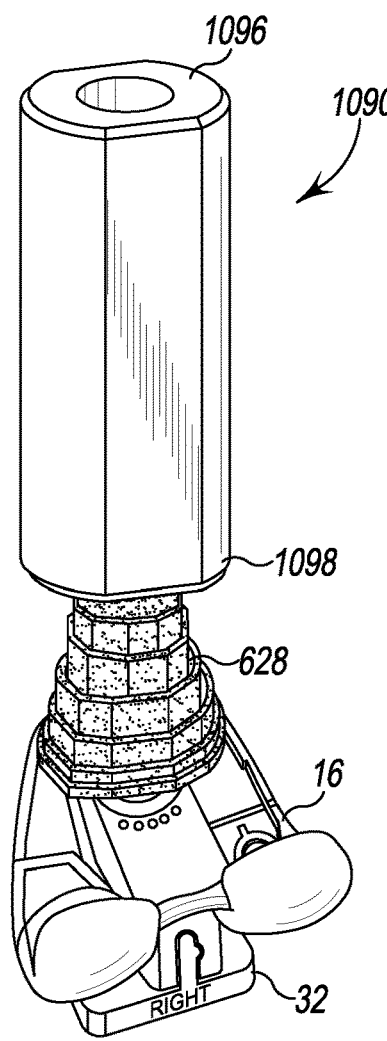

To create the taper lock, the user may utilize the sleeve impactor 1090 to engage the proximal end 694 of the sleeve component 628. As shown in FIG. 36, the proximal end 694 of the sleeve component 628 is positioned in the aperture 1098 defined in the femoral impaction end 1094. The user may use a mallet or other instrument to tap on the tibial impaction end 1096 to advance the sleeve component 628 along the post 616 and create the taper lock.

As described above, the sleeve component 628 is configured to be secured to a stem component 640. To do so, the threaded distal end 646 of the stem component 640 is threaded into the threaded bore 650 defined in the proximal end 694 of the sleeve component 628. The user may use a torque wrench (not shown) to tighten the stem component 640 against the sleeve component 628 to add a preload to the components 628, 640 and form the sleeve prosthesis assembly 704.

Figure 37:
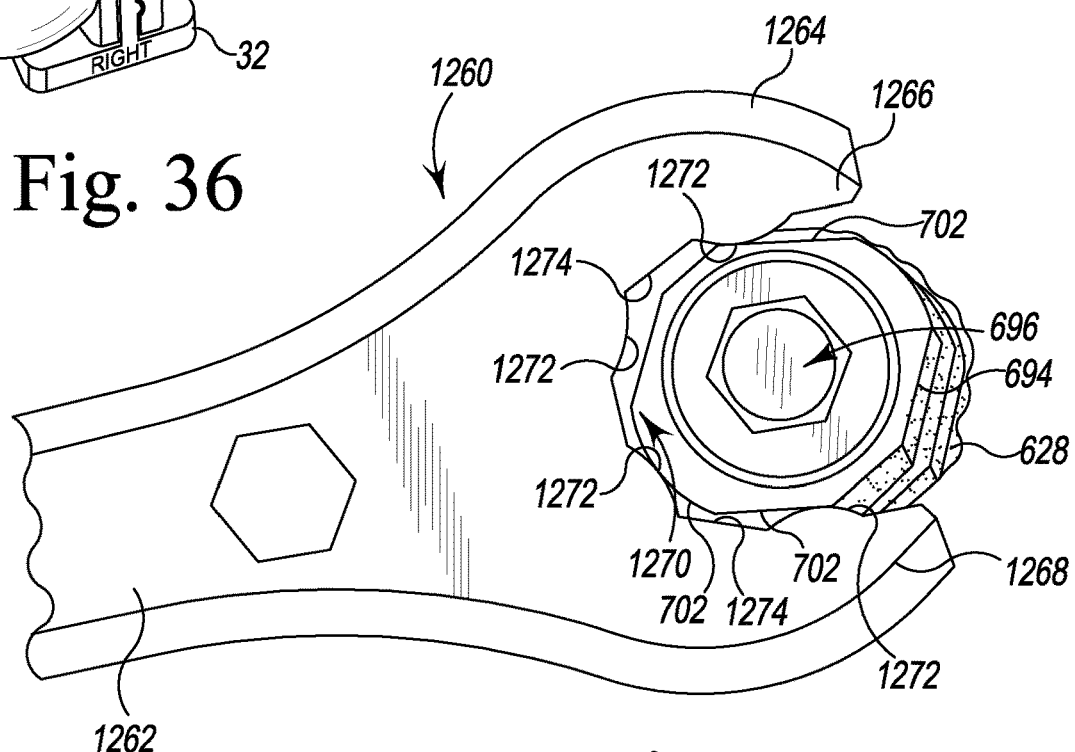

To hold sleeve component 628 in position while applying torque to the stem component 640, the user may utilize the wrench 1260 shown in FIG. 37. The wrench 1260 includes an elongated handle 1262 and a head 1264 attached to the handle 1262. The head 1264 includes a pair of arms 1266, 1268 that defined a slot 1270 sized to receive the proximal end 694 of the sleeve component 628. Each arm 1266, 1268 includes a plurality of surfaces 1274 that define the slot 1270 and a plurality of lobes 1272 that extend from the surfaces 1274 into the slot 1270. Each lobe 1272 is rounded and configured to the flat surfaces (as opposed to the edges) of the proximal end 694 of the sleeve 628.

As described above, during surgery, the surgeon may position a tibial trial construct 1032 on a patient's tibia and rotate the tibial trial component 22 relative to the distal axis 1060 (and hence the stem component 1020) of the offset adapter 1030 to change the position of the trial component 22 on the proximal end of the patient's tibia. When the tibial trial component 22 is properly positioned on the patient's tibia, the surgeon may operate the bolt 1012 to lock the proximal sleeve 1040 of the offset adaptor 1030 in position relative to the distal sleeve 1042, thereby locking the tibial trial component 22 in a desired orientation and position relative to the stem component 1020.

Referring now to FIGS. 38-43, the instrument system 10 may be used to assemble an offset tibial prosthesis assembly 962 based on the configuration of the tibial trial construct 1032 created as described above. In other words, the surgeon may utilize the instrument system 10 to secure the prosthetic tibial component 18 to the stem component 940 in a position and orientation that matches the desired orientation and position of the tibial trial component 22 determined during the surgical procedure. In that way, the assembled offset tibial prosthesis 962 replicates and matches the configuration of the tibial trial construct 1032.

Figure 38:
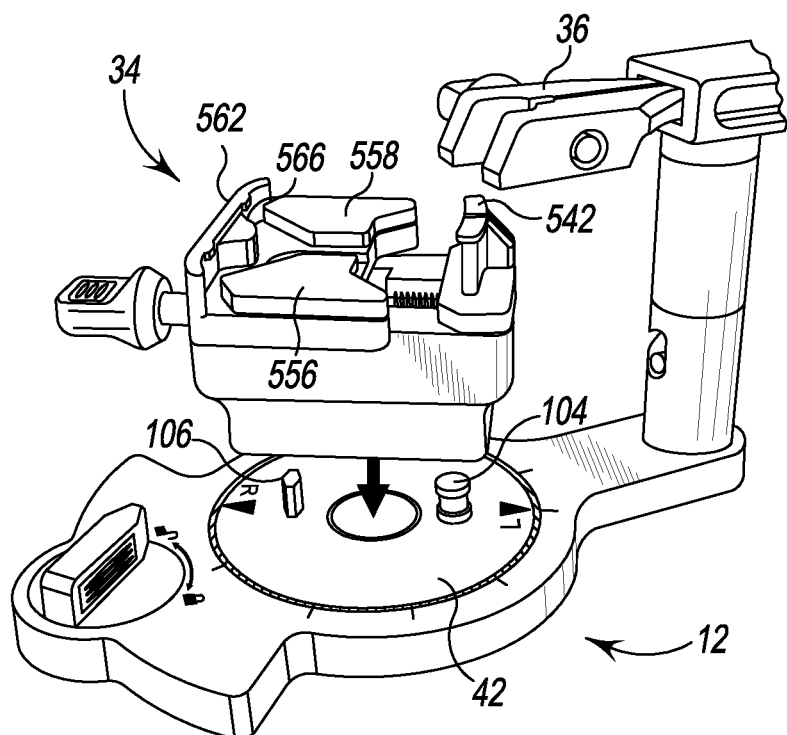

To do so, the user may attach the appropriate modular instruments 14 to the instrument base 12, including the support arm assembly 36 and the tibial component carrier 34. To attach the tibial component carrier 34 to the instrument base 12, the user may align the orientation holes 320, 322 with the cylindrical pin 104 and the polygonal pin 106, respectively, on the base platform 42, as shown in FIG. 38. The user may then advance the carrier 34 over the pins 104, 106 to position the mounting block 500 of the carrier 34 on the platform 42. When the locking mechanism 56 is in the unlocked position, the user may rotate the platform 42 (and hence the carrier 34) about the axis 38 to position the carrier 34 as shown in FIG. 39.

Figure 39:
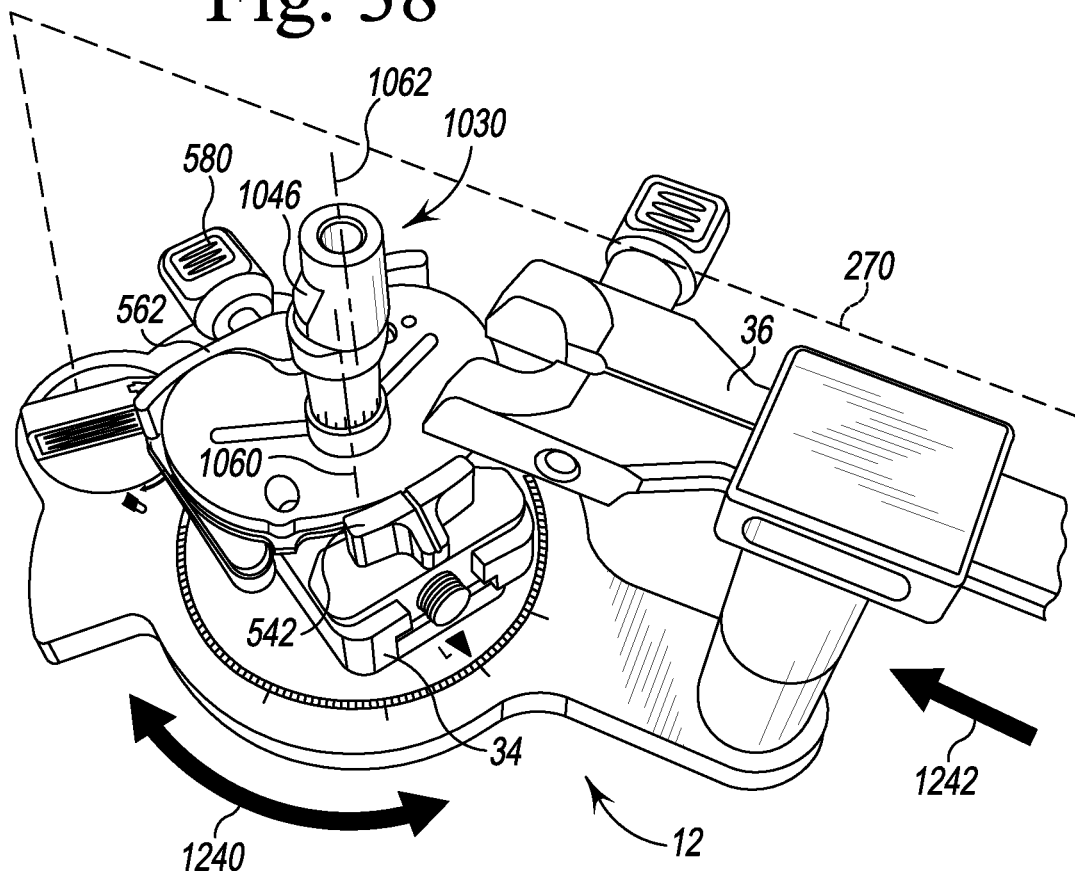

The user may position the tibial trial construct 1032 on the carrier 34, as shown in FIG. 39. In the illustrative embodiment, the stem component 1020 of the construct 1032 has been detached for ease of viewing. It should be appreciated that the stem component 1020 may be attached during each of the steps described below. To attach the construct 1032 to the carrier 34, the user aligns the tabs 1018 of the trial 22 with the Y-shaped channel 560 defined in the clamp plate

504. The user may then move the base 1002 of the trial 22 into contact with the pads 556, 558 of the clamp plate 504. As shown in FIG. 39, the inner wall 566 of the jaw 562 is positioned between the posterior sections 1010 and in the concave posterior section 1016. The anterior wall section 1008 faces the jaw 542 of the carrier 34. The user may then utilize the knob 580 to advances the jaw 542, 562 toward each other and clamp the base 1002 between them.

As shown in FIG. 39, the tibial trial construct 1032 is positioned on the carrier 34. In that position, the axes 1014, 1060, 1062 extend parallel to the axis 38 of the instrument base 12. With the tibial trial construct 1032 on the carrier 34, the assembly may be rotated in either direction shown by arrow 1240 to orient the tibial trial construct 1032 relative to the support arm assembly 36. In the illustrative embodiment, the tibial trial construct 1032 is rotated to position the axes 1014, 1060, 1062 in the vertically-extending orientation plane 270. Additionally, the axis 1062 is positioned between the axis 1060 and the support arm assembly 36 in the orientation plane 270 such that the distal sleeve 1042 is positioned closer to the arm assembly 36 than the proximal sleeve 1040 of the offset adaptor 1030. When properly positioned, the user may advance the tip 264 along the axis 260 toward the tibial trial construct 1032, as indicated by arrow 1242.

Figure 40:
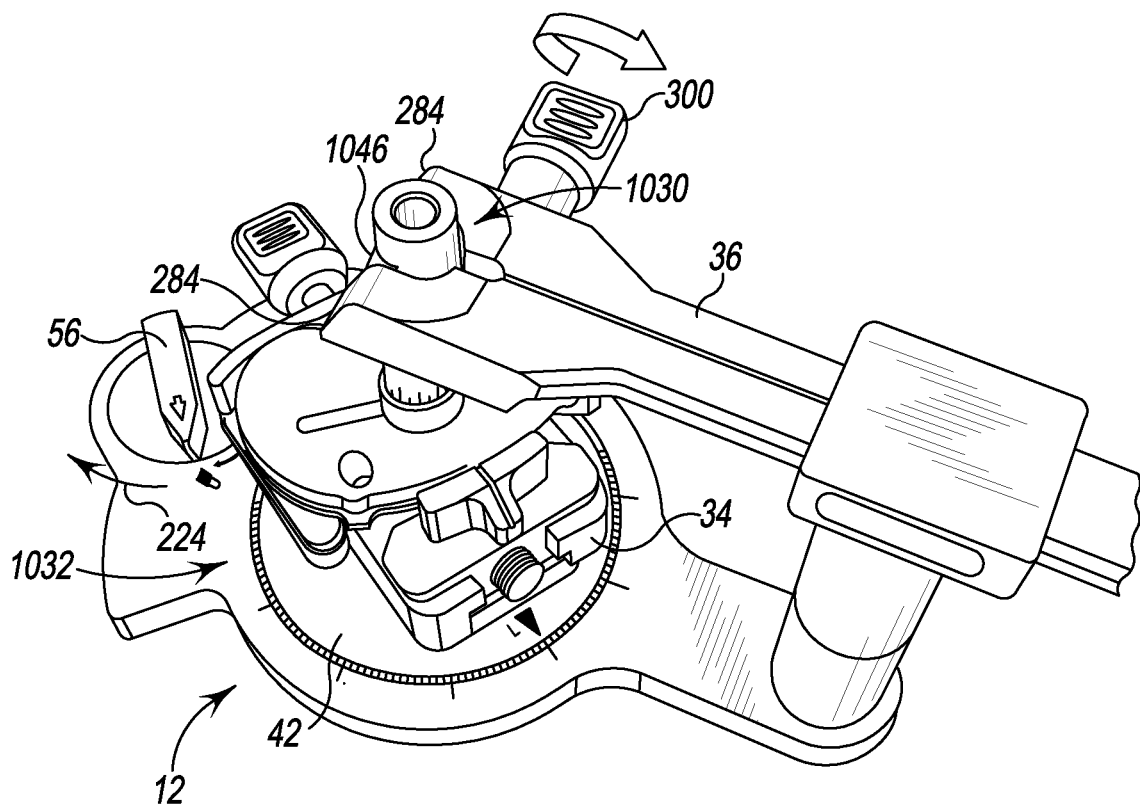

As shown in FIG. 40, the shafts 278, 280 advance over the tibial trial construct 1032 to position the offset adaptor 1030 in the proximal end 288 of the channel 282 of the support arm 36. The user may confirm that the tibial trial construct 1032 is properly oriented by checking that the tapered surface 1046 of the offset adaptor 1030 faces away from the arm 36 and is aligned with the chamfered end walls 284 of the shafts 278, 280. In some embodiments, the user may confirm the tibial trial construct 1032 is properly oriented by checking that a visual indicia defined on the offset adaptor 1030 faces toward the arm 36 and is aligned with the channel 282.

The user may operate the tightening mechanism 300 to secure the tibial trial construct 1032 to the support arm 36. To do so, the user may rotate the knob 302 about its axis to thread the elongated shaft 304 into the threaded bore 308 and draw the shafts 278, 280 closer together. As the shafts 278, 280 move closer, the channel 282 becomes more narrow, and the shafts 278, 280 engage the offset adaptor 1030. The user may also operate the locking mechanism 56 to lock the platform 42 in position relative to the arm 36 and the housing 40 of the base 12. To do so, the user may grasp the grip 146 of the knob 140 and rotate the knob 140 in the direction indicated by arrow 224 in FIG. 40.

With the platform 42 prevented from rotating, the user may operate the tightening mechanism 300 to disengage the shafts 278, 280 from the offset adaptor 1030. The support arm 36 may be moved away from the tibial trial construct 1032 such that the tibial trial construct 1032 may be detached from the carrier 34.

Figure 41:
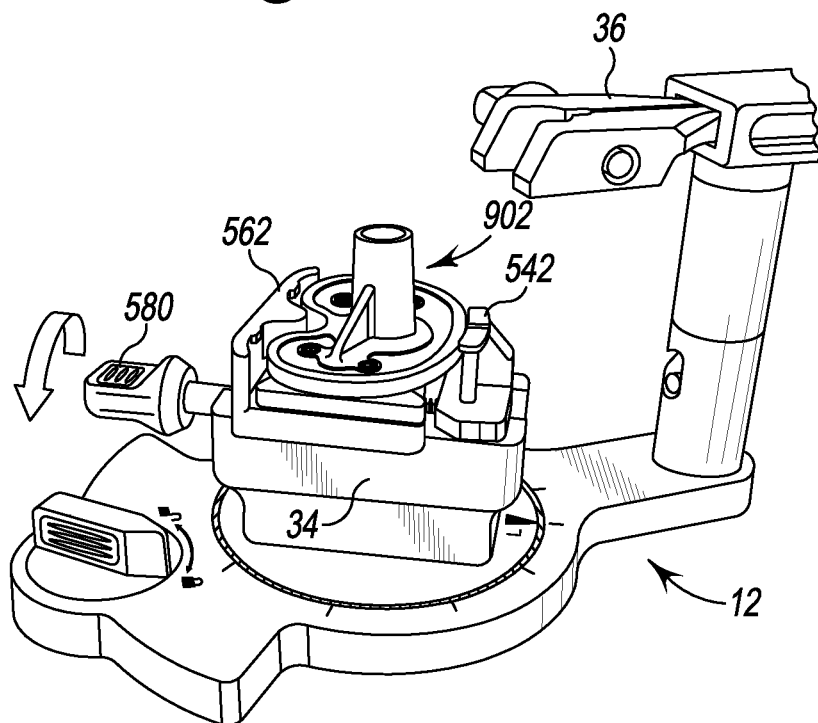

A prosthetic tibial component 18 such as tray 902 corresponding to the tibial trial component 22 may be attached to the carrier 34 in place of the tibial trial construct 1032, as shown in FIG. 41. To do so, the user aligns the Y-shaped buttress 914 of the tray 902 with the Y-shaped channel 560 defined in the clamp plate 504. The user may then move the platform 904 of the tibial tray 902 into contact with the pads 556, 558 of the clamp plate 504. As shown in FIG. 39, the inner wall 566 of the jaw 562 is positioned between the posterior sections 938 and in the concave posterior section 936. The anterior wall section 934 faces the jaw 542 of the carrier 34. The user may then utilize the knob 580 to advances the jaw 542, 562 toward each other and clamp the tibial tray 902 between them.

Figure 42:
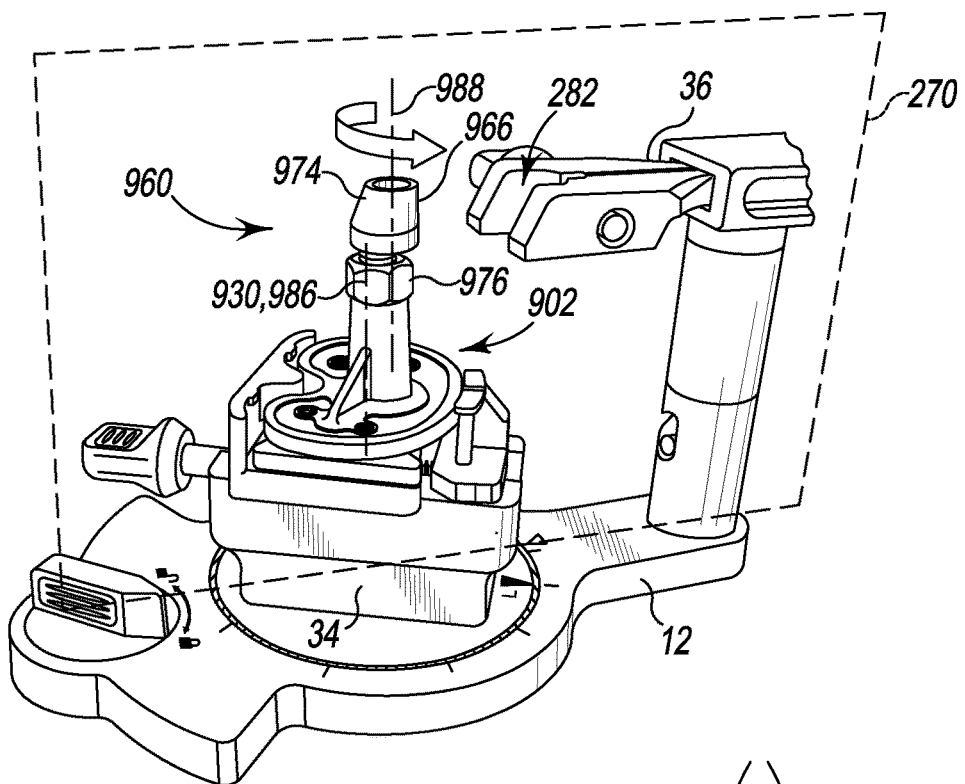

Referring now to FIG. 42, the user may attach the offset adaptor 960 to the tibial tray 902. To do so, the user may align the threaded shaft 970 with the post 906 of the tibial tray 902 and advance the threaded shaft 970 into the bore 922. The shaft 970 is rotated about its axis 988 to advance the locking nut 976 (which is seated against the rim wall 972 of the adaptor 960) into contact with the post 906. With the locking nut 976 seated on the post 906, the user may rotate the distal end 966 of the adaptor 960 about the axis 988 to orient the curved tapered surface 974 away from the support arm assembly 36, as shown in FIG. 42. In that position, the axes 930, 986, 988 are positioned in the vertically-extending orientation plane 270. Additionally, the axis 988 is positioned between the axis 986 and the support arm assembly 36 in the orientation plane 270 such that the distal end 966 of the offset adaptor 960 is positioned closer to the arm assembly 36 than the distal end 666.

Figure 43:
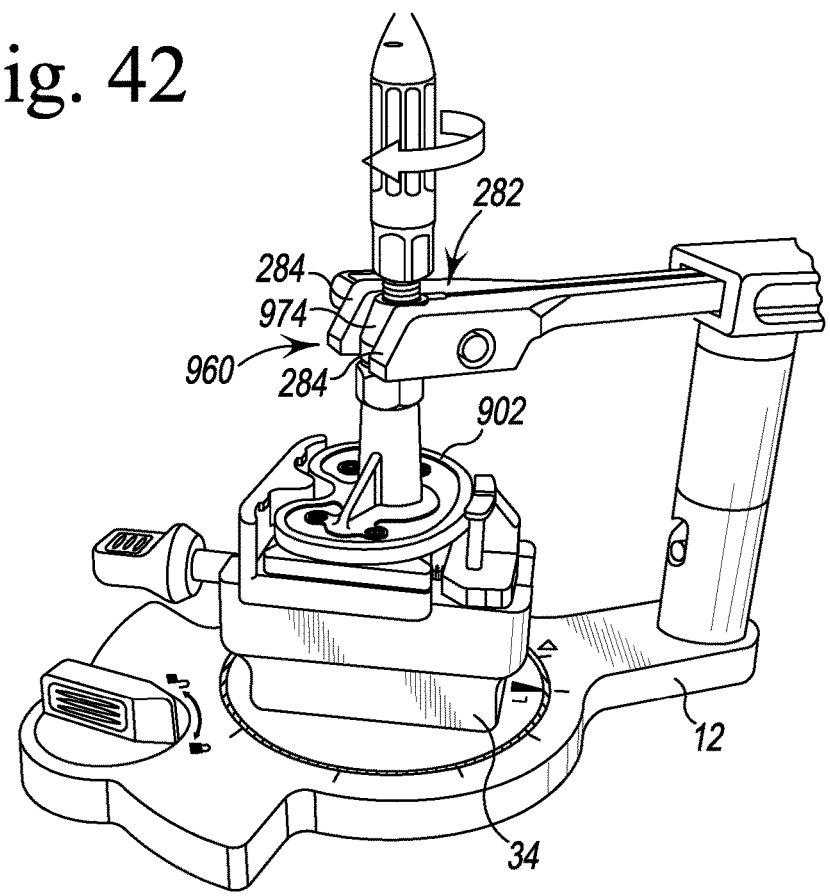

The user may position the offset adaptor 960 in the channel 282 of the support arm 36 by advancing the tip 264 of the arm toward the offset adaptor 960. With the adaptor 960 positioned in the channel 282, the user may operate the tightening mechanism 300 to secure the offset adaptor 960 to the support arm 36. To do so, the user may rotate the knob 302 about its axis to thread the elongated shaft 304 into the threaded bore 308 and draw the shafts 278, 280 closer together. As the shafts 278, 280 move closer, the channel 282 becomes more narrow, and the shafts 278, 280 engage the offset adaptor 960, as shown in FIG. 43.

With the offset adaptor 960 griped by the support arm assembly 36, the user may use a torque wrench (not shown) to tighten the locking nut 976 against the post 906 to add a preload to the components 18, 960. In the illustrative embodiment, the preload places the threads in the bore 922 of the post 616 and the threaded shaft 970 in tension, thereby securing the component 18 to the offset adaptor 960.

The user may select a stem component 940 for the prosthesis 962 based on the configuration (e.g., length) of the stem component 1020. The user may then secure the stem component 940 to the distal end 966 of the offset adaptor 960 by threading the proximal end 944 of the stem component 940 into the threaded bore 982 of the adaptor 960. The user may use a torque wrench (not shown) to tighten the stem component 940 against the offset adaptor 960 to add a preload to the components 940, 960 and form the offset prosthesis 962. In this way, the orientation and positioning of the offset trial construct 1032 is replicated in the offset prosthesis 962. The user may then detach the support arm assembly 36 from the prosthesis 962 and remove the prosthesis 962 from the carrier 34 for implantation into the patient's tibia.

Figure 44:
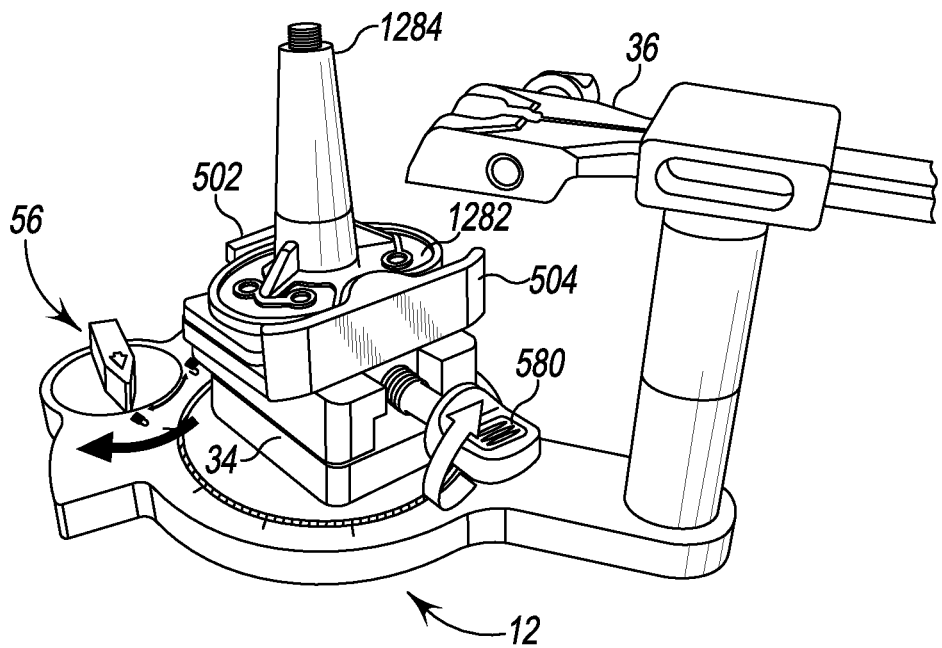
Figure 45:
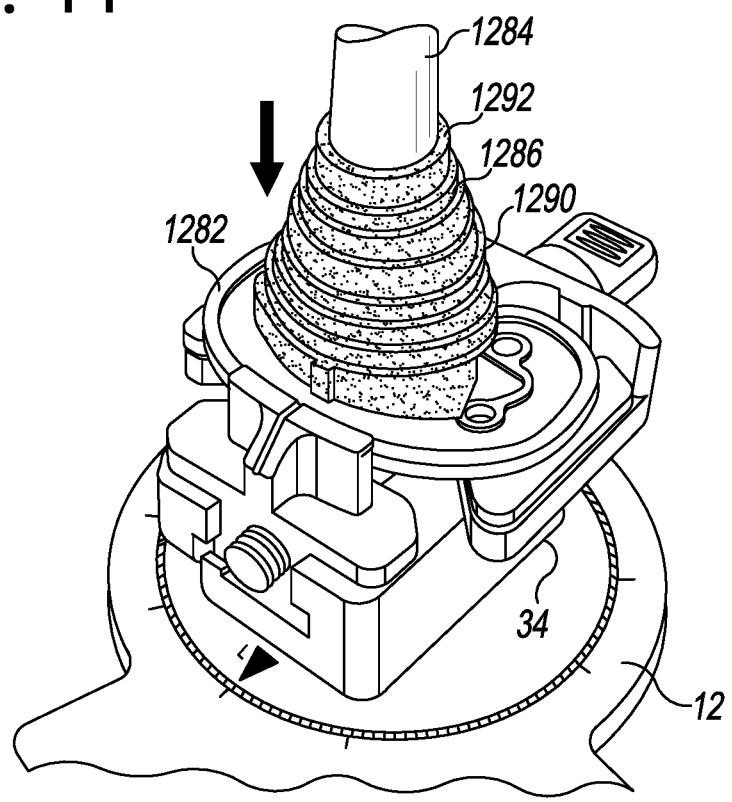

As shown in FIGS. 44-47, the instrument base 12, the carrier 34, and other instruments of system 10 may be used to assemble a tibial sleeve prosthesis 1280. In the illustrative embodiment, the prosthesis 1280 includes a tibial tray 1282 similar to the tibial tray 902, except for a longer and tapered stem post 1284, as shown in FIG. 44. The prosthesis 1280 also includes a sleeve component 1286 configured to be positioned on the tapered stem post 1284, as shown in FIG. 45. The sleeve component 1286 includes a stepped outer wall 1290 and a tapered inner wall (not shown) configured to secure the sleeve component 1286 to the tibial tray 1282 via a taper lock.

As shown in FIG. 44, the tibial tray 1282 is mounted to the base 12 using the carrier 34 in a manner similar to that described above. It should be appreciated that the support arm 36 is not necessary to assemble the tibial sleeve prosthesis 1280. With the tibial tray 1282 positioned on the carrier 34, the sleeve component 1286 is advanced over the post 1284, as shown in FIG. 45.

Figure 46:
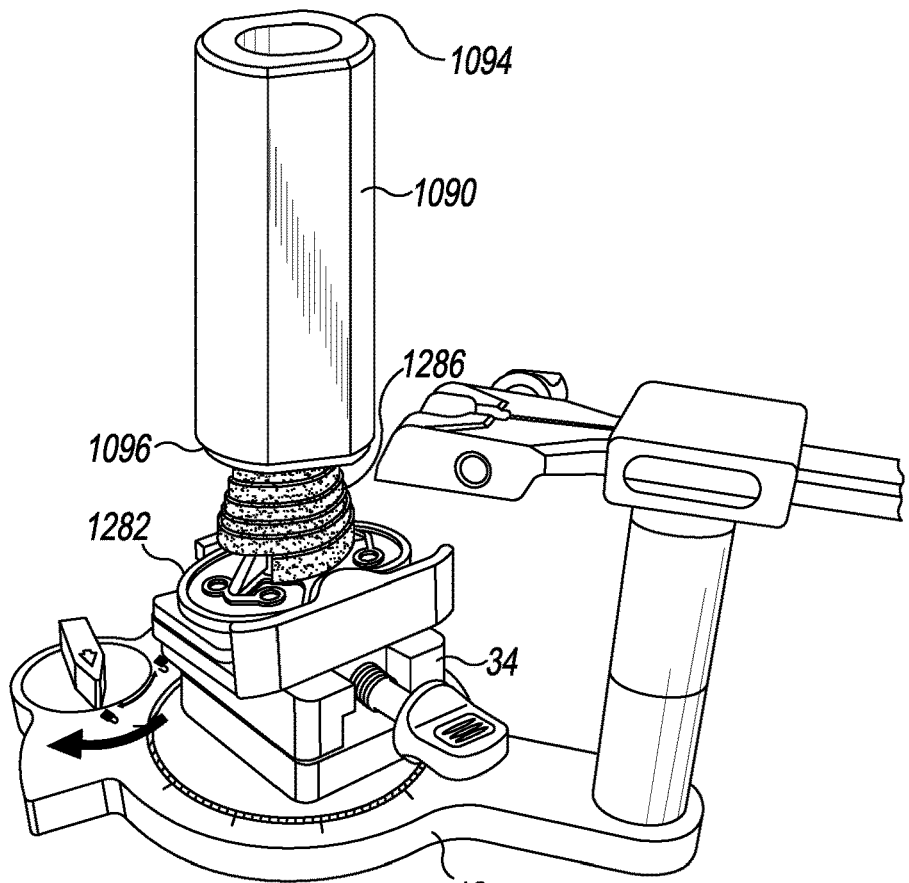

To create the taper lock, the user may utilize the sleeve impactor 1090 to engage the distal end 1292 of the sleeve component 1286. As shown in FIG. 46, the distal end 1292 of the sleeve component 1286 is positioned in the aperture 1102 defined in the tibial impaction end 1096. The user may use a mallet or other instrument to tap on the femoral impaction end 1094 to advance the sleeve component 1286 along the post 1284 and create the taper lock.

Figure 47:
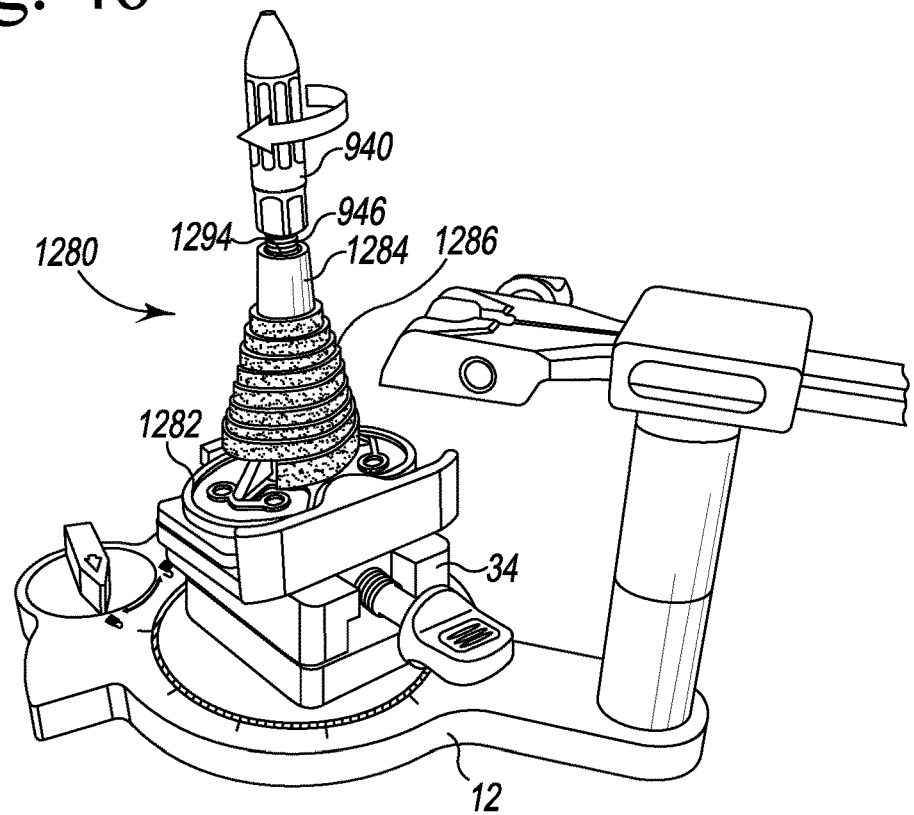

The post 1284 of the tibial tray 1282 is configured to be secured to a stem component 940. To do so, the threaded proximal end 944 of the stem component 940 is threaded into a threaded bore 1294 defined in the distal end 1296 of the post 1284, as shown in FIG. 47. The user may use a torque wrench (not shown) to tighten the stem component 940 against the tibial tray 1282 to add a preload to the 940, 1282 and form the sleeve prosthesis assembly 1280.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A surgical instrument system, comprising:
a base including a mounting platform that is rotatable to permit the mounting platform to rotate 360 degrees about a vertical axis extending through the base, and
a tibial carrier configured to be selectively positioned on the mounting platform, the tibial carrier including a first clamp plate and a second clamp plate that are moveable to grip a prosthetic tibial component between the first clamp plate and the second clamp plate.

2. The surgical instrument system of claim 1, wherein one of the first clamp plate and the second clamp plate includes a concave curved wall shaped to engage a convex curved anterior wall of the prosthetic tibial component.

3. The surgical instrument system of claim 2, wherein the other of the first clamp plate and the second clamp plate includes a convex curved wall positioned between, and connected to, a pair of concave curved walls, the convex curved wall and the pair of concave curved walls being shaped to engage a posterior wall of the prosthetic tibial component.

4. The surgical instrument system of claim 1, wherein the second clamp plate includes a rear slot sized to receive a posterior buttress of the prosthetic tibial component and a forward slot sized to receive an anterior buttress of the prosthetic tibial component.

5. The surgical instrument system of claim 1, wherein the tibial carrier includes a screw-type mechanism to move the second clamp plate and the first clamp plate.

6. The surgical instrument system of claim 1, wherein the base includes a stationary housing and the mounting platform is rotatively coupled to the stationary housing to permit the mounting platform to rotate 360 degrees relative to the stationary housing about the vertical axis.

7. The surgical instrument system of claim 6, wherein the base further includes a locking clutch operable to prevent the mounting platform from rotating relative to the stationary housing.

8. The surgical instrument system of claim 1, further comprising a support arm positioned above the base, the support arm being moveable in a horizontal plane relative to the mounting platform.

9. The surgical instrument system of claim 8, wherein the support arm includes:
an elongated body positioned in the horizontal plane,
a first shaft positioned in the horizontal plane and extending outwardly from the elongated body to a proximal surface,
a second shaft extending outwardly from the elongated body parallel to the first shaft to the proximal surface, and
a channel defined between the first shaft and the second shaft, the channel being sized to receive a portion of a prosthetic trial component positioned on the tibial carrier when the tibial carrier is coupled to the mounting platform.

10. The surgical instrument system of claim 9, further comprising a user-operated knob operable to move the first shaft toward the second shaft to decrease a width of the channel.

11. The surgical instrument system of claim 1, wherein:
the mounting platform includes a pair of upwardly-extending pins, and
the tibial carrier includes a pair of apertures sized to separately receive the upwardly-extending pins.

12. A surgical instrument system, comprising:
a base including (i) a stationary housing, (ii) a mounting platform that is rotatively coupled to the stationary housing to permit the mounting platform to rotate 360 degrees about a vertical axis extending through the stationary housing, and (iii) a locking clutch operable to prevent the mounting platform from rotating relative to the stationary housing,
a support arm removably coupled to the stationary housing, the support arm being moveable in a horizontal plane relative to the vertical axis, and
a tibial carrier configured to be coupled to the mounting platform to rotate with the mounting platform.

13. The surgical instrument system of claim 12, wherein the tibial carrier includes a first clamp plate and a second clamp plate that are moveable to grip a prosthetic tibial component between the first clamp plate and the second clamp plate.

14. The surgical instrument system of claim 12, wherein one of the first clamp plate and the second clamp plate includes a concave curved wall shaped to engage a convex curved anterior wall of the prosthetic tibial component.

15. The surgical instrument system of claim 14, wherein the other of the first clamp plate and the second clamp plate includes a convex curved wall positioned between, and connected to, a pair of concave curved walls, the convex curved wall and the pair of concave curved walls being shaped to engage a posterior wall of the prosthetic tibial component.

16. The surgical instrument system of claim 12, wherein the second clamp plate includes a rear slot sized to receive a posterior buttress of the prosthetic tibial component and a forward slot sized to receive an anterior buttress of the prosthetic tibial component.

17. The surgical instrument system of claim 12, wherein the tibial carrier includes a screw-type mechanism to move the second clamp plate and the first clamp plate.

18. The surgical instrument system of claim 12, wherein the support arm includes:
   an elongated body positioned in the horizontal plane,
   a first shaft positioned in the horizontal plane and extending outwardly from the elongated body to a proximal surface,
   a second shaft extending outwardly from the elongated body parallel to the first shaft to the proximal surface, and
   a channel defined between the first shaft and the second shaft, the channel being sized to receive a portion of a prosthetic tibial component positioned on the tibial carrier when the tibial carrier is coupled to the mounting platform.

19. The surgical instrument system of claim 18, further comprising a user-operated knob operable to move the first shaft toward the second shaft to decrease a width of the channel.

20. The surgical instrument system of claim 12, wherein:
   the mounting platform includes a pair of upwardly-extending pins, and
   the tibial carrier includes a pair of apertures sized to separately receive the upwardly-extending pins.

* * * * *